US011993587B2

(12) United States Patent
Dvorak et al.

(10) Patent No.: US 11,993,587 B2
(45) Date of Patent: *May 28, 2024

(54) SUBSTITUTED PYRAZOLO-PYRAZINES AND THEIR USE AS GluN2B RECEPTOR MODULATORS

(71) Applicant: JANSSEN PHARMACEUTICA NV, Beerse (BE)

(72) Inventors: Curt Dvorak, Poway, CA (US); Heather Coate, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 395 days.

This patent is subject to a terminal disclaimer.

(21) Appl. No.: 17/618,068

(22) PCT Filed: Jun. 12, 2020

(86) PCT No.: PCT/EP2020/066405
§ 371 (c)(1),
(2) Date: Dec. 10, 2021

(87) PCT Pub. No.: WO2020/249802
PCT Pub. Date: Dec. 17, 2020

(65) Prior Publication Data
US 2022/0315590 A1 Oct. 6, 2022

Related U.S. Application Data

(60) Provisional application No. 62/861,681, filed on Jun. 14, 2019.

(51) Int. Cl.
*C07D 403/04* (2006.01)
*A61P 25/18* (2006.01)
*A61P 25/24* (2006.01)
*C07D 487/04* (2006.01)

(52) U.S. Cl.
CPC ............ *C07D 403/04* (2013.01); *A61P 25/18* (2018.01); *A61P 25/24* (2018.01); *C07D 487/04* (2013.01)

(58) Field of Classification Search
CPC ..... C07D 403/04; C07D 487/04; A61P 25/18; A61P 25/24
See application file for complete search history.

(56) References Cited

U.S. PATENT DOCUMENTS

| | | | |
|---|---|---|---|
| 7,622,486 B2 | 11/2009 | Pal et al. | |
| 8,372,835 B2 | 2/2013 | Binch et al. | |
| 8,765,784 B2 | 7/2014 | Arrington et al. | |
| 8,785,438 B2 | 7/2014 | Ohtsuka et al. | |
| 8,877,772 B2 | 11/2014 | Gelbard et al. | |
| 8,987,473 B2 | 3/2015 | Nagai et al. | |
| 9,174,993 B2 | 11/2015 | Nazare et al. | |
| 9,434,743 B2 | 9/2016 | Cheruvallath et al. | |
| 9,963,447 B2 | 5/2018 | Chrovian et al. | |
| 9,981,950 B2 | 5/2018 | Schindler et al. | |
| 10,071,988 B2 | 9/2018 | Chen et al. | |
| 10,155,727 B2 | 12/2018 | Schindler et al. | |
| 10,233,173 B2 | 3/2019 | Chen et al. | |
| 10,323,021 B2 | 6/2019 | Schindler et al. | |
| 10,377,753 B2 | 8/2019 | Chrovian et al. | |
| 10,617,676 B2 | 4/2020 | Chrovian et al. | |
| 10,766,880 B2 | 9/2020 | Chen et al. | |
| 11,008,302 B2 | 5/2021 | Ziff et al. | |
| 11,161,846 B2 | 11/2021 | Hiscox et al. | |
| 11,207,298 B2 | 12/2021 | Chrovian et al. | |
| 11,214,563 B2 * | 1/2022 | Dvorak | A61P 25/18 |
| 11,447,503 B2 | 9/2022 | Gelin et al. | |
| 11,459,336 B2 | 10/2022 | Gelin et al. | |
| 2005/0070542 A1 | 3/2005 | Hodgetts et al. | |
| 2007/0275965 A1 | 11/2007 | Thomas et al. | |
| 2008/0300239 A1 | 12/2008 | Adams et al. | |
| 2011/0130384 A1 | 6/2011 | Setoh et al. | |
| 2014/0275011 A1 | 9/2014 | Mastracchio et al. | |
| 2015/0210681 A1 | 7/2015 | Bourque et al. | |
| 2016/0024087 A1 | 1/2016 | Gelbard et al. | |
| 2018/0125826 A1 | 5/2018 | Chrovian et al. | |
| 2018/0282305 A1 | 5/2018 | Chrovian et al. | |
| 2018/0208595 A1 | 7/2018 | Chrovian et al. | |
| 2018/0334451 A1 | 11/2018 | Chen et al. | |
| 2019/0135791 A1 | 5/2019 | Chen et al. | |
| 2019/0308950 A1 | 10/2019 | Ziff et al. | |
| 2020/0392113 A1 | 12/2020 | Dvorak et al. | |
| 2020/0392130 A1 | 12/2020 | Hiscox et al. | |
| 2020/0392154 A1 | 12/2020 | Gelin et al. | |

(Continued)

FOREIGN PATENT DOCUMENTS

CN 110294756 A 10/2019
EP 928789 A1 7/1999

(Continued)

OTHER PUBLICATIONS

Unofficial English translation of the Office Action issued Nov. 29, 2023 in Russian application No. 2022100440.
Chemical encyclopedic dictionary. Ed. by I. L. Knunyants. Moscow, Soviet Encyclopedia, 1983, pp. 130-131.
"Rukovodstvo po provedeniyu doklinicheskih issledovanij lekarstvennyh sredstv", Part 1. Moscow: "Grif i K", 2012, p. 944, Ed. by Mironov A. N.
Kümmerer., 2010, "Pharmaceuticals in the environment," Annual Review of Environment and Resources 35:57-75 (abstract).
Mony et al., 2011, "Molecular basis of positive allosteric modulation of GluN2B NMDA receptors by polyamines" EMBO 30(15):3134-3146.

(Continued)

*Primary Examiner* — Timothy R Rozof
(74) *Attorney, Agent, or Firm* — Biospark Intellectual Property Law

(57) ABSTRACT

Substituted PYRAZOLO-PYRAZINES as GluN2B receptor ligands. Such compounds may be used in GluN2B receptor modulation and in pharmaceutical compositions and methods for the treatment of disease states, disorders, and conditions mediated by GluN2B receptor activity.

19 Claims, No Drawings

(56) References Cited

U.S. PATENT DOCUMENTS

| | | |
|---|---|---|
| 2020/0392155 A1 | 12/2020 | Gelin |
| 2021/0017168 A1 | 1/2021 | Hiscox et al. |
| 2021/0017169 A1 | 1/2021 | Hiscox et al. |
| 2021/0340121 A1 | 11/2021 | Ziff et al. |
| 2022/0324860 A1 | 10/2022 | Hiscox et al. |
| 2023/0000833 A1 | 1/2023 | Chrovian et al. |

FOREIGN PATENT DOCUMENTS

| | | |
|---|---|---|
| EP | 2194045 A1 | 6/2010 |
| JP | 2004-501901 A1 | 1/2004 |
| JP | 2012-188363 A | 4/2012 |
| KR | 20100057433 A | 5/2010 |
| WO | 1991018897 A1 | 12/1991 |
| WO | 1995028400 A1 | 10/1995 |
| WO | 2002060877 A1 | 8/2002 |
| WO | 2003082868 A1 | 10/2003 |
| WO | 2003097637 A1 | 11/2003 |
| WO | 2003/101968 A1 | 12/2003 |
| WO | 2005080379 A1 | 9/2005 |
| WO | 2008145616 A1 | 12/2008 |
| WO | 2009004430 A1 | 1/2009 |
| WO | 2009058261 A1 | 5/2009 |
| WO | 2009118187 A1 | 10/2009 |
| WO | 2009157196 A1 | 12/2009 |
| WO | 2010043396 A1 | 4/2010 |
| WO | 2010108187 A1 | 9/2010 |
| WO | 2011022348 A1 | 2/2011 |
| WO | 2011140202 A2 | 11/2011 |
| WO | 2013016488 A1 | 1/2013 |
| WO | 2013060029 A1 | 5/2013 |
| WO | 2013130855 A1 | 9/2013 |
| WO | 2014120800 A1 | 8/2014 |
| WO | 2014124651 A1 | 8/2014 |
| WO | 2014145051 A1 | 9/2014 |
| WO | 2015002754 A2 | 1/2015 |
| WO | 2015017502 A1 | 2/2015 |
| WO | 2016/025918 A1 | 2/2016 |
| WO | 2016025917 A1 | 2/2016 |
| WO | 2016081649 A1 | 5/2016 |
| WO | 2016150971 A1 | 9/2016 |
| WO | 2017/007938 | 1/2017 |
| WO | 2018/067786 | 4/2018 |
| WO | 2018231745 A1 | 12/2018 |
| WO | 2019/121885 A1 | 6/2019 |
| WO | 2020/249731 A1 | 12/2020 |
| WO | 2020/249785 A1 | 12/2020 |
| WO | 2020/249791 A1 | 12/2020 |
| WO | 2020/249792 A1 | 12/2020 |
| WO | 2020/249796 A1 | 12/2020 |
| WO | 2020/249799 A1 | 12/2020 |
| WO | 2020/249802 A1 | 12/2020 |
| WO | 2021/005586 A1 | 1/2021 |
| WO | 2021/250521 A1 | 12/2021 |

OTHER PUBLICATIONS

Zhang et al., 2014, "Discovery and preclinical characterization of 1-methyl-3-(4-methylpyridin-3-yl)-6-(pyridin-2-ylmethoxy)-1H-pyrazolo-[3, 4-b] pyrazine (PF470): a highly potent, selective, and efficacious metabotropic glutamate receptor 5 (mGluR5) negative allosteric modulator" Journal of Medicinal Chemistry 57(3):861-877 (abstract).

Addy et al., 2009, "Single-Dc3e Administration of MK-0657, an N112B-Selective NMDA Antagonist, Does Not Result in Clinically Meaningful Improvement in Motor Function in Patients 127ith Moderate Parkinson's Disease," Journal of Clinical Pharmacology (49):856-864.

Arnold et al., 2009, "Glutamate receptor gene (GRIN2B) associated with reduced anterior cingulate glutamatergic concentration in pediatric obsessive-compulsive disorder," Psychiatry Research: Neuroimaging 172(2):136-139.

Bagshawe, 1995, "Antibody-Directed Enzyme prodrug Therapy: A Review," Drug Development Research 34:220-230.

Berberich et al., 2007, "The role of NMDAR subtypes and charge transfer during hippocampal LTP induction," Neuropharmacology 52(1):77-86.

Berge et al., 1997, "Pharmaceutical Salts," Journal of Pharmaceutical Sciences 66(1):1-19.

Bertolini et al., 1997, "A New Rational Hypothesis for the Pharmacophore of the Active Metabolite of Leflunomide, a Potent Immunosuppressive Drug," Journal of Medicinal Chemistry 40(13):2011-2016.

Bodor, 1984, "Novel Approaches to the Design of Safer Drugs: Soft Drugs and Site-Specific Chemical Delivery Systems," Advances in Drug Research 13:256-331.

Bullock et al., 1997, "An Open-Label Study of CP-101,606 in Subjects with a Severe Traumatic Head Injury or Spontaneous Intracerebral Hemorrhage," Annals New York Academy of Sciences 890:51-58.

Buonarati et al., 1990, "Role of sulfation and acetylation in the activation of 2-hydroxyamino-1-methyl-6-phenylimidazo[4,5-b]pyridine to intermediates which bind DNA," Mutation Research 245:185-190.

Chattopadhyay et al., 2010, "Fused Tetrazoles as Azide Surrogates in Click Reaction: Efficient Synthesis of N-Heterocycle-Substituted 1,2,3-Triazoles," Organic Letters 12(9):2166-2169.

Chrovian et al., 2019, "1H-Pyrrolo[3,2-b]pyridine GluN2B-Selective Negative Allosteric Modulators", ACS Med. Chem. Lett 10:261-266.

Chemical Abstract Service (CAS), Database Registry [Online], Database Registry [Online], STN Sep. 18, 2012, pp. 1-1, Database Accession No. 1394745_67_5.

Collingridge et al., 2009, "A nomenclature for ligand-gated ion channels," Neuropharmacology 56:2-5.

Communication pursuant to Article 94(3) EPC dated Sep. 13, 2021 in connection with EP application No. 17 859 165.7.

Cull-Candy et al., 2011, "NMDA receptor subunits: diversity, development and disease," Current Opinion in Neurobiology 11(3):327-335.

Considine, 2005, Van Nostrand's Encyclopedia of Chemistry, Encyclopedia of Chemistry, Chapter 5, pp. 261.

Dalmau et al., 2008, "Anti-NMDA-receptor encephalitis: case series and analysis of the effects of antibodies," Lancet Neurol 7(12):1091-1098.

Davies et al., 2012, "A novel series of benzimidazole NR2B-selective NMDA receptor antagonists," Bioorganic & Medicinal Chemistry Letters 22:2620-2623.

Dorval et al., 2007, "Association of the glutamate receptor subunit gene GRIN2B with attention-deficit/hyperactivity disorder," Genes, Brain and Behavior 6(5):444-452.

Duty, 2012, "Targeting Glutamate Receptors to Tackle the Pathogenesis, Clinical Symptoms and Levodopa-Induced Dyskinesia Associated with Parkinson's Disease," CNS Drugs, 26(12):1017-1032.

Farjam et al., 2014, "Inhibition of NR2B-Containing N-methyl-D-Aspartate Receptors (NMDARs) in Experimental Autoimmune Encephalomyelitis, a Model of Multiple Sclerosis," Iranian Journal of Pharmaceutical Research 13(2):695-705.

First Examination Report issued Nov. 30, 2020 in connection with European application No. 17859165.7.

Fleisher et al., 1996, "Improved oral drug delivery: solubility limitations overcome by the use of prodrugs," Advanced Drug Delivery Reviews 19:115-130.

Fuller et al., 2006, "Differential expression of the NMDA NR2B receptor subunit in motoneuron populations susceptible and resistant to amyotrophic lateral sclerosis," Neuroscience Letters 399(1-2):157-161.

Grasselli et al., 2013, "Abnormal NMDA receptor function exacerbates experimental autoimmune encephalomyelitis," British Journal of Pharmacology 168(2):502-517.

Grimwood et al., 1999, "NR2B-containing NMDA receptors are upregulated in temporal cortex in schizophrenia," NeuroReport 10(3):461-465.

(56) References Cited

OTHER PUBLICATIONS

Guitton et al., 2007, "Blockade of Cochlear NMDA Receptors Prevents Long-Term Tinnitus during a Brief Consolidation Window after Acoustic Trauma," Neural Plasticity Article ID 80904, pp. 1-11.

Haller et al., 2011, "NR2B subunit-specific NMDA antagonist Ro25-6981 inhibits the expression of conditioned fear: a comparison with the NMDA antagonist MK-801 and fluoxetine," Behavioural Pharmacology 22(2):113-121.

Hanson et al., 2015, "Altered GluN2B NMDA receptor function and synaptic plasticity during early pathology in the PS2APP mouse model of Alzheimer's disease," Neurobiology of Disease 74:254-262.

Hu et al., 2016, "Expression of immediate-early genes in the dorsal cochlear nucleus in salicylate-induced tinnitus," Eur Arch Otorhinolaryngol 273(2):325-332.

Houston et al., 2008 "Methods for Predicting In Vivo Pharmacokinetics Using Data from In Vitro Assays," Current Drug Metabolism 9:940-951.

Iadarola et al., 2015, Therapeutic Advances in Chronic Disease 6(3):97-114.

International Search Report and Written Opinion of the International Searching Authority for International Application No. PCT/US2015/045412, dated Nov. 10, 2015.

International Search Report and Written Opinion of the International Searching Authority for International Application No. PCT/US2015/045413, dated Nov. 27, 2015.

International Search Report and Written Opinion of the International Searching Authority for International Application No. PCT/US2016/041339 mailed Sep. 27, 2016.

International Search Report and Written Opinion of the International Searching Authority for International Application No. PCT/US2017/017093, dated Apr. 7, 2017.

International Search Report and Written Opinion of the International Searching Authority issued in connection with PCT/US2017/055278, mailed Mar. 9, 2018.

International Search Report and Written Opinion of the International Searching Authority for International Application No. PCT/IB2019/052731, dated Nov. 1, 2019.

International Search Report and Written Opinion of the International Searching Authority for International Application No. PCT/EP2020/066384, dated Jul. 28, 2020.

International Search Report and Written Opinion of the International Searching Authority for International Application No. PCT/EP2020/066400, dated Jul. 28, 2020.

International Search Report and Written Opinion of the International Searching Authority for International Application No. PCT/EP2020/066396, dated Jul. 29, 2020.

International Search Report and Written Opinion of the International Searching Authority for International Application No. PCT/EP2020/066391, dated Jul. 29, 2020.

International Search Report and Written Opinion of the International Searching Authority for International Application No. PCT/EP2020/066405, dated Jul. 29, 2020.

International Search Report and Written Opinion of the International Searching Authority for International Application No. PCT/EP2020/066392, dated Sep. 21, 2020.

Ito et al., 2003, "A Medium-term rat liver bioassay for rapid in vivo detection of carcinogenic potential of chemicals," Cancer Sci 94(1):3-8.

Kolb et al., 2001, "Click Chemistry: Diverse Chemical Function from a Few Good Reactions," Angew. Chem. Int. Ed 40:2004-2021.

Kowal et al., 2006, "Human lupus autoantibodies against NMDA receptors mediate cognitive impairment," PNAS 103(52):19854-19859.

Layton et al., 2006 "Recent Advances in the Development of NR2B Subtype-Selective NMDA Receptor Antagonist" Current Topics in Medicinal Chemistry, 6:697-709.

Layton et al., 2016, "Discovery of 5-aryl-1,3-dihydro-2H-imidazo[4,5-b]pyridin-2-ones as positive allosteric modulators of metabotropic glutamate subtype-2(mGlu2) receptors with efficacy in a preclinical model of psychosis," Bioorganic & Medicinal Chemistry Letters 26:1260-1264.

Leaderbrand et al., 2014, "Co-activation of NR2A and NR2B subunits induces resistance to fear extinction," Neurobiol Learn Mem 113:35-40.

Leaver et al., 2008, "Neuroprotective effects of a selective N-methyl-d-aspartate NR2B receptor antagonist in the 6-hydroxydopamine rat model of Parkinson's disease," Clinical and Experimental Pharmacology and Physiology 35(11):1388-1394.

Leyva et al., 1989, "Photochemistry of Fluorinated Aryl Azides in Toluene Solution and in Frozen Polycrystals," J. Org. Chem 54(25):5938-5945.

Li et al., 2004, "Enhanced Striatal NR2B-Containing N-Methyl-D-Aspartate Receptor-Mediated Synaptic Currents in a Mouse Model of Huntington Disease," J Neurophysiol 92(5):2738-2746.

Li et al., 2011, "Glutamate N-methyl-D-aspartate Receptor Antagonists Rapidly Reverse Behavioral and Synaptic Deficits Caused by Chronic Stress Exposure," Biol Psychiatry 69(8):754-761.

Li et al., 2011, "Soluble Ab Oligomers Inhibit Long-Term Potentiation through a Mechanism Involving Excessive Activation of Extrasynaptic NR2B-Containing NMDA Receptors," The Journal of Neuroscience 31(18):6627-6638.

Lima-Ojeda et al., 2013, "Pharmacological blockade of GluN2B-containing NMDA receptors induces antidepressant-like effects lacking psychotomimetic action and neurotoxicity in the perinatal and adult rodent brain," Progress in Neuro-Psychopharmacology & Biological Psychiatry 45:28-33.

Machado-Vieira et al., 2017, "New Targets for Rapid Antidepressant Action," Prog. Neurobiol. 152:21-37.

Mao et al., 2014, "Phosphorylation and regulation of glutamate receptors by CaMKII," Acta Physiologica Sinica 66(3):365-372.

Martucci et al., 2006, "N-methyl-d-aspartate receptor NR2B subunit gene GRIN2B in schizophrenia and bipolar disorder: Polymorphisms and mRNA levels," Schizophrenia Research 84(2-3):214-221.

Massey et al., 2004, "Differential Roles of NR2A and NR2B-Containing NMDA Receptors in Cortical Long-Term Potentiation and Long-Term Depression," The Journal of Neuroscience 24(36):7821-7828.

Miller et al., 2014, "GluN2B-containing NMDA receptors regulate depression-like behavior and are critical for the rapid antidepressant actions of ketamine," eLife 3:1-22.

Morissette et al., 2006, "Prevention of Levodopa-Induced Dyskinesias by a Selective NR1A/2B N-Methyl-D-aspartate Receptor Antagonist in Parkinsonian Monkeys: Implication of Preproenkephalin," Movement Disorders 21(1):9-17.

Nagy, 2004, "The NR2B Subtype of NMDA Receptor: A Potential Target for the Treatment of Alcohol Dependence, Current Drug Targets," CNS & Neurological Disorders 3(3):169-179.

Naskar et al., 1999, "Saving the Nerve from Glaucoma: Memantine to Caspaces," Seminars in Ophthalmology 14(3):152-158.

Naspolini et al., 2012, "Traxoprodil decreases pentylenetetrazol-induced seizures," Epilepsy Research 100(1-2):12-19.

Nutt et al., 2008, "Effects of a NR2B Selective NMDA Glutamate Antagonist, CP-101,606, on Dyskinesia and Parkinsonism," Movement Disorders 23(13):1860-1866.

Orgogozo et al., 2002, "Efficacy and Safety of Memantine in Patients With Mild to Moderate Vascular Dementia A Randomized, Placebo-Controlled Trial (MMM 300)," Stroke 33: 1834-1839.

Paoletti et al., 2013, "NMDA receptor subunit diversity: impact on receptor properties, synaptic plasticity and disease," Nat Rev Neurosci. 14(6):383-400.

Park et al. 2001, "Metabolism of Fluorine-containing drugs", Annu. Rev. Pharmacol. Toxicol. 41:443-470.

Paulekuhn et al., 2007, "Trends in Active Pharmaceutical Ingredient Salt Selection based on Analysis of the Orange Book Database," Journal of Medicinal Chemistry 50(26):6665-6672.

Peeters et al., 2007, "Effects of Pan- and Subtype-Selective N-Methyl-D-aspartate Receptor Antagonists on Cortical Spreading Depression in the Rat: Therapeutic Potential for Migraine," The Journal of Pharmacology and Experimental Therapeutics 321(2):564-572.

(56) References Cited

OTHER PUBLICATIONS

Porsolt et al., 1997, "Behavioural Despair in Mice: A Primary Screening Test for Antidepressants," Arch int Pharmacodyn 229:327-336.
Pratap et al., 2007 "Guanidine and amidine mediated synthesis of bridgehead triazaphenalenes, pyrimidines and pyridines through domino reactions" Tetrahedron Letters 48:5845-5849.
Preskorn et al., 2008, "An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder," Journal of Clinical Psychopharmacology 28(6): 631-637.
PubChem-CID-90046926, Create Date: Feb. 13, 2015 (Feb. 13, 2015).
Remington, 1985, Remington Pharmaceutical Sciences., Pharmaceutical Sciences., pp. 1418, vol. 76.
Robinson et al., 1996, "Discovery of the Hemifumarate and (r-L-Alanyloxy)methyl Ether as Prodrugs of an Antirheumatic Oxindole: Prodrugs for the Enolic OH Group," Journal of Medicinal Chemistry 39(1):10-18.
Ruppa et al., 2012, "Chapter 7: NMDA Antagonists of GluN2B Subtype and Modulators of GluN2A, GluN2C, and GluN2D Subtypes-Recent Results and Developments," Annual Reports in Medicinal Chemistry 47:89-103.
Shan et al., 1997, "Prodrug Strategies Based on Intramolecular Cyclization Reactions," Journal of Pharmaceutical Sciences 86(7):765-767.
Shen et al., 2011, "Heroin relapse requires long-term potentiation-like plasticity mediated by NMDA2b-containing receptors," PNAS 108(48):19407-19412.
Starck et al., 1997, "Drug therapy for acquired pendular nystagmus in multiple sclerosis," J Neurol 244(1):9-16.
Steece-Collier et al., 2000, "Antiparkinsonian Actions of CP-101,606, an Antagonist of NR2B Subunit-Containing N-Methyl-D-Aspartate Receptors," Experimental Neurology, vol. 163, Issue 1, pp. 239-243.
STN Registry database entry for CAS RN 1394745-67-5, entered STN Sep. 18, 2012, Accessed Sep. 8, 2017.
STN Registry database entry for CAS RN 1493474-46-6, 1491341-24-2, 1479235-62-5, and 1477636-42-2, Accessed Apr. 10, 2019.
Straube, 2005, "Pharmacology of vertigo/nystagmus/oscillopsia," Current Opinion in Neurology 18:11-14.
Sun et al., 2020, "Synthesis and preliminary evaluation of novel C-labled GluN2B-selective NMDA receptor negative allosteric modulators," Acta Pharmacologica Sinica 0:1-8.
Supplementary European Search Report issued Jan. 12, 2022 in connection with European application No. 19782400.6.
Tang et al., 2005, "Disturbed Ca2+ signaling and apoptosis of medium spiny neurons in Huntington's disease," PNAS 102(7):2602-2607.
Tang et al., 1999, "Genetic enchancement of learning and memory in mice," Nature 401(6748):63-69.
Traynelis et al., 2010, "Glutamate Receptor Ion Channels: Structure, Regulation, and Function," Pharmacol Rev 62(3):405-496.
Vippagunta et al., 2001, "Crystalline Solids," Advanced Drug Delivery Reviews 48(1):3-26.
Wang et al., 2014, "Targeting the NMDA receptor subunit NR2B for treating or preventing age-related memory decline," Expert Opin. Ther. Targets 18(10):1121-1130.
Watanabe et al., 1993, "Distinct Distributions of Five N-Methyl-D-Aspartate Receptor Channel Subunit mRNAs in the Forebrain," The Journal of Comparative Neurology 338(3):377-390.
Weickert et al., 2013, "Molecular evidence of N-methyl-D-aspartate receptor hypofunction in schizophrenia," Molecular Psychiatry 18:1185-1192.
Won et al., 2012, "Autistic-like social behaviour in Shank2-mutant mice improved by restoringNMDA receptor function," Nature 486:261-265.
Wu and Zhuo, 2009, "Targeting the NMDA Receptor Subunit NR2B for the Treatment of Neuropathic Pain," Neurotherapeutics 6(4):693-702.
Yang et al., 2003, "Reduced brain infarct volume and improved neurological outcome by inhibition of the NR2B subunit of NMDA receptors by using CP101,606-27 alone and in combination with rt-PA in a thromboembolic stroke model in rats," J. Neurosurg 98(2):397-403.
Youssif, 2001, "Recent trends in the chemistry of pyridine N-oxides," ARKIVOC 1:242-268.
Yuan et al., 2015, "Context-Dependent GluN2B-Selective Inhibitors of NMDA Receptor Function Are Neuroprotective with Minimal Side Effects," Neuron 85(6):1305-1318.
Zarate et al., 2006, "A Randomized Trail of an N-methyl_D-aspartate Antagonist in Treatment-Resistant Major Depression," Arch Gen Psychiatry 63:856-864.

* cited by examiner

SUBSTITUTED PYRAZOLO-PYRAZINES AND THEIR USE AS GluN2B RECEPTOR MODULATORS

CROSS-REFERENCE TO RELATED APPLICATIONS

This application claims the priority benefit of U.S. provisional application No. 62/861,681, filed Jun. 14, 2019, the contents of which are incorporated herein in their entireties by reference thereto.

FIELD OF THE INVENTION

The present invention is related to compounds having GluN2B modulating properties, pharmaceutical compositions comprising these compounds, chemical processes for preparing these compounds and their use in the treatment of diseases associated with GluN2B receptor activity in animals, in particular humans.

BACKGROUND OF THE INVENTION

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., *Pharmacol Rev.* 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., *Neuropharmacology* 2007; 52(1):77-86) and long-term depression (LTD) (Massey, P V et al., *J Neurosci.* 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluNR2 subunits play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., *Nat Rev Neurosci.* 2013; 14(6):383-400; Watanabe M et al., *J Comp Neurol.* 1993; 338(3):377-90) and are implicated in learning, memory processing, mood, attention, emotion and pain perception (Cull-Candy S et al., *Curr Opin Neurobiol.* 2001; 11(3):327-35).

Compounds that modulate GluN2B-containing NMDA receptor function can be useful in treatment of many neurological and psychiatric disorders including but not limited to bipolar disorder (Martucci L et al., *Schizophrenia Res,* 2006; 84(2-3):214-21), major depressive disorder (Miller O H et al., *eLife.* 2014; 3:e03581; Li N et al., *Biol Psychiatry.* 2011; 69(8):754-61), treatment-resistant depression (Preskorn S H et al. *J Cin Psychopharmacol.* 2008; 28(6): 631-7) and their mood disorders (including schizophrenia (Grimwood S et al., *Neuroreport.* 1999; 10(3):461-5; Weickert C S et al. *Molecular Psychiatry* (2013) 18, 1185-1192), ante- and postpartum depression, seasonal affective disorder and the like), Alzheimer's disease (Hanson J E et al., *Neurobiol Dis.* 2015; 74:254-62; Li S et al., *J Neurosci.* 2011; 31(18):6627-38) and other dementias (Orgogozo J M et al. Stroke 2002, 33: 1834-1839), Parkinson's disease (Duty S, *CNS Drugs.* 2012; 26(12):1017-32; Steece-Collier K et al., *Exp Neurol.* 2000; 163(1):239-43; Leaver K R et al. *Cin Exp Pharmacol Physiol.* 2008; 35(11):1388-94), Huntington's chorea (Tang T S et al., *Proc Natl Acad Sci USA.* 2005; 102(7):2602-7; Li L et al., *J Neurophysiol.* 2004; 92(5):2738-46), multiple sclerosis (Grasselli G et al., *Br J Pharmacol.* 2013; 168(2):502-17; Farjam M et al., *Iran J Pharm Res.* 2014; 13(2):695-705), cognitive impairment (Wang D et al. 2014, *Expert Opin Ther Targets Expert Opin Ther Targets.* 2014; 18(10):1121-30), head injury (Bullock M R et al., *Ann N Y Acad Sci.* 1999; 890:51-8), spinal cord injury, stroke (Yang Y et al., *J Neurosurg.* 2003; 98(2):397-403), epilepsy (Naspolini A P et al., *Epilepsy Res.* 2012 June; 100(1-2):12-9), movement disorders (e.g. dyskinesias) (Morissette M et al., *Mov Disord.* 2006; 21(1):9-17), various neurodegenerative diseases (e.g. amyotrophic lateral sclerosis (Fuller P I et al., *Neurosci Lett.* 2006; 399(1-2):157-61) or neurodegeneration associated with bacterial or chronic infections), glaucoma (Naskar R et al. *Semin Ophthalmol.* 1999 September; 14(3):152-8), pain (e.g. chronic, cancer, post-operative and neuropathic pain (Wu L J and Zhuo M, *Neurotherapeutics.* 2009; 6(4):693-702), diabetic neuropathy, migraine (Peeters M et al., *J Pharmacol Exp Ther.* 2007; 321(2):564-72), cerebral ischemia (Yuan H et al., *Neuron.* 2015; 85(6):1305-18), encephalitis (Dalmau J. et al., *Lancet Neurol.* 2008; 7(12):1091-8), autism and autism spectrum disorders (Won H. et al., *Nature.* 2012; 486(7402):261-5), memory and learning disorders (Tang, Y. P. et al., *Nature.* 1999; 401(6748):63-9), obsessive compulsive disorder (Arnold P D et al., *Psychiatry Res.* 2009; 172(2):136-9), attention deficit hyperactivity disorder (ADHD) (Dorval K M et al., *Genes Brain Behav.* 2007; 6(5):444-52), PTSD (Haller J et al. *Behav Pharmacol.* 2011; 22(2):113-21; Leaderbrand K et al. *Neurobiol Learn Mem.* 2014; 113:35-40), tinnitus (Guitton M J, and Dudai Y, *Neural Plast.* 2007; 80904; Hu S S et al. 2016; 273(2): 325-332), sleep disorders (like narcolepsy or excessive daytime sleepiness, patent WO 2009058261 A1), vertigo and nystagmus (Straube A. et al., *Curr Opin Neurol.* 2005; 18(1):11-4; Starck M et al. *J Neurol.* 1997 January; 244(1):9-16), anxiety autoimmunological disorders like neuropsychiatric systemic lupus erythematosus (Kowal C et al. *Proc. Natl. Acad. Sci. U.S.A.* 2006; 103, 19854-19859) and addictive illnesses (e.g. alcohol addiction, drug addiction) (Nagy J, 2004, *Curr Drug*

Targets CNS Neurol Disord 2004; 3(3):169-79; Shen H et al., *Proc Natl Acad Sci USA*. 2011; 108(48):19407-12).

In view of the clinical importance of GluN2B, the identification of compounds that modulate GluN2B receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

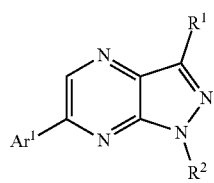
(I)

wherein
$R^1$ is H or halo;
$Ar^1$ is selected from the group consisting of:
(a) phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl; and
(b) thienyl substituted with $CF_3$; and
$R^2$ is selected from the group consisting of:
(c)

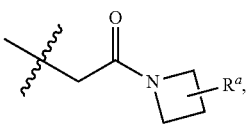

wherein $R^a$ is selected from the group consisting of: H, halo, and $C_{1-6}$alkyl;

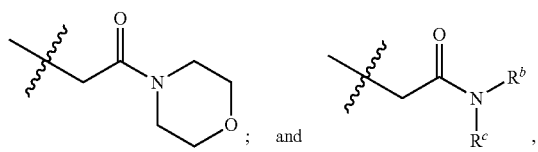

wherein $R^b$ is $C_{1-6}$alkyl, and $R^c$ is $C_{1-6}$alkyl;
(d)

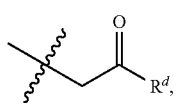

wherein $R^d$ is $C_{1-6}$alkyl, or $C_{3-6}$cycloalkyl; and (e)

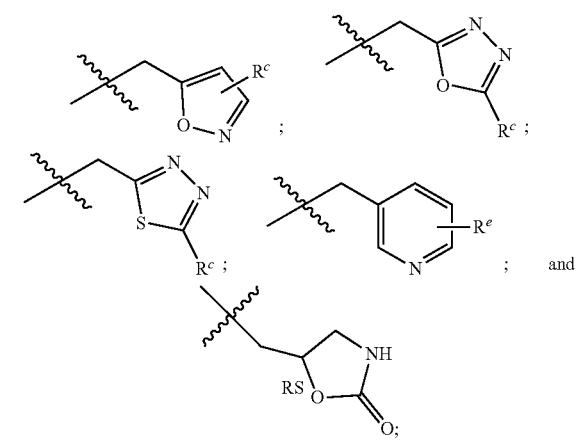

wherein $R^e$ is selected from the group consisting of: halo, $OC_{1-6}$alkyl, and CN; and pharmaceutically acceptable salts, stereoisomers, isotopic variants, N-oxides, or solvates of compounds of Formula (I).

Further embodiments are provided by pharmaceutically acceptable salts of compounds of Formulas (I), pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as the pharmaceutically acceptable salts.

In a further aspect, the invention relates to pharmaceutical compositions for treating a disease, disorder, or medical condition mediated by GluN2B receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as GluN2B receptor modulators. Thus, the invention is directed to a method for modulating GluN2B receptor activity, including when such receptor is in a subject, comprising exposing GluN2B receptor to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by GluN2B receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION

In one aspect, provided herein are compounds of Formula (I), and pharmaceutically acceptable salts, stereoisomers, isotopic variants, N-oxides, or solvates thereof, Formula (I):

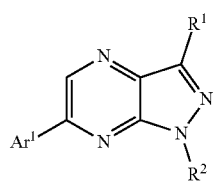

(I)

wherein
$R^1$ is H or halo;
$Ar^1$ is selected from the group consisting of:
(a) phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl; and
(b) thienyl substituted with $CF_3$; and
$R^2$ is selected from the group consisting of:
(c)

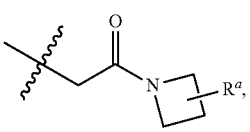

wherein $R^a$ is selected from the group consisting of: H, halo, and $C_{1-6}$alkyl;

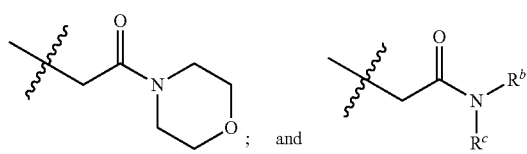

wherein $R^b$ is $C_{1-6}$alkyl, and $R^c$ is $C_{1-6}$alkyl;

(d)

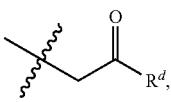

wherein $R^d$ is $C_{1-6}$alkyl, or $C_{3-6}$cycloalkyl; and
(e)

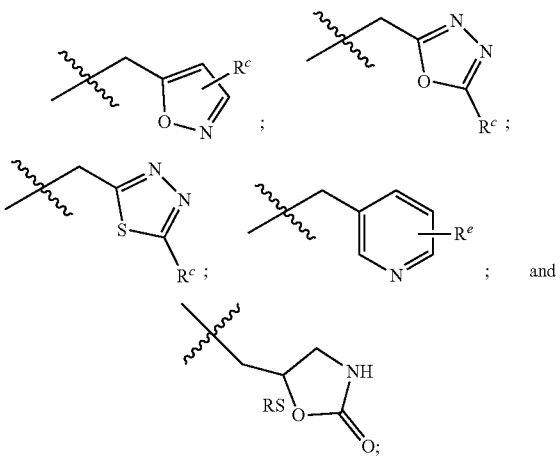

wherein $R^e$ is selected from the group consisting of: halo, $OC_{1-6}$alkyl, and CN.

An additional embodiment of the invention is a compound of Formula (I) wherein

An additional embodiment of the invention is a compound of Formula (I) wherein $R^1$ is H.

An additional embodiment of the invention is a compound of Formula (I) wherein $R^1$ is F.

An additional embodiment of the invention is a compound of Formula (I) wherein $Ar^1$ is phenyl substituted one $CH_3$, $OCF_3$, or $CF_2CH_3$ member.

An additional embodiment of the invention is a compound of Formula (I) wherein $Ar^1$ is phenyl substituted with two members each independently selected from the group consisting of: Cl, F, $CH_3$, $CHF_2$, $CF_3$, $CHF_2CH_3$, $OCH_3$, and $OCHF_2$.

An additional embodiment of the invention is a compound of Formula (I) wherein $Ar^1$ is

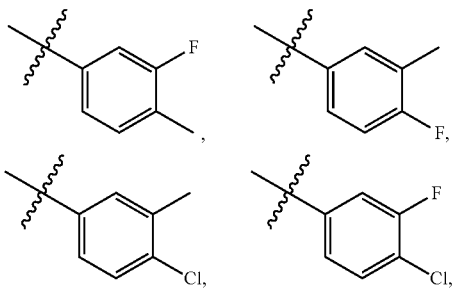

An additional embodiment of the invention is a compound of Formula (I) wherein $Ar^1$ is phenyl substituted with three members each independently selected from the group consisting of: halo, and $CH_3$.

An additional embodiment of the invention is a compound of Formula (I) wherein $Ar^1$ is An additional embodiment of the invention is a compound of Formula (I) wherein $Ar^1$ is An additional embodiment of the invention is a compound of Formula (I) wherein $R^2$ is wherein
$R^a$ is selected from the group consisting of: H, F, and $CH_3$.

An additional embodiment of the invention is a compound of Formula (I) wherein $R^2$ is An additional embodiment of the invention is a compound of Formula (I) wherein $R^2$ is An additional embodiment of the invention is a compound of Formula (I) wherein $R^2$ is An additional embodiment of the invention is a compound of Formula (I) wherein $R^2$ is An additional embodiment of the invention is a compound of Formula (I) wherein $R^2$ is

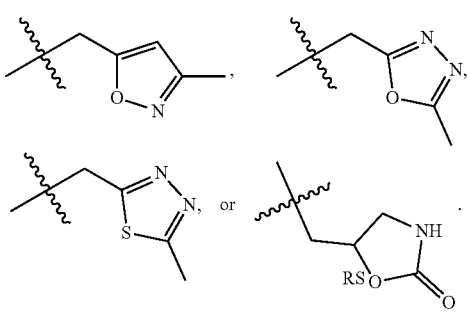

An additional embodiment of the invention is a compound of Formula (I) wherein $R^2$ is

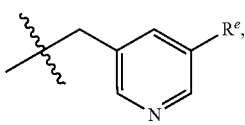

wherein $R^e$ is Cl, F, $OCH_3$, or CN.

An additional embodiment of the invention is a compound of Formula (I), having the structure of Formula (IA):

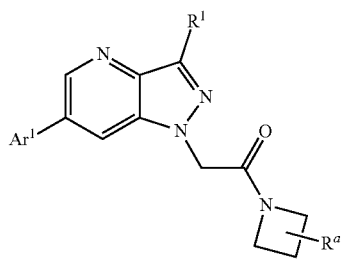

(IA)

wherein $R^1$ is H, or F;

$Ar^1$ is phenyl substituted with two members each independently selected from the group consisting of: halo, $C_{1-6}$alkyl, $C_{1-6}$perhaloalkyl, and $OC_{1-6}$perhaloalkyl; and $R^a$ is H, halo, or $C_{1-6}$alkyl.

An additional embodiment of the invention is a compound of Formula (I), having the structure of Formula (IA), wherein $R^1$ is H.

An additional embodiment of the invention is a compound of Formula (I) having the Formula (IB):

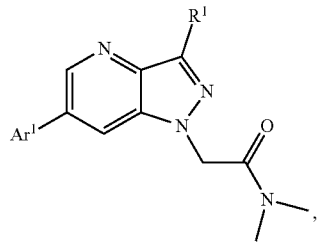

(IB)

wherein $R^1$ is H, or F; and $Ar^1$ is (a) phenyl substituted with two members each independently selected from the group consisting of: halo, $C_{1-6}$alkyl, $C_{1-6}$perhaloalkyl, and $OC_{1-6}$perhaloalkyl; or (b) thienyl substituted with $CF_3$.

An additional embodiment of the invention is a compound of Formula (I), having the structure of Formula (IB), wherein $R^1$ is H.

A further embodiment of the current invention is a compound as shown below in Table 1.

TABLE 1

| Ex # | Compound name |
|---|---|
| 1 | 1-[6-[3-(Difluoromethyl)-4-fluoro-phenyl]pyrazolo[3,4-b]pyrazin-1-yl]butan-2-one; |
| 2 | 2-[6-[4-Chloro-3-(difluoromethoxy)phenyl]pyrazolo[3,4-b]pyrazin-1-yl]-1-cyclopropyl-ethanone; |
| 3 | N,N-Dimethyl-2-[6-[5-(trifluoromethyl)-2-thienyl]pyrazolo[3,4-b]pyrazin-1-yl]acetamide; |
| 4 | N,N-Dimethyl-2-[6-(m-tolyl)pyrazolo[3,4-b]pyrazin-1-yl]acetamide; |
| 5 | 2-[6-(4-Chloro-3-fluoro-phenyl)pyrazolo[3,4-b]pyrazin-1-yl]-N,N-dimethyl-acetamide; |
| 6 | 2-[6-(3-Fluoro-4-methyl-phenyl)pyrazolo[3,4-b]pyrazin-1-yl]-N,N-dimethyl-acetamide; |
| 7 | 2-[6-(4-Fluoro-3-methyl-phenyl)pyrazolo[3,4-b]pyrazin-1-yl]-N,N-dimethyl-acetamide; |
| 8 | 2-[6-(4-Chloro-3-methyl-phenyl)pyrazolo[3,4-b]pyrazin-1-yl]-N,N-dimethyl-acetamide; |
| 9 | 2-[6-(3-Chloro-4-methoxy-phenyl)pyrazolo[3,4-b]pyrazin-1-yl]-N,N-dimethyl-acetamide; |
| 10 | 2-[6-[3-(Difluoromethyl)-4-fluoro-phenyl]pyrazolo[3,4-b]pyrazin-1-yl]-N,N-dimethyl-acetamide; |
| 11 | 2-[6-[3-(Difluoromethyl)-4-fluoro-phenyl]-3-fluoro-pyrazolo[3,4-b]pyrazin-1-yl]-N,N-dimethyl-acetamide; |
| 12 | 2-[6-[4-Chloro-3-(difluoromethyl)phenyl]pyrazolo[3,4-b]pyrazin-1-yl]-N,N-dimethyl-acetamide; |
| 13 | 2-[6-[3-(1,1-Difluoroethyl)-4-fluoro-phenyl]pyrazolo[3,4-b]pyrazin-1-yl]-N,N-dimethyl-acetamide; |

TABLE 1-continued

| Ex # | Compound name |
|---|---|
| 14 | 2-[6-[4-Chloro-3-(1,1-difluoroethyl)phenyl]pyrazolo[3,4-b]pyrazin-1-yl]-N,N-dimethyl-acetamide; |
| 15 | 2-[6-[4-Chloro-3-(trifluoromethyl)phenyl]pyrazolo[3,4-b]pyrazin-1-yl]-N,N-dimethyl-acetamide; |
| 16 | 2-[6-[3-(Difluoromethoxy)-4-fluoro-phenyl]pyrazolo[3,4-b]pyrazin-1-yl]-N,N-dimethyl-acetamide; |
| 17 | 2-[6-[4-(Difluoromethoxy)-3-fluoro-phenyl]pyrazolo[3,4-b]pyrazin-1-yl]-N,N-dimethyl-acetamide; |
| 18 | 2-[6-[4-Chloro-3-(difluoromethoxy)phenyl]pyrazolo[3,4-b]pyrazin-1-yl]-N,N-dimethyl-acetamide; |
| 19 | 2-[6-[3-Chloro-4-(trifluoromethoxy)phenyl]pyrazolo[3,4-b]pyrazin-1-yl]-N,N-dimethyl-acetamide; |
| 20 | 2-[6-(3,5-Difluoro-4-methyl-phenyl)pyrazolo[3,4-b]pyrazin-1-yl]-N,N-dimethyl-acetamide; |
| 21 | 2-[6-(2,4-Difluoro-3-methyl-phenyl)pyrazolo[3,4-b]pyrazin-1-yl]-N,N-dimethyl-acetamide; |
| 22 | N,N-Dimethyl-2-[6-(3,4,5-trifluorophenyl)pyrazolo[3,4-b]pyrazin-1-yl]acetamide; |
| 23 | N,N-Dimethyl-2-[6-(2,3,4-trifluorophenyl)pyrazolo[3,4-b]pyrazin-1-yl]acetamide; |
| 24 | 1-(Azetidin-1-yl)-2-[6-[3-(difluoromethyl)-4-fluoro-phenyl]pyrazolo[3,4-b]pyrazin-1-yl]ethanone; |
| 25 | 1-(Azetidin-1-yl)-2-[6-[3-(difluoromethyl)-4-fluoro-phenyl]-3-fluoro-pyrazolo[3,4-b]pyrazin-1-yl]ethanone; |
| 26 | 1-(Azetidin-1-yl)-2-[6-[4-chloro-3-(1,1-difluoroethyl)phenyl]pyrazolo[3,4-b]pyrazin-1-yl]ethanone; |
| 27 | 1-(Azetidin-1-yl)-2-[6-[3-(1,1-difluoroethyl)-4-fluoro-phenyl]pyrazolo[3,4-b]pyrazin-1-yl]ethanone; |
| 28 | 1-(Azetidin-1-yl)-2-[6-[3-(difluoromethoxy)-4-fluoro-phenyl]pyrazolo[3,4-b]pyrazin-1-yl]ethanone; |
| 29 | 1-(Azetidin-1-yl)-2-[6-[4-chloro-3-(difluoromethoxy)phenyl]pyrazolo[3,4-b]pyrazin-1-yl]ethanone; |
| 30 | 2-[6-[3-(Difluoromethyl)-4-fluoro-phenyl]pyrazolo[3,4-b]pyrazin-1-yl]-1-(3-methylazetidin-1-yl)ethanone; |
| 31 | 2-[6-[3-(Difluoromethyl)-4-fluoro-phenyl]-3-fluoro-pyrazolo[3,4-b]pyrazin-1-yl]-1-(3-methylazetidin-1-yl)ethanone; |
| 32 | 2-[6-[3-(Difluoromethyl)-4-fluoro-phenyl]pyrazolo[3,4-b]pyrazin-1-yl]-1-(3-fluoroazetidin-1-yl)ethanone; |
| 33 | 2-[6-[3-(Difluoromethyl)-4-fluoro-phenyl]-3-fluoro-pyrazolo[3,4-b]pyrazin-1-yl]-1-(3-fluoroazetidin-1-yl)ethanone; |
| 34 | 2-[6-[4-Chloro-3-(1,1-difluoroethyl)phenyl]pyrazolo[3,4-b]pyrazin-1-yl]-1-(3-methylazetidin-1-yl)ethanone; |
| 35 | 2-[6-[4-Chloro-3-(1,1-difluoroethyl)phenyl]pyrazolo[3,4-b]pyrazin-1-yl]-1-(3-fluoroazetidin-1-yl)ethanone; |
| 36 | 2-[6-[3-(Difluoromethoxy)-4-fluoro-phenyl]pyrazolo[3,4-b]pyrazin-1-yl]-1-(3-methylazetidin-1-yl)ethanone; |
| 37 | 2-[6-[3-(Difluoromethoxy)-4-fluoro-phenyl]pyrazolo[3,4-b]pyrazin-1-yl]-1-(3-fluoroazetidin-1-yl)ethanone; |
| 38 | 2-[6-[4-Chloro-3-(1,1-difluoroethyl)phenyl]pyrazolo[3,4-b]pyrazin-1-yl]-1-morpholino-ethanone; |
| 39 | 2-[[6-[3-(Difluoromethyl)-4-fluoro-phenyl]pyrazolo[3,4-b]pyrazin-1-yl]methyl]-5-methyl-1,3,4-thiadiazole; |
| 40 | 2-[[6-[3-(Difluoromethyl)-4-fluoro-phenyl]pyrazolo[3,4-b]pyrazin-1-yl]methyl]-5-methyl-1,3,4-oxadiazole; |
| 41 | 5-[[6-[3-(Difluoromethyl)-4-fluoro-phenyl]pyrazolo[3,4-b]pyrazin-1-yl]methyl]-3-methyl-isoxazole; |
| 42 | 6-[3-(Difluoromethyl)-4-fluoro-phenyl]-1-[(5-fluoro-3-pyridyl)methyl]pyrazolo[3,4-b]pyrazine; |
| 43 | 1-[(5-Chloro-3-pyridyl)methyl]-6-[3-(difluoromethyl)-4-fluoro-phenyl]pyrazolo[3,4-b]pyrazine; |
| 44 | 6-[3-(Difluoromethyl)-4-fluoro-phenyl]-1-[(5-methoxy-3-pyridyl)methyl]pyrazolo[3,4-b]pyrazine; |
| 45 | 5-[[6-[3-(Difluoromethyl)-4-fluoro-phenyl]pyrazolo[3,4-b]pyrazin-1-yl]methyl]pyridine-3-carbonitrile; |
| 46 | 5-[[6-[3-(Difluoromethyl)-4-fluoro-phenyl]-3-fluoro-pyrazolo[3,4-b]pyrazin-1-yl]methyl]pyridine-3-carbonitrile; |
| 47 | 1-[(5-Chloro-3-pyridyl)methyl]-6-[3-(difluoromethoxy)-4-fluoro-phenyl]pyrazolo[3,4-b]pyrazine; |
| 48 | 2-(6-(4-Chloro-2-fluorophenyl)-1H-pyrazolo[3,4-b]pyrazin-1-yl)-N,N-dimethylacetamide; |
| 49 | N,N-Dimethyl-2-(6-(4-(trifluoromethoxy)phenyl)-1H-pyrazolo[3,4-b]pyrazin-1-yl)acetamide; |
| 50 | 2-(6-(2,5-Difluorophenyl)-1H-pyrazolo[3,4-b]pyrazin-1-yl)-N,N-dimethylacetamide; |
| 51 | 5-((6-(3-(Difluoromethoxy)-4-fluorophenyl)-1H-pyrazolo[3,4-b]pyrazin-1-yl)methyl)oxazolidin-2-one; |
| 52 | 6-(3-(Difluoromethoxy)-4-fluorophenyl)-1-((5-methoxypyridin-3-yl)methyl)-1H-pyrazolo[3,4-b]pyrazine; and |

TABLE 1-continued

| Ex # | Compound name |
|---|---|
| 53 | 2-(6-(4-(1,1-Difluoroethyl)phenyl)-1H-pyrazolo[3,4-b]pyrazin-1-yl)-N,N-dimethylacetamide; | and pharmaceutically acceptable salts, N-oxides, or solvates thereof.

A further embodiment of the current invention is a compound selected from the group consisting of:
2-[6-[3-(Difluoromethyl)-4-fluoro-phenyl]pyrazolo[3,4-b]pyrazin-1-yl]-N,N-dimethylacetamide;
1-(Azetidin-1-yl)-2-[6-[3-(difluoromethyl)-4-fluoro-phenyl]pyrazolo[3,4-b]pyrazin-1-yl]ethanone;
1-(Azetidin-1-yl)-2-[6-[3-(difluoromethoxy)-4-fluoro-phenyl]pyrazolo[3,4-b]pyrazin-1-yl]ethanone; and
2-[6-[3-(Difluoromethyl)-4-fluoro-phenyl]pyrazolo[3,4-b]pyrazin-1-yl]-1-(3-fluoroazetidin-1-yl)ethanone;
and pharmaceutically acceptable salts, solvates, stereoisomers, isotopic variants, or N-oxides thereof.

An additional embodiment of the invention is a pharmaceutical composition comprising:
(A) an effective amount of at least one compound selected from compounds of Formula (I):

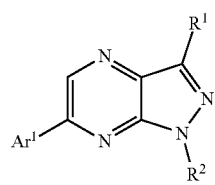

wherein
$R^1$ is H or halo;
$Ar^1$ is selected from the group consisting of:
(a) phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl; and
(b) thienyl substituted with $CF_3$; and
$R^2$ is selected from the group consisting of:
(c)

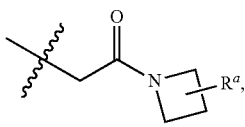

wherein $R^a$ is selected from the group consisting of: H, halo, and $C_{1-6}$alkyl;

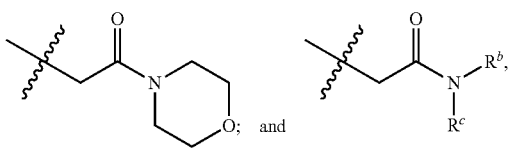

wherein $R^b$ is $C_{1-6}$alkyl, and $R^c$ is $C_{1-6}$alkyl;

(d)

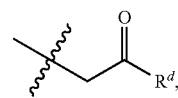

wherein $R^d$ is $C_{1-6}$alkyl, or $C_{3-6}$cycloalkyl; and (e)

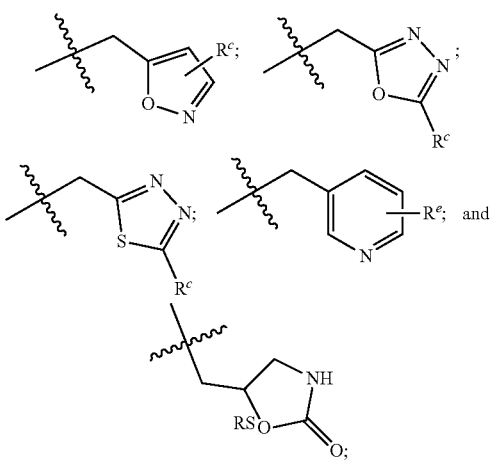

wherein $R^e$ is selected from the group consisting of: halo, $OC_{1-6}$alkyl, and CN;
and pharmaceutically acceptable salts, stereoisomers, isotopic variants, N-oxides or solvates of compounds of Formula (I);
and (B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

Also within the scope of the invention are enantiomers and diastereomers of the compounds of Formula (I) (as well as Formulas (IA), and (IB)). Also within the scope of the invention are the pharmaceutically acceptable salts, N-oxides or solvates of the compounds of Formula (I) (as well as Formulas (IA), and (IB)). Also within the scope of the invention are the pharmaceutically acceptable prodrugs of compounds of Formula (I) (as well as Formulas (IA), and (IB)), and pharmaceutically active metabolites of the compounds of Formula (I) (as well as Formulas (IA), and (IB)).

Also within the scope of the invention are isotopic variations of compounds of Formula (I) (as well as Formulas (IA), and (IB)), such as, e.g., deuterated compounds of Formula (I). Also within the scope of the invention are the pharmaceutically acceptable salts, N-oxides or solvates of the isotopic variations of the compounds of Formula (I) (as well as Formulas (IA), and (IB)). Also within the scope of the invention are the pharmaceutically acceptable prodrugs of the isotopic variations of the compounds of Formula (I) (as well as Formulas (IA), and (IB)), and pharmaceutically active metabolites of the isotopic variations of the compounds of Formula (I) (as well as Formulas (IA), and (IB)).

An additional embodiment of the invention is a method of treating a subject suffering from or diagnosed with a disease, disorder, or medical condition mediated by GluN2B receptor activity, comprising administering to a subject in need of such treatment an effective amount of at least one compound selected from compounds of Formula (I):

(I)

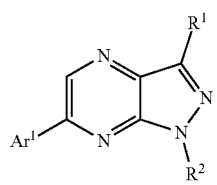

wherein
R$^1$ is H or halo;
Ar$^1$ is selected from the group consisting of:
(a) phenyl substituted with one, two or three members each independently selected from the group consisting of: halo, C$_{1-6}$alkyl, C$_{1-6}$perhaloalkyl, OC$_{1-6}$alkyl, and OC$_{1-6}$perhaloalkyl; and
(b) thienyl substituted with CF$_3$; and
R$^2$ is selected from the group consisting of:
(c)

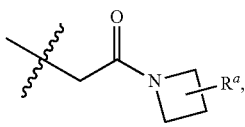

wherein R$^a$ is selected from the group consisting of: H, halo, and C$_{1-6}$alkyl;

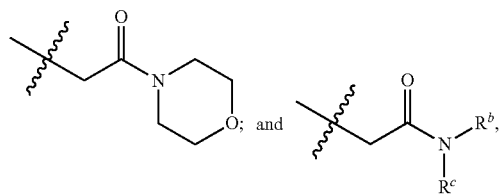

wherein R$^b$ is C$_{1-6}$alkyl, and R$^c$ is C$_{1-6}$alkyl;
(d)

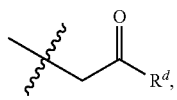

wherein R$^d$ is C$_{1-6}$alkyl, or C$_{3-6}$cycloalkyl; and
(e)

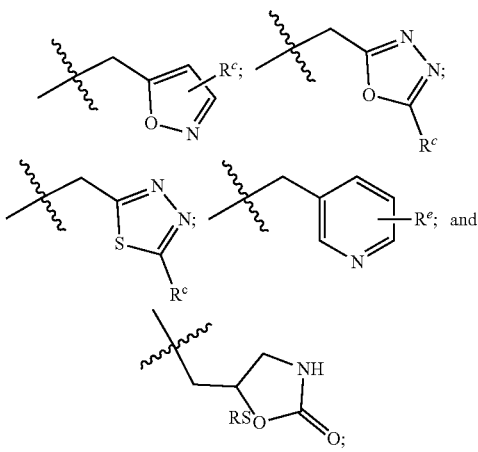

wherein R$^e$ is selected from the group consisting of: halo, OC$_{1-6}$alkyl, and CN;
and pharmaceutically acceptable salts, stereoisomers, isotopic variants, N-oxides, or solvates thereof, to a subject in need thereof.

An additional embodiment of the invention is a method of treating a subject suffering from or diagnosed with a disease, disorder, or medical condition mediated by GluN2B receptor activity, comprising administering to a subject in need of such treatment an effective amount of at least one compound selected from compounds of Formula (I) (as well as Formulas (IA), and (IB)), enantiomers and diastereomers of the compounds of Formula (I), isotopic variations of the compounds of Formula (I), and pharmaceutically acceptable salts of all of the foregoing.

In preferred embodiments of the inventive method, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9)

cerebrovascular diseases, acute and chronic; and any sequelae of cerebrovascular diseases.

Examples of mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, depressive disorders with psychotic symptoms; persistent mood disorders, such as cyclothymia, dysthymia, euthymia; and premenstrual dysphoric disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present invention include, but are not limited to mental and behavioral disorders associated with childbirth, including but not limited to postnatal (postpartum) and prenatal depression; eating disorders, including but not limited to anorexia nervosa, bulimia nervosa, pica and binge eating disorder.

Examples of extrapyramidal and movement disorders that can be treated according to the present invention include, but are not limited to Parkinson's disease; second Parkinsonism, such as post encephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present invention include, but are not limited to dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord);

Examples for episodic and paroxysmal disorders that can be treated according to the present invention include, but are not limited to epilepsy, including localization-related (focal) (partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-6}$alkyl as used here refers to a straight- or branched-chain alkyl group having from 1 to 4 carbon atoms in the chain. The term $C_{1-6}$alkyl as used here refers to a straight- or branched-chain alkyl group having from 1 to 6 carbon atoms in the chain.

The term "halo" represents chloro, fluoro, bromo or iodo.

The term "perhaloalkyl" or "haloalkyl" refers to a straight- or branched-chain alkyl group having from 1 to 6 carbon atoms in the chain optionally substituting hydrogens with halogens. The term "$C_{1-3}$perhaloalkyl" as used here refers to a straight- or branched-chain alkyl group having from 1 to 3 carbon atoms in the chain, optionally substituting hydrogens with halogens. The term "$C_{1-6}$perhaloalkyl" as used here refers to a straight- or branched-chain alkyl group having from 1 to 6 carbon atoms in the chain, optionally substituting hydrogens with halogens. Examples of "perhaloalkyl", "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), chloropropyl ($CH_2CH_2CH_2Cl$), and groups that in light of the ordinary skill in the art and the teachings provided herein would be considered equivalent to any one of the foregoing examples.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "cyano" refers to the group —CN.

The term "aryl" refers to a monocyclic, aromatic carbocycle (ring structure having ring atoms that are all carbon) having 6 atoms per ring. (Carbon atoms in the aryl groups are $sp^2$ hybridized.)

The term "phenyl" represents the following moiety:

The term "thienyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

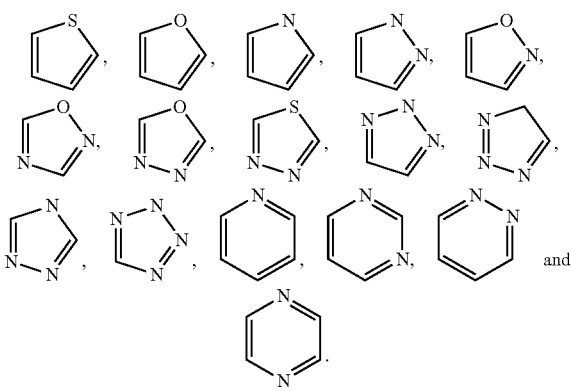

Those skilled in the art will recognize that the species of heteroaryl, cycloalkyl, aryl and heterocycloalkyl groups listed or illustrated above are not exhaustive, and that additional species within the scope of these defined terms may also be selected.

A "heterocycloalkyl" refers to a monocyclic, bicyclic (fused or spirocyclic) ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

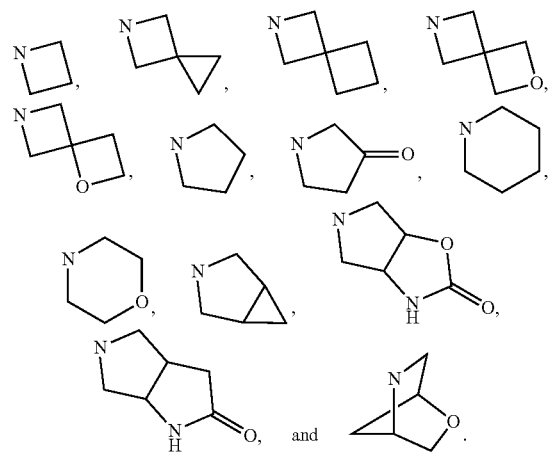

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

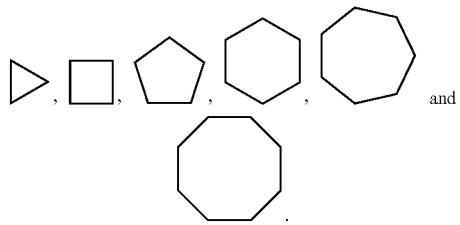

The term "pyridinyl" or "pyridyl" represents the following moiety:

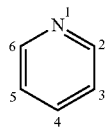

The pyridinyl or pyridyl moiety can be attached through any one of the 2-, 3-, 4-, 5-, or 6-position carbon atoms.

The term "azetidinyl" represents a 4-membered heterocycloalkyl moiety having one ring nitrogen. When the azetidinyl moiety is a substituent, it can be attached through any carbon atom or through the nitrogen atom, as permitted.

The term "morpholinyl" represents the following moiety:

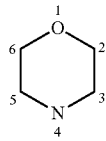

When the morpholinyl moiety is a substituent, it can be attached through any one of the 2-, 3-, 4-, 5-, or 6-position atoms, as permitted.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

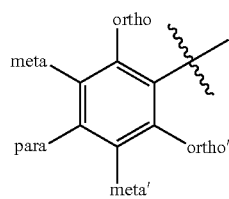

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

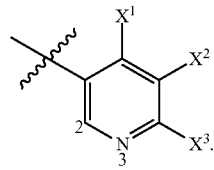

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed the structures are named using (R) and (S).

The symbols  and  are used as meaning the same spatial arrangement in chemical structures shown herein. Analogously, the symbols  and  are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) (as well as Formulas (IA), and (IB)), or pharmaceutically acceptable salts of compounds of Formula (I) (as well as Formulas (IA), and (IB)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (IA), and (IB)) or pharmaceutically acceptable salts of compounds of Formula (I) (as well as Formulas (IA), and (IB)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example deuterium (i.e., D or $^2H$); or tritium (i.e., T or $^3H$)), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by using a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^a$, $R^b$, $R^e$, $R^d$, $R^e$, $R^f$, $Ar^1$, PG and Hal, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^a$, $R^b$, $R^e$, $R^d$, $R^e$, $R^f$, $Ar^1$, PG and Hal, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-6}$ refers independently to embodiments that have one carbon member ($C_1$), embodiments that have two carbon members ($C_2$), embodiments that have three carbon members ($C_3$), and embodiments that have four carbon members ($C_4$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA), and (IB)), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmacopeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA), and (IB)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (IA), and (IB)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA), and (IB)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutamic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA), and (IB)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) (as well as Formulas (IA), and (IB)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in *"Design of Prodrugs"*, ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA), and (IB)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA), and (IB)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., J Med Chem. 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA), and (IB)), which may also be used in the methods of the invention. A "pharmaceutically active metabolite" means a pharmacologically active product of metabolism in the body of a compound of Formula (I) (as well as Formulas (IA), and (IB) as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (IA), and (IB)) and their pharmaceutically acceptable salts, pharmaceutically acceptable prodrugs, and pharmaceutically active metabolites of the present invention are useful as modulators of the GluN2B receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the GluN2B receptor expression or activity, and "activators" are compounds that increase, activate, facilitate, sensitize, or up-regulate GluN2B receptor expression or activity.

The term "treat", "treatment" or "treating", as used herein, is intended to refer to administration of an active agent or composition of the invention to a subject for the purpose of affecting a therapeutic or prophylactic benefit through modulation of GluN2B receptor activity. Treating includes reversing, ameliorating, alleviating, inhibiting the progress of, lessening the severity of, or preventing a disease, disorder, or condition, or one or more symptoms of such disease, disorder or condition mediated through modulation of GluN2B receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by GluN2B receptor activity, such as: bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, disruptive mood dysregulation disorder, depressive disorders with psychotic symptoms; persistent mood disorders, such as cyclothymia, dysthymia, euthymia; and premenstrual dysphoric disorder; anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome; pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills; postnatal (postpartum) and prenatal depression; eating disorders, including but not limited to anorexia nervosa, bulimia nervosa, pica and binge eating disorder; Parkinson's disease; second Parkinsonism, such as post encephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome; dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); epilepsy, including localization-related (focal)(partial) idiopathic epilepsy and epileptic syndromes with seizures of localized onset, localization-related (focal) (partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures; epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus; persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy; and acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis, and ALS; subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, nonpyogenic thrombosis of intracranial venous system, cerebral arteritis, cerebral amyloid angiopathy and sequelae of cerebrovascular diseases; glaucoma and other neuropathies; dementias, vascular dementia, Lewy body dementia, frontotemporal dementia, and HIV-dementia; vertigo and nystagmus; tinnitus; neuropsychiatric systemic lupus erythematosus; disruptive mood dysregulation disorder; schizophrenia spectrum disorder; and sleep/wake disorders.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by GluN2B activity, such as another GluN2B modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 2

| Term | Acronym |
| --- | --- |
| Acetonitrile | ACN |
| Aqueous | aq |
| Atmosphere | atm |
| tert-Butylcarbamoyl | Boc; or BOC |
| benzotriazol-1-yloxy-tris(dimethylamino)phosphonium hexafluorophosphate | BOP |
| Broad | br |
| Diatomaceous Earth | Celite ® |
| Diethylaminosulfur trifluoride | DAST |
| N,N'-dicyclohexylcarbodiimide | DCC |
| Dichloromethane | DCM |
| N-ethyldiisopropylamine | DIEA, DIPEA |
| 4-dimethylaminopyridine | DMAP |
| N'N-dimethylformamide | DMF |
| 1-Ethyl-3-(3-dimethylaminopropyl)carbodiimide | EDC, EDAC or EDCI |
| Electrospray ionization | ESI |
| Ethyl acetate | EtOAc, EA |
| Ethanol | EtOH |
| Normal-phase silica gel chromatography, flash column chromatography | FCC |
| Grams | g |
| GluNR2B * | $GluN_{2B}$, NMDA-R2B, NR2B, hNR3 |
| Hours | h |
| 1-[bis(dimethylamino)methylene]-1H-1,2,3-triazolo[4,5-b]pyridinium 3-oxid hexafluorophosphate | HATU |
| N,N,N',N'-tetramethyl-O-(1H-benzotriazol-1-yl)uronium hexafluorophosphate | HBTU |
| hydroxybenzotriazole | HOBt |
| High-pressure liquid chromatography | HPLC |
| Hertz | Hz |
| Isopropyl alcohol | iPrOH, IPA |
| Liquid chromatography and mass spectrometry | LCMS |

TABLE 2-continued

| Term | Acronym |
| --- | --- |
| Methanol | MeOH |
| Molar | M |
| Mass to charge ratio | m/z |
| Milligrams | mg |
| Minute | min |
| Milliliter | mL |
| Microliter | μL |
| Millimoles | mmol |
| Mass spectrometry | MS |
| N-fluorobenzenesulfonimide | NFSI |
| N-fluoro-o-benzenedisulfonimide | NFOBS |
| Normal | N |
| Nuclear magnetic resonance | NMR |
| Parts per million | PPm |
| palladium-tetrakis(triphenylphosphine) | $Pd(PPh_3)_4$ |
| Bis(diphenylphosphino)ferrocene]dichloropalladium(II), complex with dichloromethane | $PdCl_2(dppf)\text{-}CH_2Cl_2$ |
| Precipitate | ppt |
| Polytetrafluoroethylene | PTFE |
| Retention time | $R_t$ |
| Room temperature | rt |
| Saturated | sat |
| 1-chloromethyl-4-fluoro-1,4-diazoniabicyclo[2.2.2] octane bis(tetrafluoroborate) | Selectflor ® |
| (2-chloromethoxyethyl)trimethylsilane | SEM-chloride |
| Supercritical Fluid Chromatography | SFC |
| Temperature | T |
| 2,4,6-tripropyl-1,3,5,2,4,6-trioxatriphosphorinane-2,4,6-trioxide | T3P ® |
| Tetrabutylammonium fluoride | TBAF |
| Tetrahydrofuran | THF |
| Trifluoroacetic acid | TFA |
| Triethylamine | TEA |
| Thin layer chromatography | TLC |
| Volume in milliliters of solvent per gram of substrate | V, or volumes |

* (Collingridge, G.L, et al, Neuropharmacology, 2009, 56, 2-5)

Preparative Examples

Exemplary compounds useful in methods of the invention will now be described by reference to the illustrative synthetic schemes for their general preparation below and the specific examples to follow.

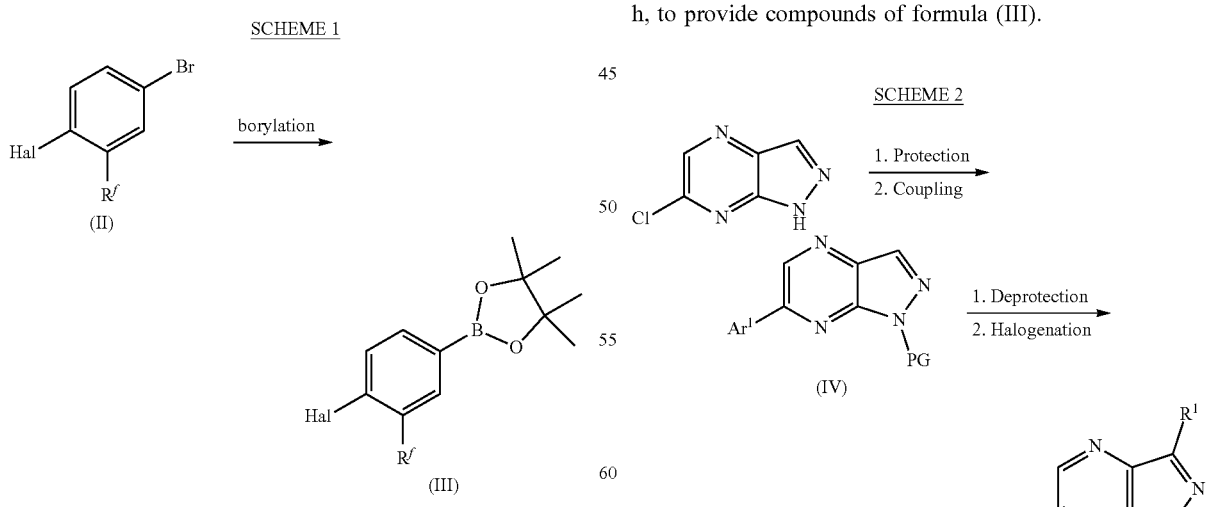

According to SCHEME 1, a compound of formula (II), is borylated employing palladium catalyzed borylation conditions known to one skilled in the art to provide a compound of formula (III). For example, a compound of formula (II), where Hal is Cl, or F, $R^f$ is $CF_2H$, $OCF_2H$, or $CF_2CH_3$; is reacted with a borylation reagent such as 4,4,4',4',5,5,5',5'-octamethyl-2,2'-bi-1,3,2-dioxaborolane (bis(pinacolato)diboron), and the like; potassium acetate; a palladium catalyst such as $PdCl_2(dppf)\text{-}CH_2Cl_2$, and the like; in a suitable solvent such as tetrahydrofuran (THF), N,N-dimethylformamide (DMF), 1,4-dioxane, or a mixture thereof, at a temperature ranging from 23 to 90° C.; for a period of about 1-4 h, to provide compounds of formula (III).

According to SCHEME 2, commercially available or synthetically accessible 6-chloro-1H-pyrazolo[3,4-b]pyrazine is protected with a carbamate protecting group, employing established methodologies. For example, 6-chloro-1H-pyrazolo[3,4-b]pyrazine is reacted with di-tert-butyl dicarbonate (BOC-anhydride), at room temperature, for a period of about 4-7 h, to provide tert-butyl 6-chloro-1H-pyrazolo[3,4-b]pyrazine-1-carboxylate. tert-Butyl 6-chloro-1H-pyrazolo[3,4-b]pyrazine-1-carboxylate is reacted in a metal-mediated cross-coupling reaction to provide a compound of formula (IV), where PG is BOC, and $Ar^1$ is a group as defined in claim 1. For example, tert-butyl 6-chloro-1H-pyrazolo[3,4-b]pyrazine-1-carboxylate is reacted with a commercially available or synthetically accessible suitably substituted aryl or heteroaryl boronic acid, boronate ester, and the like, in the presence of a palladium catalyst such as palladium-tetrakis(triphenylphosphine) ($Pd(PPh_3)_4$), [1,1'-bis(diphenylphosphino)ferrocene]dichloropalladium(II) ($PdCl_2(dppf)$), and the like, in a suitable solvent such as 1,4-dioxane, DMF, water, or a mixture thereof, at a temperature ranging from 60 to 110° C., for a period of about 16 hours, to provide a compound of formula (IV). Cleavage of the BOC protecting group on a compound of formula (IV) is achieved according to procedures known to one skilled in the art and employing established methodologies. For example, under acidic conditions such as $TFA/CH_2Cl_2$, HCl/Dioxane, and the like, to provide a compound of formula (V) where $R^1$ is H.

A compound of formula (V) is prepared under halogenation conditions known to one skilled in the art. For example, 6-(3-(difluoromethyl)-4-fluorophenyl)-1H-pyrazolo[3,4-b]pyrazine is fluorinated using an electrophilic fluorine source such as, N-fluorobenzenesulfonimide (NFSI), N-fluoro-o-benzenedisulfonimide (NFOBS), or 1-chloromethyl-4-fluoro-1,4-diazoniabicyclo[2.2.2]octane bis(tetrafluoroborate) (Selectflor®), preferably Selectflor®; in a suitable solvent such as acetonitrile (ACN), and the like; at temperatures ranging from 0 to 100° C.; to provide a compound of formula (V), where $R^1$ is F.

According to SCHEME 3, a 2-haloacetyl chloride of formula (VI), where Hal is Cl or Br, such as 2-chloroacetyl chloride, 2-bromoacetyl chloride, and the like; is reacted with a commercially available or synthetically accessible suitably substituted azetidine of formula (VII), where $R^a$ is H, halo, or $C_{1-6}$alkyl; or a suitably substituted heterocycloalkylamine of formula (IX), such as morpholine; or a suitably substituted amine of formula (XI), where $R^d$ is $C_{3-6}$cycloalkyl or $C_{3-6}$cycloalkyl substituted with two F members, and $R^e$ is H or $CH_3$; in the presence of a suitable base such as triethylamine (TEA) or sodium bicarbonate; in a solvent such as acetonitrile (ACN) or dichloromethane (DCM); at temperatures ranging from 0° C. to rt; to provide a compound of formula (VIII), formula (X), and formula (XII).

SCHEME 4

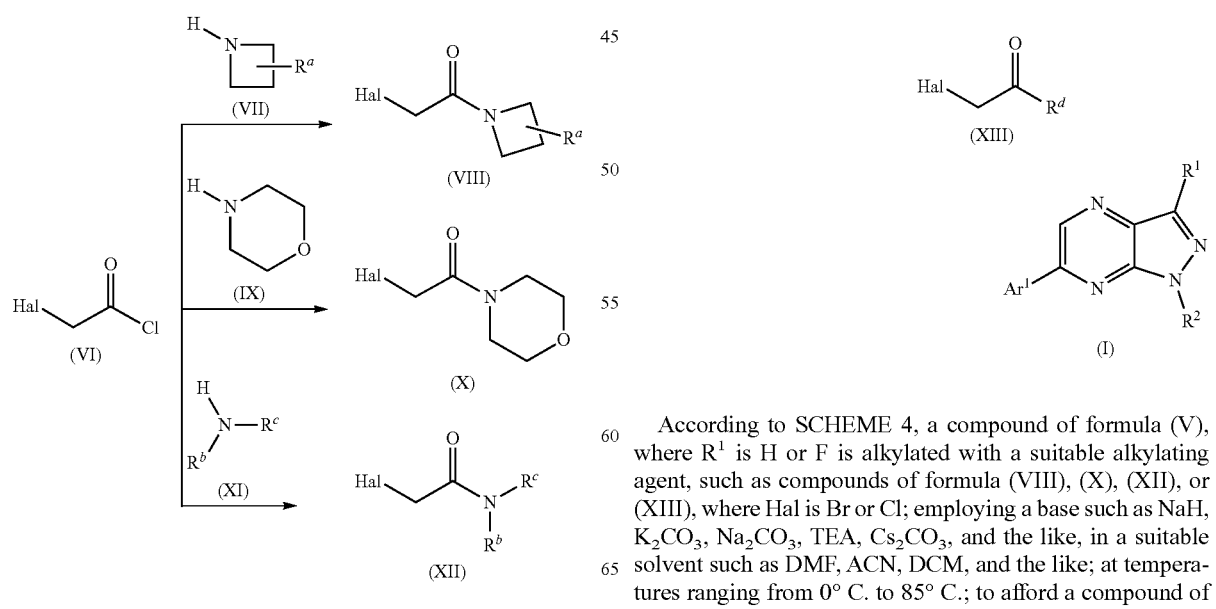

According to SCHEME 4, a compound of formula (V), where $R^1$ is H or F is alkylated with a suitable alkylating agent, such as compounds of formula (VIII), (X), (XII), or (XIII), where Hal is Br or Cl; employing a base such as NaH, $K_2CO_3$, $Na_2CO_3$, TEA, $Cs_2CO_3$, and the like, in a suitable solvent such as DMF, ACN, DCM, and the like; at temperatures ranging from 0° C. to 85° C.; to afford a compound of Formula (I).

SCHEME 3

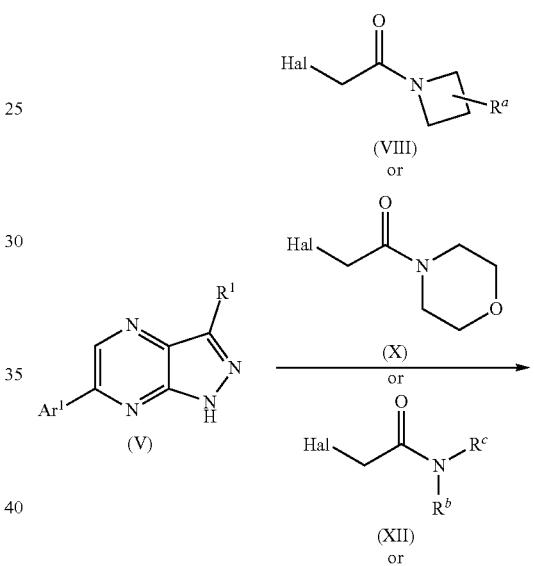

SCHEME 5

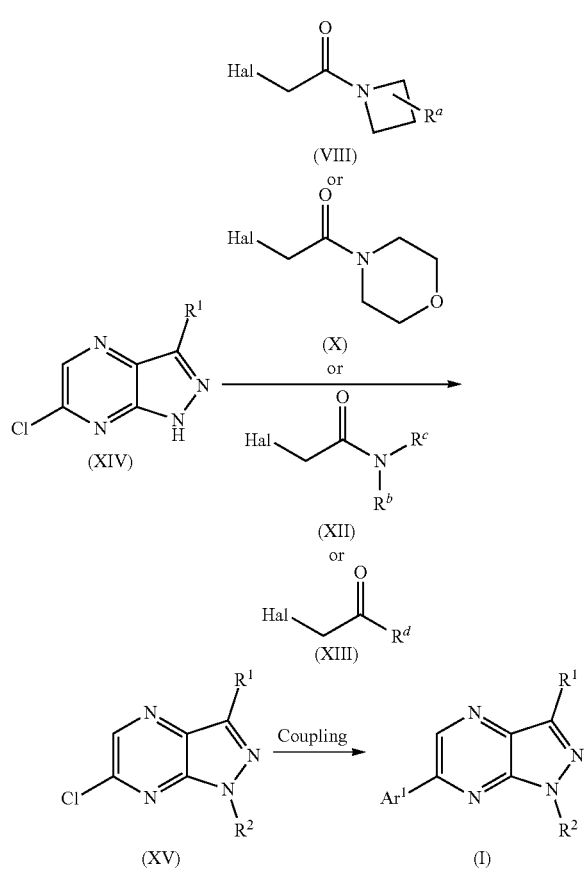

According to SCHEME 5, a compound of formula (XIV), where $R^1$ is H or F, is alkylated with a synthetically accessible or commercially available compound formula (VIII), (X), (XII), or (XIII), where HAL is Br or Cl; employing conditions previously described to provide a compound of formula (XV). A compound of formula (XV) is reacted in a metal-mediated cross-coupling reaction with a commercially available or synthetically accessible suitably substituted aryl or heteroaryl boronic acid, boronate ester, and the like; employing conditions previously described, to provide a compound of Formula (I).

SCHEME 6

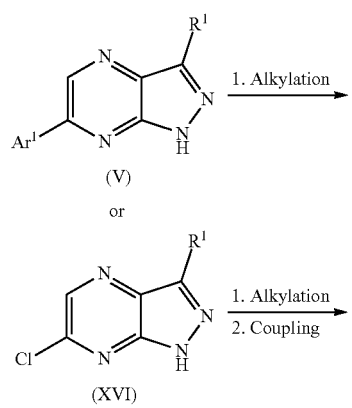

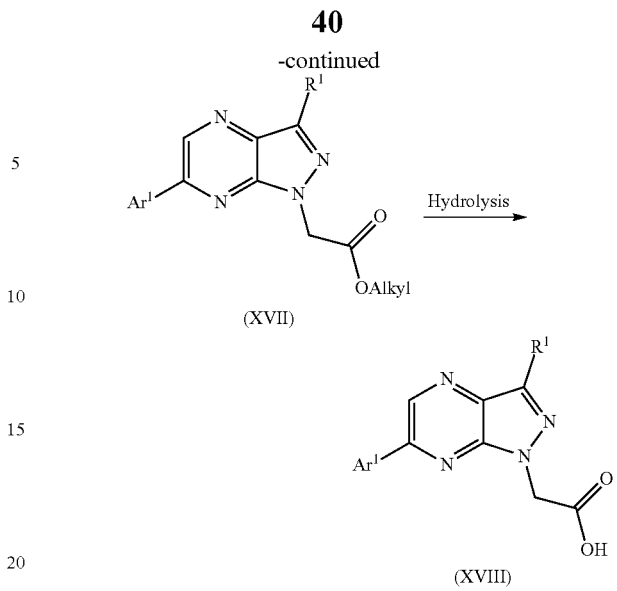

According to SCHEME 6, a compound of formula (V), where $R^1$ is H or F, and $Ar^1$ is as described in claim 1; is alkylated with an electrophile such as ethyl 2-bromoacetate, tert-butyl 2-bromoacetate, and the like; a base such as NaH, $Cs_2CO_3$, and the like; in a suitable solvent such as DMF, and the like; at temperatures ranging from 0° C.; to rt to provide a compound of formula (XVII). A compound of formula (XVII), is prepared in two steps from a compound of formula (XVI), where $R^1$ is H or F. In a first step, a compound of formula (XVI) is alkylated employing conditions previously described; subsequent coupling in a metal mediated cross coupling reaction with a suitably substituted phenyl or thienyl boronic acid or boronate ester, employing conditions previously described provides a compound of formula (XVII).

Saponification of an ester of formula (XVIII), where alkyl is $C_{1-6}$alkyl; is achieved under basic conditions such as LiOH, NaOH, KOH and the like; in a suitable solvent such as methanol (MeOH), THF, water, or a mixture thereof, affords a compound of formula (XVIII). Alternatively, acidic hydrolysis of an ester of formula (XVII) is accomplished using an acidic solvent such as 6 N aqueous HCl and the like, at temperatures ranging from rt to 80° C., to afford a compound of formula (XVIII).

It will be understood that in certain instances, in situ ester hydrolysis, without the isolation of a discrete ester (XVII) may occur to provide a compound of formula (XVIII).

SCHEME 7

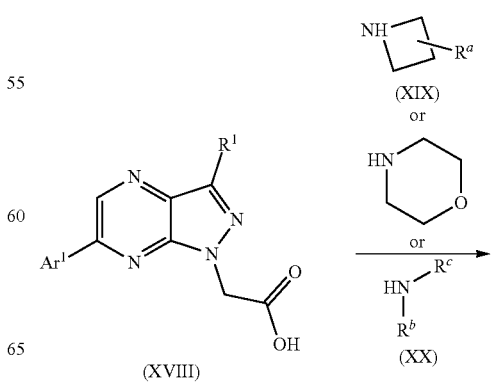

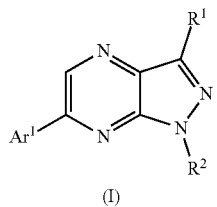

(I)

According to SCHEME 7, a compound of formula (XVIII), where R¹ is H or F, Ar¹ is a suitably substituted phenyl or thienyl, is reacted with an amine compound of formula (XIX), morpholine, or a compound of formula (XX) in a conventional amide bond-forming reaction employing techniques such as coupling reactions which are well-known to those skilled in the art (such as HATU (1-[bis(dimethyl-amino)methylene]-1H-1,2,3-triazolo[4,5-b]pyridinium 3-oxid hexafluorophosphate), BOP (benzotriazol-1-yloxy-tris(dimethylamino)phosphonium hexafluorophosphate), or conversion of the acid to an acid chloride). For example, reaction of morpholine, a suitably substituted azetidine of formula (XIX), or an amine of formula (XX) where $R^a$, $R^b$, and $R^c$ are as defined in claim 1; with an acid compound of formula (XVIII), where the acid is activated with an appropriate activating reagent, for example a carbodiimide, such as N,N'-dicyclohexylcarbodiimide (DCC) or 1-ethyl-3-(3-dimethylaminopropyl)carbodiimide (EDC, EDAC or EDCI) optionally in the presence of hydroxybenzotriazole (HOBt) and/or a catalyst such as 4-dimethylaminopyridine (DMAP); a halotrisaminophosphonium salt such as (benzotriazol-1-yloxy)tris(dimethylamino)phosphonium hexafluorophosphate (BOP), or bromotripyrrolidinophosphonium hexafluorophosphate (PyBroP®); a suitable pyridinium salt such as 2-chloro-1-methyl pyridinium chloride; or another suitable coupling agent such as N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), 2,4,6-tripropyl-1,3,5,2,4,6-trioxatriphosphorinane-2,4,6-trioxide (T3P®) and the like. Coupling reactions are conducted in a suitable solvent such as DCM, THF, DMF and the like, optionally in the presence of a tertiary amine such as N-methylmorpholine, N-ethyldiisopropylamine (DIEA, DIPEA), or triethylamine (TEA), at a temperature ranging from about 0° C. to rt; to provide a compound of Formula (I).

Compounds of Formula (I) may be converted to their corresponding salts using methods known to one of ordinary skill in the art. For example, an amine of Formula (I) is treated with trifluoroacetic acid, HCl, or citric acid in a solvent such as Et₂O, CH₂Cl₂, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

Examples

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na₂SO₄ or MgSO₄. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE tubing to a LTF-VS mixer (Little Things Factory GmbH (http://www.ltf-gmbh.com), unless otherwise indicated.

Normal-phase silica gel chromatography (FCC) was performed on silica gel (SiO₂) using prepacked cartridges.

Preparative reverse-phase high performance liquid chromatography (RP HPLC) was performed on either:

METHOD A. An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM NH₄OH was held for 2 min, then a gradient of 5-99% ACN over 15 min, then held at 99% ACN for 5 min, with a flow rate of 40 or 80 mL/min.

or

METHOD B. A Shimadzu LC-8A Series HPLC with an Inertsil ODS-3 column (3 m, 30×100 mm, T=45° C.), mobile phase of 5% ACN in H₂O (both with 0.05% TFA) was held for 1 min, then a gradient of 5-99% ACN over 6 min, then held at 99% ACN for 3 min, with a flow rate of 80 mL/min.

or

METHOD C. A Shimadzu LC-8A Series HPLC with an XBridge C18 OBD column (5 m, 50×100 mm), mobile phase of 5% ACN in H₂O (both with 0.05% TFA) was held for 1 min, then a gradient of 5-99% ACN over 14 min, then held at 99% ACN for 10 min, with a flow rate of 80 mL/min.
or METHOD D. A Gilson HPLC with an XBridge C18 column (5 μm, 100×50 mm), mobile phase of 5-99% ACN in 20 mM NH$_4$OH over 10 min and then hold at 99 ACN for 2 min, at a flow rate of 80 mL/min.

METHOD E. A Wufeng LC100 equipped with a manual Rheodyne 3725i sampler with a Gemini-NX C18 column (5 μM, 30×100 mm), and a mobile phase of 0-90% MeCN:10 mM (NH$_4$)HCO$_3$ (9:1) in 10 mM aqueous (NH$_4$)HCO$_3$ with 0.1% NH$_4$OH over 16 min or 18 min, with a flow rate of 30 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, MA) or OEMetaChem V1.4.0.4 (Open Eye).

Compounds designated as R* or S* are enantiopure compounds where the absolute configuration was not determined.

Examples

Intermediate 1: 6-Chloro-1-((2-(trimethylsilyl)ethoxy)methyl)-1H-pyrazolo[3,4-b]pyrazine

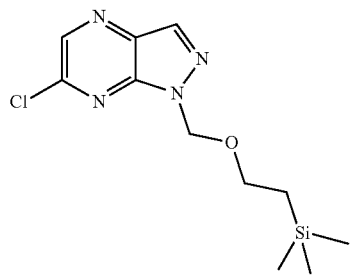 [SMILES: C[Si](C)(C)CCOCn1ncc2ncc(Cl)nc21]

Step A: 6-Chloro-1H-pyrazolo[3,4-b]pyrazine. A solution of 3,5-dichloropyrazine-2-carbaldehyde (1.0 g, 5.65 mmol) in isopropyl alcohol (24 mL) was charged with hydrazine hydrate (0.95 mL, 10.52 mmol). The mixture was heated in a microwave for 30 min at 120° C. The reaction mixture was then added a solution of 0.25 M HCl (100 mL) and stirred at rt for 40 min. The solution was filtered through a bed of Celite® and rinsed with 10% IPA/H$_2$O mixture. The filtrate was extracted with CHCl$_3$ (3×50 mL). The combined organics were dried over Na$_2$SO$_4$, filtered and concentrated under reduced pressure to yield 6-chloro-1H-pyrazolo[3,4-b]pyrazine (481 mg, 55%). MS (ESI): mass calcd. for C$_5$H$_3$ClN$_4$, 154.0; m/z found, 155.0 [M+H]$^+$.

Step B: 6-Chloro-1-((2-(trimethylsilyl)ethoxy)methyl)-1H-pyrazolo[3,4-b]pyrazine. Under a nitrogen atmosphere, a suspension of 6-chloro-1H-pyrazolo[3,4-b]pyrazine (0.410 g, 2.65 mmol) and NaH (60% dispersion in mineral oil, 127 mg, 3.18 mmol) in DMF (25 mL) was cooled to 0° C., and stirred for 15 min. The reaction mixture was charged with (2-chloromethoxyethyl)trimethylsilane (SEM-chloride) (0.516 mL, 2.92 mmol) and stirred at r.t. for 1 hour. The reaction mixture was quenched with water (30 mL) and extracted with EtOAc (3×10 mL). The combined organics were dried over Na$_2$SO$_4$, filtered and concentrated under reduced pressure. Purification (FCC, SiO$_2$, 0-20% EtOAc in hexanes) afforded the title compound (653.7 mg, 87%). MS (ESI): mass calcd. for C$_{11}$H$_{17}$ClN$_4$OSi, 284.1; m/z found, 285.1 [M+H]$^+$.

Intermediate 2: 6-(3-(Difluoromethyl)-4-fluorophenyl)-1H-pyrazolo[3,4-b]pyrazine

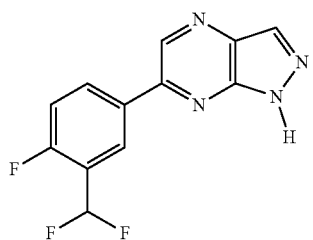 [SMILES: Fc1ccc(-c2cnc3cn[nH]c3n2)cc1C(F)F]

Step A: 6-(3-(Difluoromethyl)-4-fluorophenyl)-1-((2-(trimethylsilyl)ethoxy)methyl)-1H-pyrazolo[3,4-b]pyrazine. 6-Chloro-1-((2-(trimethylsilyl)ethoxy)methyl)-1H-pyrazolo[3,4-b]pyrazine (Intermediate 1, 100 mg, 0.351 mmol), 2-(3-(difluoromethyl)-4-fluorophenyl)-4,4,5,5-tetramethyl-1,3,2-dioxaborolane (Intermediate 14, 115 mg, 0.421 mmol), Pd(dppf)Cl$_2$ (33 mg, 0.046 mmol), and sodium carbonate (112 mg, 1.05 mmol) were suspended in a mixture of water (0.5 mL) and ACN (5 mL) in a vial. The mixture was purged briefly with N$_2$, then stirred at 80° C. for 2.5 hours. The reaction mixture was diluted with water (30 mL) and extracted with EtOAc (3×10 mL). The combined organics were dried over Na$_2$SO$_4$, filtered and concentrated under reduced pressure. Purification (FCC, SiO$_2$, 0-50% EtOAc in hexanes) afforded the title compound (120 mg, 87%). MS (ESI): mass calcd. for C$_{18}$H$_{21}$F$_3$N$_4$OSi, 394.1; m/z found, 395.0 [M+H]$^+$.

Step B: 6-(3-(Difluoromethyl)-4-fluorophenyl)-1H-pyrazolo[3,4-b]pyrazine. To a solution of 6-(3-(difluoromethyl)-4-fluorophenyl)-1-((2-(trimethylsilyl)ethoxy)methyl)-1H-pyrazolo[3,4-b]pyrazine (120 mg, 0.304 mmol) in THF (25 mL) was added tetrabutylammonium fluoride (TBAF) (0.761 mL, 1M in THF, 0.761 mmol). The resulting solution was stirred at 70° C. overnight. After completion, the reaction mixture was diluted with water (30 mL) and extracted with EtOAc (3×10 mL). The combined organics were dried over Na$_2$SO$_4$, filtered and concentrated under reduced pressure. The crude material was purified (FCC, SiO$_2$, 0-70% EtOAc in hexanes) to afford the title product (70 mg, 87%). MS (ESI): mass calcd. for C$_{18}$H$_7$F$_3$N$_4$, 264.1; m/z found, 265.0 [M+H]$^+$.

Intermediate 3: 2-(6-Chloro-1H-pyrazolo[3,4-b]pyrazin-1-yl)-N,N-dimethylacetamide

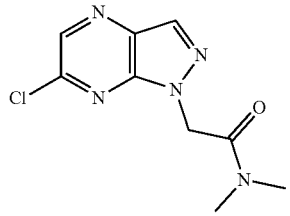 [SMILES: CN(C)C(=O)Cn1ncc2ncc(Cl)nc21]

Under a nitrogen atmosphere, a suspension of 6-chloro-1H-pyrazolo[3,4-b]pyrazine (100 mg, 0.647 mmol) and $K_2CO_3$ (107 mg, 0.776 mmol) in DMF (3 mL) charged with 2-chloro-N,N-dimethylacetamide (72 µL, 0.712 mmol) and stirred at r.t. overnight. The reaction mixture was diluted with water (10 mL) and extracted with EtOAc (3×10 mL). The combined organics were dried over $Na_2SO_4$, filtered and concentrated under reduced pressure. Purification (FCC, $SiO_2$, 0-100% EtOAc in hexanes) afforded the title compound (47.2 mg, 30%). MS (ESI): mass calcd. for $C_9H_{10}ClN_5O$, 239.1; m/z found, 240.1 $[M+H]^+$. $^1$H NMR (500 MHz, Chloroform-d) δ 8.54 (s, 1H), 8.34 (s, 1H), 5.34 (s, 2H), 3.16 (s, 3H), 2.99 (s, 3H).

Intermediate 4: 6-Chloro-1-((5-fluoropyridin-3-yl)methyl)-1H-pyrazolo[3,4-b]pyrazine

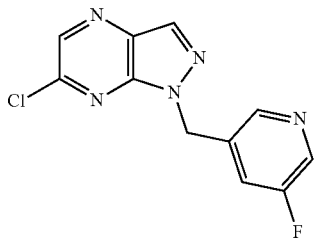 [SMILES: Fc1cncc(Cn2ncc3ncc(Cl)nc32)c1]

Under a nitrogen atmosphere, a suspension of 6-chloro-1H-pyrazolo[3,4-b]pyrazine (50 mg, 0.324 mmol) and $Cs_2CO_3$ (316 mg, 0.970 mmol) in DMF (1 mL) was charged with 3-(chloromethyl)-5-fluoropyridine HCl (65 mg, 0.357 mmol) and stirred at r.t. for 1 hour. The reaction mixture was diluted with water (5 mL) and extracted with EtOAc (3×5 mL). The combined organics were dried over $Na_2SO_4$, filtered and concentrated under reduced pressure. The crude material was purified (FCC, $SiO_2$, 0-100% EtOAc in hexanes) to afford the title compound (47 mg, 54%). MS (ESI): mass calcd. for $C_{11}H_7FN_5$, 263.0; m/z found, 264.0 $[M+H]^+$. $^1$H NMR (500 MHz, DMSO-$d_6$) δ 8.78 (s, 1H), 8.61 (s, 1H), 8.54 (d, J=2.6 Hz, 1H), 8.47-8.44 (m, 1H), 7.68-7.61 (m, 1H), 5.79 (s, 2H).

Intermediate 5: 2-Chloro-1-(3-fluoroazetidin-1-yl)ethan-1-one

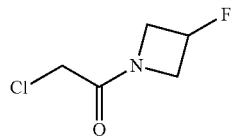

A mixture of chloroacetyl chloride (0.785 mL, 9.86 mmol) and sodium bicarbonate (2.22 g, 26.43 mmol) in DCM (20 mL) was cooled 0° C., then charged with to 3-fluoroazetidine HCl (1 g, 8.97 mmol) and stirred overnight warming to r.t. The reaction mixture was filtered and concentrated to a pale-yellow liquid. The crude sample was used crude without further purification (1.34 g, 99%). MS (ESI): mass calcd. for $C_5H_7ClFNO$, 151.0; m/z found, 152.1 $[M+H]^+$.

Intermediate 6: 2-Chloro-1-(3-methylazetidin-1-yl)ethan-1-one

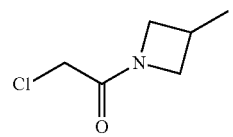

The title compound was prepared in a manner analogous to Intermediate 5 substituting 3-methylazetidine HCl for 3-fluoroazetidine HCl. MS (ESI): mass calcd. for $C_6H_{10}ClNO$, 147.1; m/z found, 148.1.

Intermediate 7: 6-(3-(Difluoromethyl)-4-fluorophenyl)-3-fluoro-1H-pyrazolo[3,4-b]pyrazine

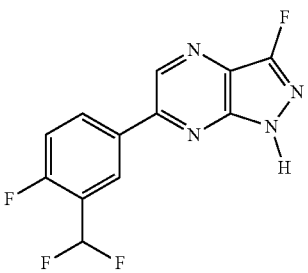 [SMILES: Fc1ccc(-c2cnc3c(F)n[nH]c3n2)cc1C(F)F]

A solution of 6-(3-(difluoromethyl)-4-fluorophenyl)-1H-pyrazolo[3,4-b]pyrazine (230 mg, 0.871 mmol) in ACN (4.4 mL) was charged with Selectflor® in three additions over 60 hours and stirred at 90° C. after each addition. The first addition was (463 mg, 1.307 mmol) after 20 hours a second addition of Selectflor® (154 mg, 0.435 mmol) was added and heating was continued. After 20 hours the last addition of Selectflor® (154 mg, 0.435 mmol) was added and heating continued for 20 final hours. The completed reaction was poured into water (15 mL) and extracted with EtOAc (3×15 mL). The combined organics were dried over $Na_2SO_4$, filtered and concentrated under reduced pressure. The crude material was purified (FCC, $SiO_2$, 10-50% EtOAc/Heptane to 10% MeOH/EtOAc) to afford the title compound (49 mg, 20%). MS (ESI): mass calcd. for $C_{12}H_6F_4N_4$, 282.1; m/z found, 283.0 [M+H]$^+$.

Intermediate 8: 6-(3-(Difluoromethoxy)-4-fluoro-phenyl)-1H-pyrazolo[3,4-b]pyrazine

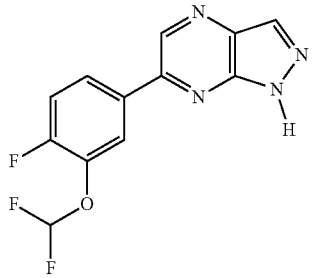 [SMILES: Fc1ccc(-c2cnc3cn[nH]c3n2)cc1OC(F)F]

The title compound was prepared in a manner analogous to Intermediate 2, using 2-(3-(difluoromethoxy)-4-fluoro-phenyl)-4,4,5,5-tetramethyl-1,3,2-dioxaborolane instead of 2-(3-(difluoromethyl)-4-fluorophenyl)-4,4,5,5-tetramethyl-1,3,2-dioxaborolane in Step A. MS (ESI): mass calcd. for $C_{12}H_7F_3N_4O$, 280.1; m/z found, 281.1 [M+H]$^+$.

Intermediate 9: 6-(3-(Difluoromethoxy)-4-chloro-phenyl)-1H-pyrazolo[3,4-b]pyrazine

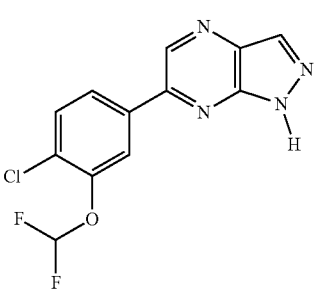 [SMILES: FC(F)Oc1cc(-c2cnc3cn[nH]c3n2)ccc1Cl]

The title compound was prepared in a manner analogous to Intermediate 2 substituting 2-(3-(difluoromethoxy)-4-chlorophenyl)-4,4,5,5-tetramethyl-1,3,2-dioxaborolane for 2-(3-(difluoromethyl)-4-fluorophenyl)-4,4,5,5-tetramethyl-1,3,2-dioxaborolane in Step A. MS (ESI): mass calcd. for $C_{12}H_7ClF_2N_4O$, 296.0; m/z found, 297.0 [M+H]$^+$.

Intermediate 10: 6-(4-Chloro-3-(1,1-difluoroethyl) phenyl)-1H-pyrazolo[3,4-b]pyrazine

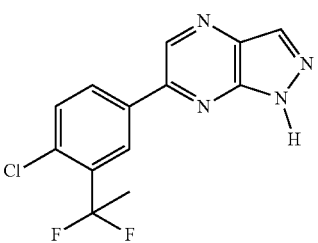 [SMILES: CC(F)(F)c1cc(-c2cnc3cn[nH]c3n2)ccc1Cl]

The title compound was prepared in a manner analogous to Intermediate 2 using 2-(4-chloro-3-(1,1-difluoroethyl) phenyl)-4,4,5,5-tetramethyl-1,3,2-dioxaborolane instead of 2-(3-(difluoromethyl)-4-fluorophenyl)-4,4,5,5-tetramethyl-1,3,2-dioxaborolane in Step A. MS (ESI): mass calcd. for $C_{13}H_9ClF_2N_4$, 294.0; m/z found, 295.0 [M+H]$^+$.

Intermediate 11: 6-(4-Fluoro-3-(1,1-difluoroethyl) phenyl)-1H-pyrazolo[3,4-b]pyrazine

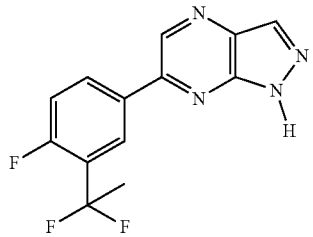 [SMILES: CC(F)(F)c1cc(-c2cnc3cn[nH]c3n2)ccc1F]

The title compound was prepared in a manner analogous to Intermediate 2 using 2-(4-fluoro-3-(1,1-difluoroethyl) phenyl)-4,4,5,5-tetramethyl-1,3,2-dioxaborolane instead of 2-(3-(difluoromethyl)-4-fluorophenyl)-4,4,5,5-tetramethyl-1,3,2-dioxaborolane in Step A. MS (ESI): mass calcd. for $C_{13}H_9F_3N_4$, 278.1; m/z found, 279.1 [M+H]$^+$.

Intermediate 12: 2-(6-(4-Chloro-3-(1,1-difluoro-ethyl)phenyl)-1H-pyrazolo[4,3-b]pyridin-1-yl)acetic acid

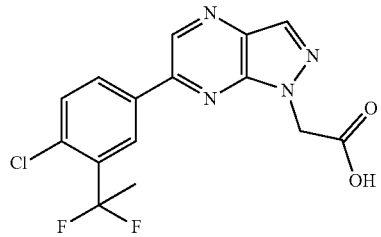 [SMILES: CC(F)(F)c1cc(-c2cnc3cnn(CC(=O)O)c3n2)ccc1Cl]

Step A: Ethyl 2-(6-(4-chloro-3-(1,1-difluoroethyl)phenyl)-1H-pyrazolo[4,3-b]pyridin-1-yl)acetate. The title compound was prepared in a manner analogous to Intermediate 1, Step B, using 6-(4-chloro-3-(1,1-difluoroethyl)phenyl)-1H-pyrazolo[3,4-b]pyrazine (Intermediate 10) instead of 6-chloro-1H-pyrazolo[3,4-b]pyrazine and ethyl 2-chloroacetate instead of SEM-Chloride. MS (ESI): mass calcd. for $C_{17}H_{14}ClF_2N_4O_2$, 380.1; m/z found, 381.1 [M+H]$^+$.

Step B: 2-(6-(4-Chloro-3-(1,1-difluoroethyl)phenyl)-1H-pyrazolo[4,3-b]pyridin-1-yl)acetic acid. A solution of ethyl 2-(6-(4-chloro-3-(1,1-difluoroethyl)phenyl)-1H-pyrazolo[4,3-b]pyridin-1-yl)acetate (41 mg, 0.107 mmol) in THF/EtOH/H$_2$O (1:1:1, 6 mL) was charged with LiOH (10 mg, 0.429 mmol). The resulting solution was stirred at r.t. overnight. The completed reaction was concentrated and re-suspended in water. The mixture was acidified with 1N HCl and extracted into EtOAc (3×2 mL). The organic layer was dried over Na$_2$SO$_4$, filtered and concentrated to give the title compound (37 mg, 98%). MS (ESI): mass calcd. for $C_{15}H_{11}ClF_2N_4O_2$, 352.1; m/z found, 353.1 [M+H]$^+$.

Intermediate 13: 2-(6-(3-(Difluoromethoxy)-4-fluorophenyl)-1H-pyrazolo[4,3-b]pyridin-1-yl)acetic acid

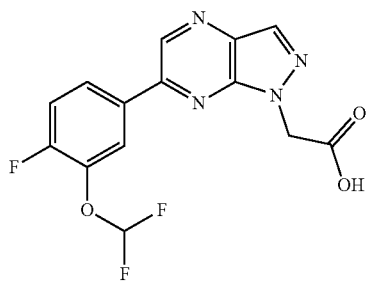

Step A: Ethyl 2-(6-(3-(difluoromethoxy)-4-fluorophenyl)-1H-pyrazolo[3,4-b]pyrazin-1-yl)acetate. The title compound was prepared in a manner analogous to Intermediate 1, Step B, using 6-(3-(difluoromethoxy)-4-fluorophenyl)-1H-pyrazolo[3,4-b]pyrazine (Intermediate 8) instead of 6-chloro-1H-pyrazolo[3,4-b]pyrazine and using ethyl 2-chloroacetate instead of SEM-Chloride. MS (ESI): mass calcd. for $C_{16}H_{13}F_3N_4O_3$, 366.1; m/z found, 367.1 [M+H]$^+$.

Step B: 2-(6-(3-(Difluoromethoxy)-4-fluorophenyl)-1H-pyrazolo[4,3-b]pyridin-1-yl)acetic acid. The title compound was prepared in a manner analogous to Intermediate 12, Step B using ethyl 2-(6-(3-(difluoromethoxy)-4-fluorophenyl)-1H-pyrazolo[3,4-b]pyrazin-1-yl)acetate instead of ethyl 2-(6-(4-chloro-3-(1,1-difluoroethyl)phenyl)-1H-pyrazolo[4,3-b]pyridin-1-yl)acetate to give the title compound. MS (ESI): mass calcd. for $C_{14}H_9F_3N_4O_3$, 338.1; m/z found, 339.1.1 [M+H]$^+$.

Intermediate 14: 2-(3-(Difluoromethyl)-4-fluorophenyl)-4,4,5,5-tetramethyl-1,3,2-dioxaborolane

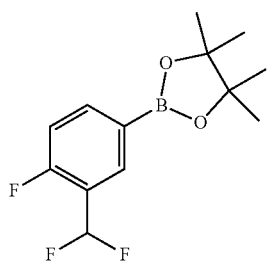 [SMILES: CC1(C)OB(c2ccc(F)c(C(F)F)c2)OC1(C)C]

A solution of 4-bromo-2-(difluoromethyl)-1-fluorobenzene (20 g, 88.9 mmol), bis(pinacolato)diboron (24.8 g, 97.8 mmol), potassium acetate (26.2 g, 267 mmol), and [1,1'-bis(diphenylphosphino)ferrocene]-dichloropalladium(II) (3.12 g, 4.44 mmol) in 1,4-dioxane (400 mL) was purged with $N_2$, and the reaction mixture was stirred at 90° C. overnight. Upon completion, the reaction mixture was cooled to room temperature, filtered through Celite®, and rinsed with EtOAc. The filtrate was washed with water and brine. The combined organics were dried with $Na_2SO_4$, filtered and concentrated to yield a clear oil (22.1 g, 81.0 mmol, 91%), which solidified upon standing. MS (ESI): mass calcd. for $C_{13}H_{16}BF_3O_2$, 272.1; m/z found, 273.0 [M+H]$^+$. $^1$H NMR (400 MHz, Chloroform-d) δ 8.12-8.00 (m, 1H), 7.96-7.85 (m, 1H), 7.17-7.06 (m, 1H), 6.88 (t, J=54.9 Hz, 1H), 1.35 (s, 12H).

Intermediate 15: 2-(3-(Difluoromethoxy)-4-fluorophenyl)-4,4,5,5-tetramethyl-1,3,2-dioxaborolane

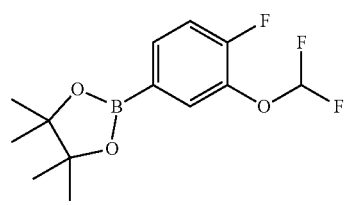 [SMILES: CC1(C)OB(c2ccc(F)c(OC(F)F)c2)OC1(C)C]

Prepared according to Intermediate 14, using 4-bromo-2-(difluoromethoxy)-1-fluorobenzene instead of 4-bromo-2-(difluoromethyl)-1-fluorobenzene. MS (ESI): mass calcd. for $C_{13}H_{16}BF_3O_3$, 288.1; m/z found, 289.0 [M+H]$^+$.

Intermediate 16: 2-(3-(Difluoromethoxy)-4-chlorophenyl)-4,4,5,5-tetramethyl-1,3,2-dioxaborolane

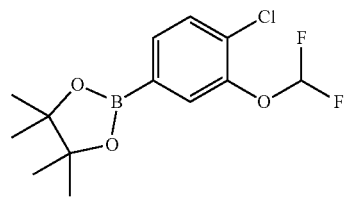 [SMILES: CC1(C)OB(c2ccc(Cl)c(OC(F)F)c2)OC1(C)C]

Prepared according to Intermediate 14, using 4-bromo-1-chloro-2-(difluoromethoxy)benzene instead of 4-bromo-2-(difluoromethyl)-1-fluorobenzene. $^1$H NMR (500 MHz, CDCl$_3$) δ 7.62-7.56 (m, 2H), 7.44 (d, J=7.9 Hz, 1H), 6.56 (t, J=73.6 Hz, 1H), 1.34 (s, 12H).

Intermediate 17: 2-(4-Chloro-3-(1,1-difluoroethyl)phenyl)-4,4,5,5-tetramethyl-1,3,2-dioxaborolane

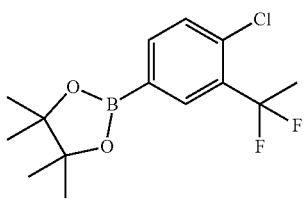 [SMILES: CC(F)(F)c1cc(B2OC(C)(C)C(C)(C)O2)ccc1Cl]

Prepared according to Intermediate 18, using 1-(5-bromo-2-chlorophenyl)ethan-1-one instead of 1-(5-bromo-2-fluorophenyl)-1-ethanone in step A. $^1$H NMR (500 MHz, CDCl3) δ 8.02 (d, J=1.5 Hz, 1H), 7.79-7.71 (m, 1H), 7.47-7.39 (m, 1H), 2.03 (t, J=18.4 Hz, 3H), 1.34 (s, 12H).

Intermediate 18: 2-(4-Fluoro-3-(1,1-difluoroethyl) phenyl)-4,4,5,5-tetramethyl-1,3,2-dioxaborolane

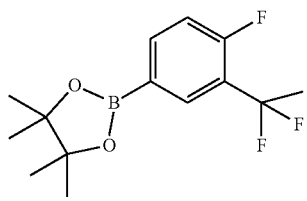 [SMILES: CC(F)(F)c1cc(B2OC(C)(C)C(C)(C)O2)ccc1F]

Step A: 4-Bromo-2-(1,1-difluoroethyl)-1-fluorobenzene. In a round bottom flask, a mixture of 1-(5-bromo-2-fluorophenyl)-1-ethanone (2.5 g, 11.5 mmol, 1 equiv) and DAST (1.9 mL, 14.4 mmol, 1.25 equiv) was heated at 60° C. for 16 h. Then a sat. aq. solution of NaHCO$_3$ was slowly added at 0° C. and extracted with DCM. The organic layers were combined, dried over MgSO$_4$, filtered, and partially concentrated (product is volatile). The crude product was purified by flash column chromatography (silica; 100% DCM) to give the title compound (3 g, 7.5 mmol, purity 60%, 65%) as a brown oil. $^1$H NMR (300 MHz, CDCl$_3$) δ 7.73-7.61 (m, 1H), 7.60-7.48 (m, 1H), 7.02 (t, J=9.4 Hz, 1H), 1.98 (t, J=18.6 Hz, 3H).

Step B: 2-(3-(1,1-Difluoroethyl)-4-fluorophenyl)-4,4,5,5-tetramethyl-1,3,2-dioxaborolane. In a round bottom flask, bis(pinacolato)diboron (2.87 g, 11.3 mmol, 1.5 equiv), potassium acetate (2.22 g, 22.6 mmol, 3 equiv), and [1,1'-bis(diphenylphosphino)ferrocene]-dichloropalladium(II) (615 mg, 0.75 mmol, 0.1 equiv) were added to a solution of 4-bromo-2-(1,1-difluoroethyl)-1-fluorobenzene (3 g, 7.5 mmol, 1 equiv) in dry 1,4-dioxane (40 mL). The mixture was purged with nitrogen and stirred at 90° C. for 16 h. Then, a sat. aq. solution of NaHCO$_3$ was added and the mixture was extracted with EtOAc. The combined organics were dried with MgSO$_4$, filtered and concentrated to yield a brown oil (2.15 g, 7.53 mmol), which was used in the next step without further purification. MS (ESI): mass calcd. for C$_{14}$H$_{18}$BF$_3$O$_2$, 286.1; m/z found, 287.1 [M+H]$^+$.

Intermediate 19: 2-(4-Chloro-3-(difluoromethyl) phenyl)-4,4,5,5-tetramethyl-1,3,2-dioxaborolane

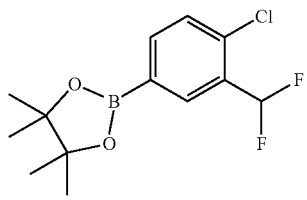

Prepared according to Intermediate 18, using 5-bromo-2-chlorobenzaldehyde instead of 1-(5-bromo-2-fluorophenyl)-1-ethanone in step A. MS (ESI): mass calcd. for C$_{13}$H$_{16}$BClF$_2$O$_2$, 288.1; m/z found, 289.1 [M+H]$^+$.

Example 1: 1-[6-[3-(Difluoromethyl)-4-fluoro-phenyl]pyrazolo[3,4-b]pyrazin-1-yl]butan-2-one

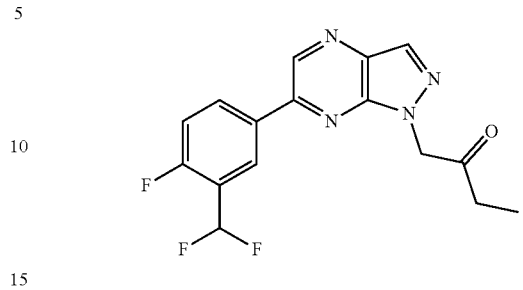

To a solution of 6-(3-(difluoromethyl)-4-fluorophenyl)-1H-pyrazolo[3,4-b]pyrazine (Intermediate 2, 35 mg, 0.13 mmol) and cesium carbonate (84.7 mg, 0.26 mmol) in DMF (2.3 mL) was added 1-bromobutan-2-one (44.2 mg, 0.29 mmol). The reaction mixture was stirred at 60° C. overnight. The reaction mixture was cooled, diluted with water, and extracted into EtOAc. The organic layer was separated, dried (Na$_2$SO$_4$), filtered, and concentrated under reduced pressure. Purification (FCC, SiO$_2$, 0-50% EtOAc/Hexanes) afforded the title compound a white solid (8.3 mg, 18.7%). MS (ESI): mass calcd. for C$_{16}$H$_{13}$F$_3$N$_4$O, 334.1; m/z found, 335.0 [M+H]$^+$. $^1$H NMR (400 MHz, CDCl$_3$) δ 9.07 (s, 1H), 8.42-8.30 (m, 2H), 8.26-8.18 (m, 1H), 7.35-7.27 (m, 1H), 6.99 (t, J=54.8 Hz, 1H), 5.37 (s, 2H), 2.59-2.48 (m, 2H), 1.18-1.10 (m, 3H).

Example 2: 2-[6-[4-Chloro-3-(difluoromethoxy) phenyl]pyrazolo[3,4-b]pyrazin-1-yl]-1-cyclopropyl-ethanone

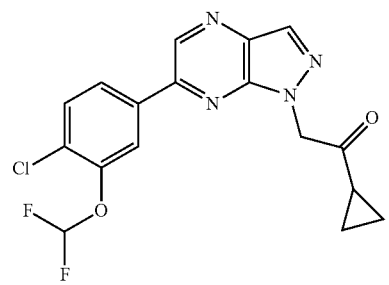 [SMILES: O=C(Cn1ncc2ncc(-c3ccc(Cl)c(OC(F)F)c3)nc21)C1CC1]

To a cooled, 0° C., solution of NaH (60% dispersion in mineral oil, 4.8 mg, 0.12 mmol) in DMF (5.8 mL) under nitrogen, was added 6-(3-(difluoromethoxy)-4-chlorophenyl)-1H-pyrazolo[3,4-b]pyrazine (Intermediate 9, 30 mg, 0.10 mmol) dissolved in DMF (3 mL). The reaction mixture was stirred at room temperature for 30 minutes. 2-Bromo-1-cyclopropylethanone (0.111 mmol) was added to the reaction mixture and the reaction was stirred at room temperature overnight. The reaction mixture was diluted with water, and extracted into EtOAc (3×). The organic layers were combined, washed with brine, dried (Na$_2$SO$_4$), filtered, and concentrated under reduced pressure. Purification (FCC, SiO$_2$, 0-80% EtOAc/Hexanes) afforded the title compound (11.7 mg, 31%). MS (ESI): mass calcd. for C$_{17}$H$_{13}$ClF$_2$N$_4$O$_2$, 378.1; m/z found, 379.0 [M+H]$^+$. $^1$H NMR (500 MHz, CDCl$_3$) δ 9.04 (s, 1H), 8.38 (s, 1H), 8.07-8.00 (m, 1H), 7.97-7.86 (m, 1H), 7.61 (d, J=8.4 Hz, 1H), 6.65 (t, J=73.1 Hz, 1H), 5.54 (s, 2H), 2.07-1.91 (m, 1H), 1.30-1.14 (m, 2H), 1.09-0.96 (m, 2H).

Example 3: N,N-Dimethyl-2-[6-[5-(trifluoromethyl)-2-thienyl]pyrazolo[3,4-b]pyrazin-1-yl]acetamide

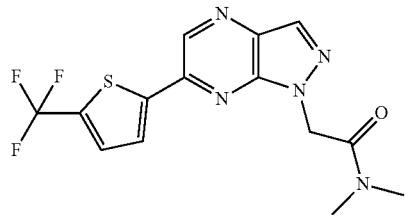 [SMILES: CN(C)C(=O)Cn1ncc2ncc(-c3ccc(C(F)(F)F)s3)nc21]

A solution of 2-(6-chloro-1H-pyrazolo[3,4-b]pyrazin-1-yl)-N,N-dimethylacetamide (Intermediate 3, 15 mg, 0.06 mmol), sodium carbonate (20 mg, 0.18 mmol), (5-(trifluoromethyl)thiophen-2-yl)boronic acid (14.7 mg, 0.075 mmol), and Pd(dppf)Cl$_2$ (5.9 mg, 0.008 mmol), in THF (2.0 mL) and water (0.5 mL), under nitrogen, was stirred at 80° C., overnight. The reaction mixture was diluted with water (30 mL) and extracted with EtOAc (3×10 mL). The combined organics were dried over Na$_2$SO$_4$, filtered and concentrated under reduced pressure. Purification (FCC, SiO$_2$, 0-100% EtOAc/Hexanes) afforded the title compound (16 mg, 72%). MS (ESI): mass calcd. for C$_{14}$H$_{12}$F$_3$N$_5$OS, 355.1; m/z found, 356.1 [M+H]$^+$. $^1$H NMR (500 MHz, CDCl$_3$) δ 9.04 (s, 1H), 8.38 (s, 1H), 8.07-8.00 (m, 1H), 7.97-7.86 (m, 1H), 7.61 (d, J=8.4 Hz, 1H), 6.65 (t, J=73.1 Hz, 1H), 5.54 (s, 2H), 2.07-1.91 (m, 1H), 1.30-1.14 (m, 2H), 1.09-0.96 (m, 2H).

Example 4: N,N-Dimethyl-2-[6-(m-tolyl)pyrazolo[3,4-b]pyrazin-1-yl]acetamide

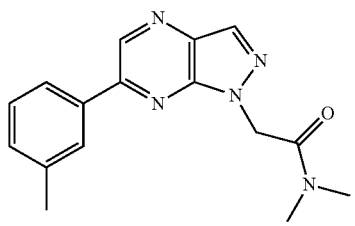 [SMILES: Cc1cccc(-c2cnc3cnn(CC(=O)N(C)C)c3n2)c1]

The title compound was prepared in a manner analogous to Example 3, using 3-methylphenylboronic acid instead of (5-(trifluoromethyl)thiophen-2-yl)boronic acid. MS (ESI): mass calcd. for C$_{16}$H$_{17}$N$_5$O, 295.1; m/z found, 296.2 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 5: 2-[6-(4-Chloro-3-fluoro-phenyl)pyrazolo[3,4-b]pyrazin-1-yl]-N,N-dimethylacetamide

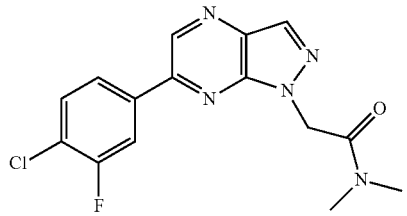 [SMILES: CN(C)C(=O)Cn1ncc2ncc(-c3ccc(Cl)c(F)c3)nc21]

The title compound was prepared in a manner analogous to Example 3, using 4-chloro-3-fluorophenylboronic acid instead of (5-(trifluoromethyl)thiophen-2-yl)boronic acid. MS (ESI): mass calcd. for C$_{15}$H$_{13}$ClFN$_5$O, 333.1; m/z found, 334.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 6: 2-[6-(3-Fluoro-4-methyl-phenyl)pyrazolo[3,4-b]pyrazin-1-yl]-N,N-dimethylacetamide

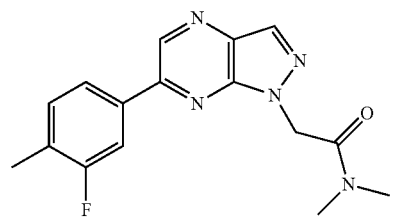

The title compound was prepared in a manner analogous to Example 3, using 3-fluoro-4-methylphenylboronic acid instead of (5-(trifluoromethyl)thiophen-2-yl)boronic acid. MS (ESI): mass calcd. for C$_{16}$H$_{16}$FN$_5$O, 313.1; m/z found, 314.2 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 7: 2-[6-(4-Chloro-3-methyl-phenyl)pyrazolo[3,4-b]pyrazin-1-yl]-N,N-dimethylacetamide

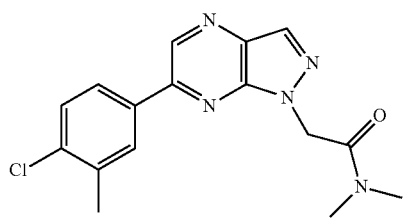 [SMILES: Cc1cc(-c2cnc3cnn(CC(=O)N(C)C)c3n2)ccc1Cl]

The title compound was prepared in a manner analogous to Example 3 using 4-chloro-3-methylphenylboronic acid instead of (5-(trifluoromethyl)thiophen-2-yl)boronic acid. MS (ESI): mass calcd. for C$_{16}$H$_{16}$ClN$_5$O, 329.1; m/z found, 330.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 8: 2-[6-(3-Chloro-4-methoxy-phenyl)pyrazolo[3,4-b]pyrazin-1-yl]-N,N-dimethylacetamide

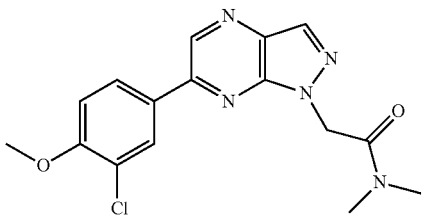

The title compound was prepared in a manner analogous to Example 3 using 3-chloro-4-methoxyphenylboronic acid instead of (5-(trifluoromethyl)thiophen-2-yl)boronic acid. MS (ESI): mass calcd. for $C_{16}H_{16}ClN_5O_2$, 345.1; m/z found, 346.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 9: 2-[6-[3-(Difluoromethyl)-4-fluoro-phenyl]pyrazolo[3,4-b]pyrazin-1-yl]-N,N-dimethyl-acetamide

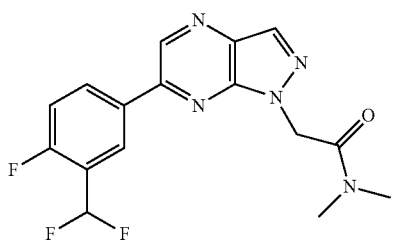 [SMILES: CN(C)C(=O)Cn1ncc2ncc(-c3ccc(F)c(C(F)F)c3)nc21]

The title compound was prepared in a manner analogous to Example 1 using 2-chloro-N,N-dimethylacetaminde instead of 1-bromobutan-2-one. MS (ESI): mass calcd. for $C_{16}H_{14}F_3N_5O$, 349.1; m/z found, 350.1 [M+H]$^+$. $^1$H NMR (500 MHz, DMSO-d$_6$) δ 9.34 (s, 1H), 8.53 (s, 1H), 8.52-8.47 (m, 2H), 7.66-7.56 (m, 1H), 7.32 (t, J=54.1 Hz, 1H), 5.55 (s, 2H), 3.17 (s, 3H), 2.85 (s, 3H).

Example 10: 2-[6-[3-(Difluoromethyl)-4-fluoro-phenyl]-3-fluoro-pyrazolo[3,4-b]pyrazin-1-yl]-N,N-dimethyl-acetamide

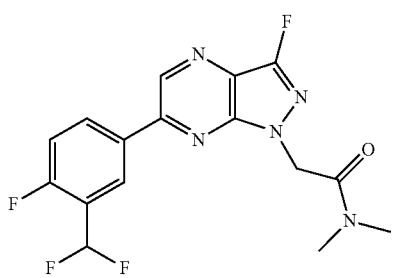 [SMILES: CN(C)C(=O)Cn1nc(F)c2ncc(-c3ccc(F)c(C(F)F)c3)nc21]

The title compound was prepared in a manner analogous to Example 1 using 6-(3-(difluoromethyl)-4-fluorophenyl)-3-fluoro-1H-pyrazolo[3,4-b]pyrazine (Intermediate 7) instead of 6-(3-(difluoromethyl)-4-fluorophenyl)-1H-pyrazolo[3,4-b]pyrazine (Intermediate 2) and 2-chloro-N,N-dimethylacetaminde instead of 1-bromobutan-2-one. MS (ESI): mass calcd. for $C_{16}H_{13}F_4N_5O$, 367.1; m/z found, 368.1 [M+H]$^+$. $^1$H NMR (500 MHz, DMSO-d$_6$) δ 9.41 (s, 1H), 8.58-8.48 (m, 2H), 7.67-7.59 (m, 1H), 7.33 (t, J=54.0 Hz, 1H), 5.46 (s, 2H), 3.14 (s, 3H), 2.84 (s, 3H).

Example 11: 2-[6-[4-Chloro-3-(difluoromethyl)phenyl]pyrazolo[3,4-b]pyrazin-1-yl]-N,N-dimethyl-acetamide

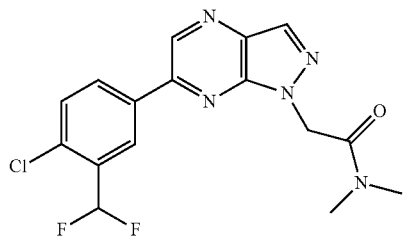 [SMILES: CN(C)C(=O)Cn1ncc2ncc(-c3ccc(Cl)c(C(F)F)c3)nc21]

The title compound was prepared in a manner analogous to Example 3, using 2-(4-chloro-3-(difluoromethyl)phenyl)-4,4,5,5-tetramethyl-1,3,2-dioxaborolane instead of (5-(trifluoromethyl)thiophen-2-yl)boronic acid MS (ESI): mass calcd. for $C_{16}H_{14}ClF_2N_5O$, 365.1; m/z found, 366.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 12: 2-[6-[3-(1,1-Difluoroethyl)-4-fluorophenyl]pyrazolo[3,4-b]pyrazin-1-yl]-N,N-dimethyl-acetamide

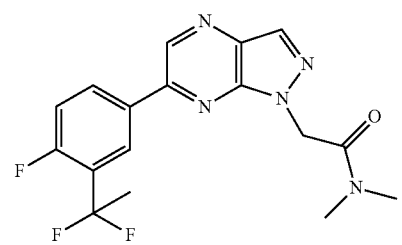 [SMILES: CN(C)C(=O)Cn1ncc2ncc(-c3ccc(F)c(C(C)(F)F)c3)nc21]

The title compound was prepared in a manner analogous to Example 2 using 6-(4-fluoro-3-(1,1-difluoroethyl)phenyl)-1H-pyrazolo[3,4-b]pyrazine (Intermediate 11) instead of 6-(3-(difluoromethoxy)-4-chlorophenyl)-1H-pyrazolo[3,4-b]pyrazine (Intermediate 9) and 2-chloro-N,N-dimethylacetamide instead of 2-bromo-1-cyclopropylethanone. MS (ESI): mass calcd. for C$_{17}$H$_{16}$F$_3$N$_5$O, 363.1; m/z found, 364.2 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 13: 2-[6-[4-Chloro-3-(1,1-difluoroethyl)phenyl]pyrazolo[3,4-b]pyrazin-1-yl]-N,N-dimethyl-acetamide

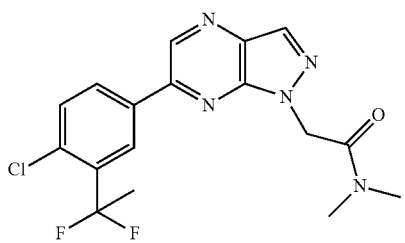 [SMILES: CN(C)C(=O)Cn1ncc2ncc(-c3ccc(Cl)c(C(C)(F)F)c3)nc21]

The title compound was prepared in a manner analogous to Example 2 using 6-(4-chloro-3-(1,1-difluoroethyl)phenyl)-1H-pyrazolo[3,4-b]pyrazine (Intermediate 10) instead of 6-(3-(difluoromethoxy)-4-chlorophenyl)-1H-pyrazolo[3,4-b]pyrazine (Intermediate 9) and 2-chloro-N,N-dimethyl-acetaminde instead of 2-bromo-1-cyclopropylethanone. MS (ESI): mass calcd. for C$_{17}$H$_{16}$ClF$_2$N$_5$O, 379.1; m/z found, 380.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 14: 2-[6-[4-Chloro-3-(trifluoromethyl)phenyl]pyrazolo[3,4-b]pyrazin-1-yl]-N,N-dimethyl-acetamide

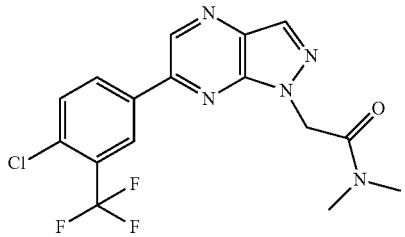 [SMILES: CN(C)C(=O)Cn1ncc2ncc(-c3ccc(Cl)c(C(F)(F)F)c3)nc21]

The title compound was prepared in a manner analogous to Example 3 using [4-chloro-3-(trifluoromethyl)phenyl]boronic acid instead of (5-(trifluoromethyl)thiophen-2-yl)boronic acid. MS (ESI): mass calcd. for C$_{16}$H$_{13}$ClF$_3$N$_5$O, 383.1; m/z found, 384.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 15: 2-[6-[3-(Difluoromethoxy)-4-fluoro-phenyl]pyrazolo[3,4-b]pyrazin-1-yl]-N,N-dimethyl-acetamide

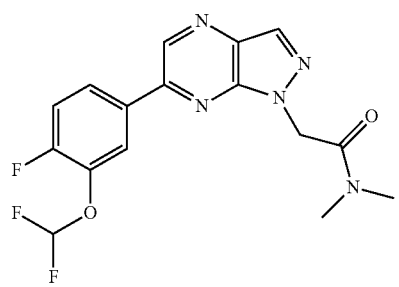 [SMILES: CN(C)C(=O)Cn1ncc2ncc(-c3ccc(F)c(OC(F)F)c3)nc21]

The title compound was prepared in a manner analogous to Intermediate 3 using 6-(3-(difluoromethoxy)-4-fluoro-phenyl)-1H-pyrazolo[3,4-b]pyrazine (Intermediate 8) instead of 6-chloro-1H-pyrazolo[3,4-b]pyrazine. MS (ESI): mass calcd. for C$_{16}$H$_{14}$F$_3$N$_5$O$_2$, 365.1; m/z found, 366.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 16: 2-[6-[4-(Difluoromethoxy)-3-fluoro-phenyl]pyrazolo[3,4-b]pyrazin-1-yl]-N,N-dimethyl-acetamide

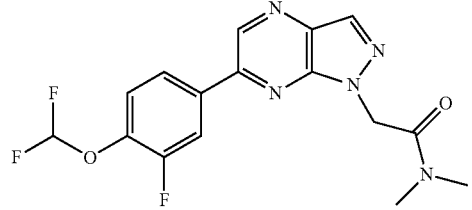 [SMILES: CN(C)C(=O)Cn1ncc2ncc(-c3ccc(OC(F)F)c(F)c3)nc21]

The title compound was prepared in a manner analogous to Example 3 using 2-[4-(difluoromethoxy)-3-fluorophenyl]-4,4,5,5-tetramethyl-1,3,2-dioxaborolane instead of (5-(trifluoromethyl)thiophen-2-yl)boronic acid. MS (ESI): mass calcd. for C$_{16}$H$_{14}$F$_3$N$_5$O$_2$, 365.1; m/z found, 366.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 17: 2-[6-[4-Chloro-3-(difluoromethoxy)phenyl]pyrazolo[3,4-b]pyrazin-1-yl]-N,N-dimethylacetamide

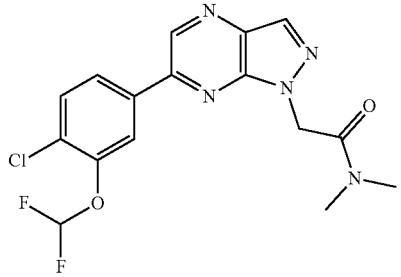 [SMILES: CN(C)C(=O)Cn1ncc2ncc(-c3ccc(Cl)c(OC(F)F)c3)nc21]

The title compound was prepared in a manner analogous to Example 2 using 2-chloro-N,N-dimethylacetaminde instead of 2-bromo-1-cyclopropylethanone. MS (ESI): mass calcd. for $C_{16}H_{14}ClF_2N_5O_2$, 381.1; m/z found, 382.0 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 18: 2-[6-[3-Chloro-4-(trifluoromethoxy)phenyl]pyrazolo[3,4-b]pyrazin-1-yl]-N,N-dimethylacetamide

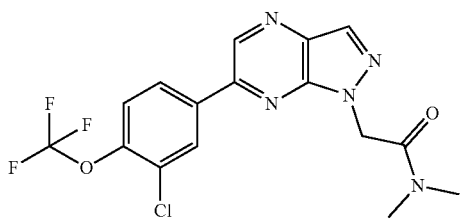 [SMILES: CN(C)C(=O)Cn1ncc2ncc(-c3ccc(OC(F)(F)F)c(Cl)c3)nc21]

The title compound was prepared in a manner analogous to Example 3 using 3-chloro-4-(trifluoromethoxy)phenylboronic acid instead of (5-(trifluoromethyl)thiophen-2-yl)boronic acid. MS (ESI): mass calcd. for $C_{16}H_{13}ClF_3N_5O_2$, 399.1; m/z found, 400.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 19: 2-[6-(3,5-Difluoro-4-methyl-phenyl)pyrazolo[3,4-b]pyrazin-1-yl]-N,N-dimethyl-acetamide

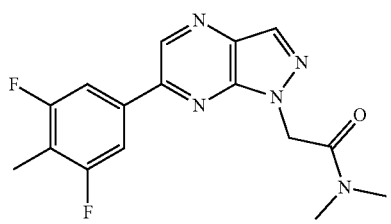

The title compound was prepared in a manner analogous to Example 3 using 3,5-difluoro-4-methylphenylboronic acid instead of (5-(trifluoromethyl)thiophen-2-yl)boronic acid. MS (ESI): mass calcd. for $C_{16}H_{15}F_2N_5O$, 331.1; m/z found, 332.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 20: 2-[6-(2,4-Difluoro-3-methyl-phenyl)pyrazolo[3,4-b]pyrazin-1-yl]-N,N-dimethyl-acetamide

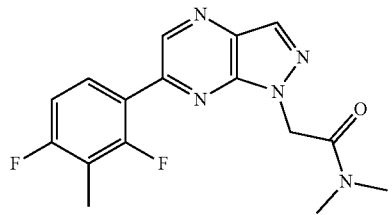 [SMILES: Cc1c(F)ccc(-c2cnc3cnn(CC(=O)N(C)C)c3n2)c1F]

The title compound was prepared in a manner analogous to Example 3 using (2,4-difluoro-3-methylphenyl)boronic acid instead of (5-(trifluoromethyl)thiophen-2-yl)boronic acid. MS (ESI): mass calcd. for $C_{16}H_{15}F_2N_5O$, 331.1; m/z found, 332.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 21: N,N-Dimethyl-2-[6-(3,4,5-trifluorophenyl)pyrazolo[3,4-b]pyrazin-1-yl]acetamide

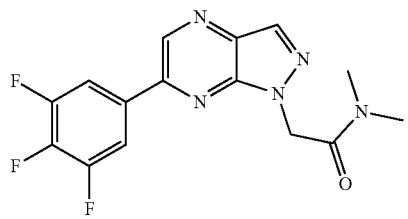 [SMILES: CN(C)C(=O)Cn1ncc2ncc(-c3cc(F)c(F)c(F)c3)nc21]

The title compound was prepared in a manner analogous to Example 3 using 3,4,5-trifluorophenylboronic acid instead of (5-(trifluoromethyl)thiophen-2-yl)boronic acid. MS (ESI): mass calcd. for $C_{15}H_{12}F_3N_5O$, 335.1; m/z found, 336.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 22: N,N-Dimethyl-2-[6-(2,3,4-trifluorophenyl)pyrazolo[3,4-b]pyrazin-1-yl]acetamide

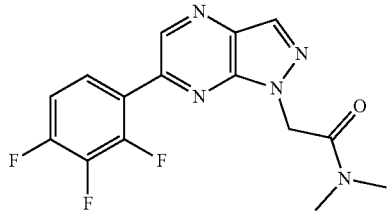 [SMILES: CN(C)C(=O)Cn1ncc2ncc(-c3ccc(F)c(F)c3F)nc21]

The title compound was prepared in a manner analogous to Example 3 using 2,3,4-trifluorophenylboronic acid instead of (5-(trifluoromethyl)thiophen-2-yl)boronic acid. MS (ESI): mass calcd. for $C_{15}H_{12}F_3N_5O$, 335.1; m/z found, 336.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 23: 1-(Azetidin-1-yl)-2-[6-[3-(difluoromethyl)-4-fluoro-phenyl]pyrazolo[3,4-b]pyrazin-1-yl]ethanone

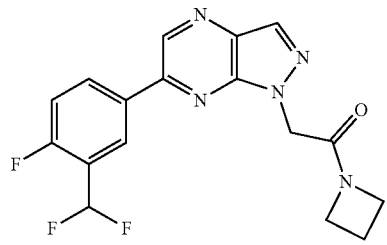 [SMILES: O=C(Cn1ncc2ncc(-c3ccc(F)c(C(F)F)c3)nc21)N1CCC1]

A mixture of 6-(3-(difluoromethyl)-4-fluorophenyl)-1H-pyrazolo[3,4-b]pyrazine (Intermediate 2, 60 mg, 0.227 mmol), 1-(azetidin-1-yl)-2-bromoethan-1-one (44 mg, 0.247 mmol), and Cs$_2$CO$_3$ (148 mg, 0.454 mmol) in DMF (1 mL) was stirred at r.t. for 1 hour. The completed reaction mixture was diluted with water (5 mL) and extracted with EtOAc (3×3 mL). The combined organics were dried over Na$_2$SO$_4$, filtered and concentrated under reduced pressure. The crude material was purified (FCC, SiO$_2$, 0-50% EtOAc in hexanes) to afford the title compound (33 mg, 40%). MS (ESI): mass calcd. for $C_{17}H_{14}F_3N_5O$, 361.1; m/z found, 362.1 [M+H]$^+$. $^1$H NMR (300 MHz, DMSO-d$_6$) δ 9.36 (s, 1H), 8.61-8.43 (m, 2H), 8.54 (s, 1H), 7.68-7.57 (m, 1H), 7.34 (t, J=54.1 Hz, 1H), 5.26 (s, 2H), 4.38-4.22 (m, 2H), 3.99-3.84 (m, 2H), 2.38-2.19 (m, 2H).

Example 24: 1-(Azetidin-1-yl)-2-[6-[3-(difluoromethyl)-4-fluoro-phenyl]-3-fluoro-pyrazolo[3,4-b]pyrazin-1-yl]ethanone

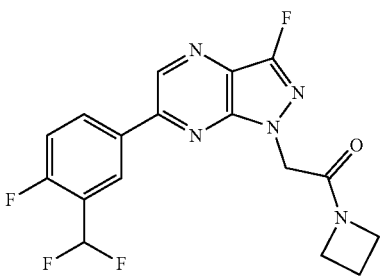 [SMILES: O=C(Cn1nc(F)c2ncc(-c3ccc(F)c(C(F)F)c3)nc21)N1CCC1]

The title compound was prepared in a manner analogous to Example 1 using 6-(3-(difluoromethyl)-4-fluorophenyl)-3-fluoro-1H-pyrazolo[3,4-b]pyrazine (Intermediate 7) instead of 6-(3-(difluoromethyl)-4-fluorophenyl)-1H-pyrazolo[3,4-b]pyrazine (Intermediate 2) and N-bromoacetylazetidine instead of 1-bromobutan-2-one. MS (ESI): mass calcd. for $C_{17}H_{13}F_4N_5O$, 379.1; m/z found, 380.1[M+H]$^+$. $^1$H NMR (300 MHz, DMSO-d$_6$) δ 9.43 (s, 1H), 8.65-8.47 (m, 2H), 7.72-7.59 (m, 1H), 7.34 (t, J=54.0 Hz, 1H), 5.18 (s, 2H), 4.39-4.22 (m, 2H), 3.99-3.83 (m, 2H), 2.36-2.21 (m, 2H).

Example 25: 1-(Azetidin-1-yl)-2-[6-[4-chloro-3-(1,1-difluoroethyl)phenyl]pyrazolo[3,4-b]pyrazin-1-yl]ethanone

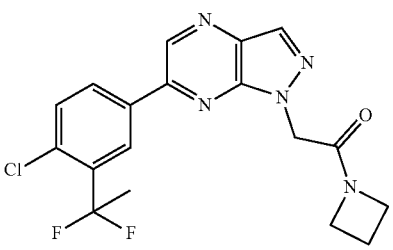 [SMILES: CC(F)(F)c1cc(-c2cnc3cnn(CC(=O)N4CCC4)c3n2)ccc1Cl]

The title compound was prepared in a manner analogous to Example 2 using 6-(4-chloro-3-(1,1-difluoroethyl)phenyl)-1H-pyrazolo[3,4-b]pyrazine (Intermediate 10) instead of 6-(3-(difluoromethoxy)-4-chlorophenyl)-1H-pyrazolo[3,4-b]pyrazine (Intermediate 9) and 1-(azetidin-1-yl)-2-bromoethan-1-one instead of 2-bromo-1-cyclopropylethanone. MS (ESI): mass calcd. for $C_{18}H_{16}ClF_2N_5O$, 391.1; m/z found, 392.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 26: 1-(Azetidin-1-yl)-2-[6-[3-(1,1-difluoroethyl)-4-fluoro-phenyl]pyrazolo[3,4-b]pyrazin-1-yl]ethanone

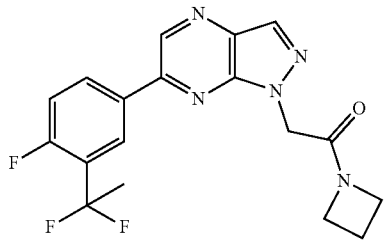 [SMILES: CC(F)(F)c1cc(-c2cnc3cnn(CC(=O)N4CCC4)c3n2)ccc1F]

The title compound was prepared in a manner analogous to Example 2 using 6-(4-fluoro-3-(1,1-difluoroethyl)phenyl)-1H-pyrazolo[3,4-b]pyrazine (Intermediate 11) instead 6-(3-(difluoromethoxy)-4-chlorophenyl)-1H-pyrazolo[3,4-b]pyrazine (Intermediate 9) and 1-azetidin-1-yl-2-chloroethanone instead of 2-bromo-1-cyclopropylethanone. MS (ESI): mass calcd. for $C_{18}H_{16}F_3N_5O$, 375.1; m/z found, 376.2 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 27: 1-(Azetidin-1-yl)-2-[6-[3-(difluoromethoxy)-4-fluoro-phenyl]pyrazolo[3,4-b]pyrazin-1-yl]ethanone

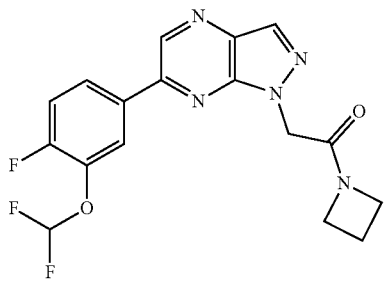 [SMILES: O=C(Cn1ncc2ncc(-c3ccc(F)c(OC(F)F)c3)nc21)N1CCC1]

The title compound was prepared in a manner analogous to Example 1 using 6-(3-(difluoromethoxy)-4-fluorophenyl)-1H-pyrazolo[3,4-b]pyrazine (Intermediate 8) instead of 6-(3-(difluoromethyl)-4-fluorophenyl)-1H-pyrazolo[3,4-b]pyrazine (Intermediate 2), and using 1-(azetidin-1-yl)-2-bromoethan-1-one instead of 1-bromobutan-2-one. MS (ESI): mass calcd. for $C_{17}H_{14}F_3N_5O_2$, 377.1; m/z found, 378.1 [M+H]$^+$. $^1$H NMR (500 MHz, CDCl$_3$) δ 9.02 (s, 1H), 8.35 (s, 1H), 8.14-8.02 (m, 1H), 8.01-7.92 (m, 1H), 7.41-7.30 (m, 1H), 6.66 (t, J=73.2 Hz, 1H), 5.17 (s, 2H), 4.20 (t, J=7.7 Hz, 2H), 4.12 (t, J=7.8 Hz, 2H), 2.46-2.27 (m, 2H).

Example 28: 1-(Azetidin-1-yl)-2-[6-[4-chloro-3-(difluoromethoxy)phenyl]pyrazolo[3,4-b]pyrazin-1-yl]ethanone

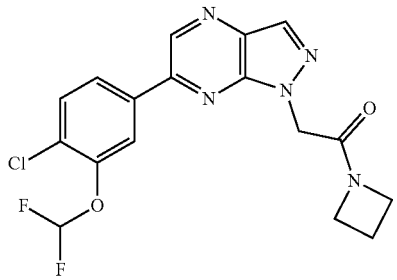 [SMILES: O=C(Cn1ncc2ncc(-c3ccc(Cl)c(OC(F)F)c3)nc21)N1CCC1]

The title compound was prepared in a manner analogous to Example 2, using 1-azetidin-1-yl-2-chloro-ethanone instead of 2-bromo-1-cyclopropylethanone. MS (ESI): mass calcd. for $C_{17}H_{14}ClF_2N_5O_2$, 393.1; m/z found, 394.0 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 29: 2-[6-[3-(Difluoromethyl)-4-fluoro-phenyl]pyrazolo[3,4-b]pyrazin-1-yl]-1-(3-methylazetidin-1-yl)ethanone

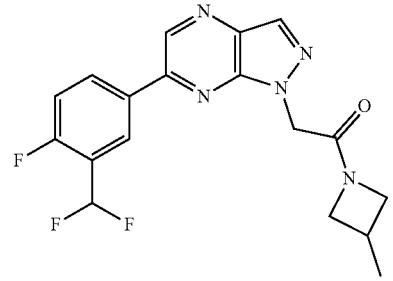 [SMILES: CC1CN(C(=O)Cn2ncc3ncc(-c4ccc(F)c(C(F)F)c4)nc32)C1]

The title compound was prepared in a manner analogous to Example 1 using 2-chloro-1-(3-methylazetidin-1-yl)ethan-1-one (Intermediate 6) instead of 1-bromobutan-2-one. MS (ESI): mass calcd. for $C_{18}H_{16}F_3N_5O$, 375.1; m/z found, 376.1 [M+H]$^+$. $^1$H NMR (300 MHz, DMSO-d$_6$) δ 9.36 (s, 1H), 8.62-8.46 (m, 3H), 7.69-7.57 (m, 1H), 7.33 (t, J=54.1 Hz, 1H), 5.26 (s, 2H), 4.46-4.34 (m, 1H), 4.09-3.97 (m, 1H), 3.91-3.81 (m, 1H), 3.53-3.43 (m, 1H), 2.83-2.67 (m, 1H), 1.22 (d, J=6.9 Hz, 3H).

Example 30: 2-[6-[3-(Difluoromethyl)-4-fluorophenyl]-3-fluoro-pyrazolo[3,4-b]pyrazin-1-yl]-1-(3-methylazetidin-1-yl)ethanone

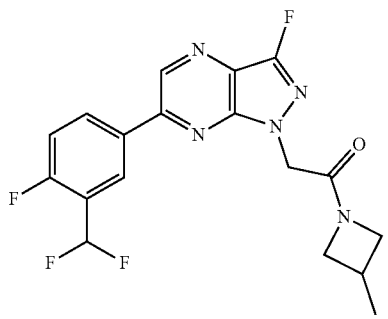 [SMILES: CC1CN(C(=O)Cn2nc(F)c3ncc(-c4ccc(F)c(C(F)F)c4)nc32)C1]

The title compound was prepared in a manner analogous to Example 1 using 6-(3-(difluoromethyl)-4-fluorophenyl)-3-fluoro-1H-pyrazolo[3,4-b]pyrazine (Intermediate 7) instead of 6-(3-(difluoromethyl)-4-fluorophenyl)-1H-pyrazolo[3,4-b]pyrazine (Intermediate 2) and 2-chloro-1-(3-methylazetidin-1-yl)ethan-1-one (Intermediate 6) instead of 1-bromobutan-2-one. MS (ESI): mass calcd. for $C_{18}H_{15}F_4N_5O$, 393.1; m/z found, 394.1 [M+H]$^+$. $^1$H NMR (500 MHz, DMSO-d$_6$) δ 9.42 (s, 1H), 8.60-8.51 (m, 2H), 7.68-7.61 (m, 1H), 7.34 (t, J=54.1 Hz, 1H), 5.18 (s, 2H), 4.44-4.36 (m, 1H), 4.05-3.99 (m, 1H), 3.90-3.83 (m, 1H), 3.51-3.44 (m, 1H), 2.81-2.70 (m, 1H), 1.22 (d, J=6.9 Hz, 3H).

Example 31: 2-[6-[3-(Difluoromethyl)-4-fluorophenyl]pyrazolo[3,4-b]pyrazin-1-yl]-1-(3-fluoroazetidin-1-yl)ethanone

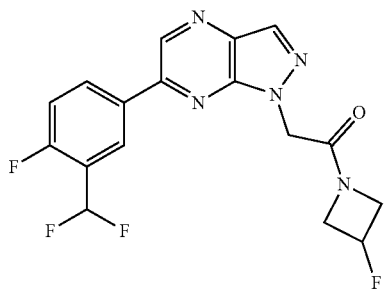 [SMILES: O=C(Cn1ncc2ncc(-c3ccc(F)c(C(F)F)c3)nc21)N1CC(F)C1]

The title compound was prepared in a manner analogous to Example 1 using 2-chloro-1-(3-fluoroazetidin-1-yl)ethan-1-one (Intermediate 4) instead of 1-bromobutan-2-one. MS (ESI): mass calcd. for $C_{17}H_{13}F_4N_5O$, 379.1; m/z found, 380.1 [M+H]$^+$. $^1$H NMR (500 MHz, DMSO-d$_6$) δ 9.36 (s, 1H), 8.55 (s, 1H), 8.54-8.49 (m, 2H), 7.67-7.59 (m, 1H), 7.33 (t, J=54.1 Hz, 1H), 5.55-5.38 (m, 1H), 5.37 (d, J=16.9 Hz, 1H), 5.32 (d, J=16.8 Hz, 1H), 4.71-4.59 (m, 1H), 4.48-4.35 (m, 1H), 4.32-4.20 (m, 1H), 4.05-3.92 (m, 1H).

Example 32: 2-[6-[3-(Difluoromethyl)-4-fluorophenyl]-3-fluoro-pyrazolo[3,4-b]pyrazin-1-yl]-1-(3-fluoroazetidin-1-yl)ethanone

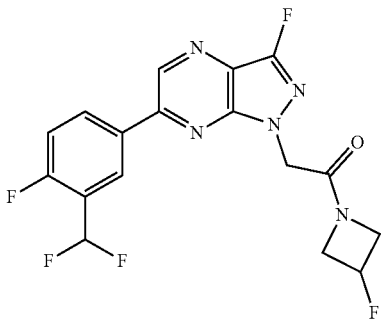 [SMILES: O=C(Cn1nc(F)c2ncc(-c3ccc(F)c(C(F)F)c3)nc21)N1CC(F)C1]

The title compound was prepared in a manner analogous to Example 1, using 6-(3-(difluoromethyl)-4-fluorophenyl)-3-fluoro-1H-pyrazolo[3,4-b]pyrazine (Intermediate 7) instead of 6-(3-(difluoromethyl)-4-fluorophenyl)-1H-pyrazolo[3,4-b]pyrazine (Intermediate 2) and 2-chloro-1-(3-fluoroazetidin-1-yl)ethan-1-one (Intermediate 5) instead of 1-bromobutan-2-one. MS (ESI): mass calcd. for $C_{17}H_{12}F_5N_5O$, 397.1; m/z found, 398.1 [M+H]$^+$. $^1$H NMR (500 MHz, DMSO-d$_6$) δ 9.42 (s, 1H), 8.58-8.48 (m, 2H), 7.70-7.59 (m, 1H), 7.33 (t, J=54.1 Hz, 1H), 5.58-5.35 (m, 1H), 5.29 (d, J=16.9 Hz, 1H), 5.24 (d, J=16.9 Hz, 1H), 4.71-4.59 (m, 1H), 4.48-4.37 (m, 1H), 4.31-4.20 (m, 1H), 4.03-3.93 (m, 1H).

Example 33: 2-[6-[4-Chloro-3-(1,1-difluoroethyl)phenyl]pyrazolo[3,4-b]pyrazin-1-yl]-1-(3-methylazetidin-1-yl)ethanone

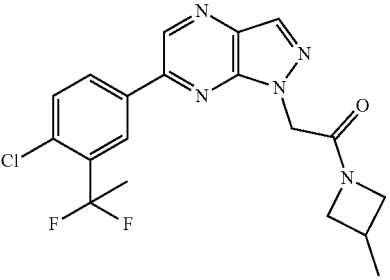 [SMILES: CC1CN(C(=O)Cn2ncc3ncc(-c4ccc(Cl)c(C(C)(F)F)c4)nc32)C1]

The title compound was prepared in a manner analogous to Example 35 using 2-(6-(4-chloro-3-(1,1-difluoroethyl)phenyl)-1H-pyrazolo[4,3-b]pyridin-1-yl)acetic acid (Intermediate 12) instead of 2-(6-(3-(difluoromethoxy)-4-fluorophenyl)-1H-pyrazolo[4,3-b]pyridin-1-yl)acetic acid (Intermediate 13). MS (ESI): mass calcd. for $C_{19}H_{18}ClF_2N_5O$, 405.1; m/z found, 406.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 34: 2-[6-[4-Chloro-3-(1,1-difluoroethyl)phenyl]pyrazolo[3,4-b]pyrazin-1-yl]-1-(3-fluoroazetidin-1-yl)ethanone

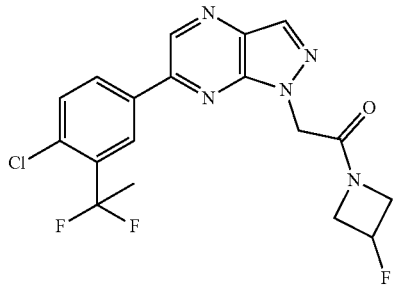 [SMILES: CC(F)(F)c1cc(-c2cnc3cnn(CC(=O)N4CC(F)C4)c3n2)ccc1Cl]

The title compound was prepared in a manner analogous to Example 35 using 2-(6-(4-chloro-3-(1,1-difluoroethyl)phenyl)-1H-pyrazolo[4,3-b]pyridin-1-yl)acetic acid (Intermediate 12) instead of 2-(6-(3-(difluoromethoxy)-4-fluorophenyl)-1H-pyrazolo[4,3-b]pyridin-1-yl)acetic acid (Intermediate 13) and 3-fluoroazetidine HCl instead of 3-methylazetidine HCl. MS (ESI): mass calcd. for $C_{18}H_{15}ClF_3N_5O$, 409.1; m/z found, 410.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 35: 2-[6-[3-(Difluoromethoxy)-4-fluorophenyl]pyrazolo[3,4-b]pyrazin-1-yl]-1-(3-methylazetidin-1-yl)ethanone

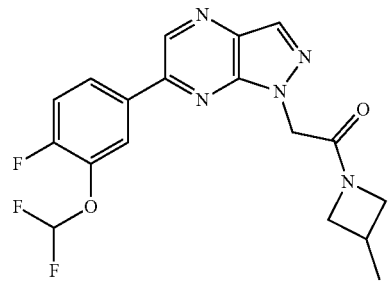 [SMILES: CC1CN(C(=O)Cn2ncc3ncc(-c4ccc(F)c(OC(F)F)c4)nc32)C1]

To a solution of 2-(6-(3-(difluoromethoxy)-4-fluorophenyl)-1H-pyrazolo[4,3-b]pyridin-1-yl)acetic acid (Intermediate 13, 20 mg, 0.057 mmol), 3-methylazetidine HCl (10 mg, 0.089 mmol), EDCI (17 mg, 0.089 mmol), and HOBt (12 mg, 0.089 mmol) in DCM (2 mL) was added DIEA (20 µL, 0.118 mmol). The resulting mixture was stirred at rt overnight. The reaction mixture was diluted with DCM (3 mL) and washed with water and brine. The organic layer was separated, dried with Na$_2$SO$_4$, filtered and concentrated under reduced pressure. Purification (FCC, SiO$_2$, 0-80% EtOAc in Hexanes) afforded the title compound (11.3 mg, 49%). MS (ESI): mass calcd. for $C_{18}H_{16}F_3N_5O_2$, 391.1; m/z found, 392.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 36: 2-[6-[3-(Difluoromethoxy)-4-fluorophenyl]pyrazolo[3,4-b]pyrazin-1-yl]-1-(3-fluoroazetidin-1-yl)ethanone

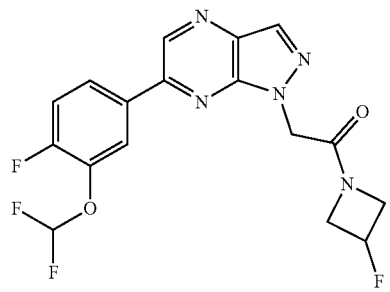 [SMILES: O=C(Cn1ncc2ncc(-c3ccc(F)c(OC(F)F)c3)nc21)N1CC(F)C1]

The title compound was prepared in a manner analogous to Example 35 using 3-fluoroazetidine HCl instead of 3-methylazetidine HCl. MS (ESI): mass calcd. for $C_{17}H_{13}F_4N_5O_2$, 395.1; m/z found, 396.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 37: 2-[6-[4-Chloro-3-(1,1-difluoroethyl)phenyl]pyrazolo[3,4-b]pyrazin-1-yl]-1-morpholinoethanone

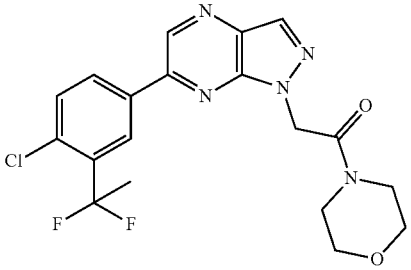 [SMILES: CC(F)(F)c1cc(-c2cnc3cnn(CC(=O)N4CCOCC4)c3n2)ccc1Cl]

The title compound was prepared in a manner analogous to Example 2, using 6-(4-chloro-3-(1,1-difluoroethyl)phenyl)-1H-pyrazolo[3,4-b]pyrazine (Intermediate 10) instead of 6-(3-(difluoromethoxy)-4-chlorophenyl)-1H-pyrazolo[3,4-b]pyrazine (Intermediate 9) and 4-(2-chloroazetyl)morpholine instead of 2-bromo-1-cyclopropylethanone. MS (ESI): mass calcd. for $C_{19}H_{18}ClF_2N_5O_2$, 421.1; m/z found, 422.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 38: 2-[[6-[3-(Difluoromethyl)-4-fluoro-phenyl]pyrazolo[3,4-b]pyrazin-1-yl]methyl]-5-methyl-1,3,4-thiadiazole

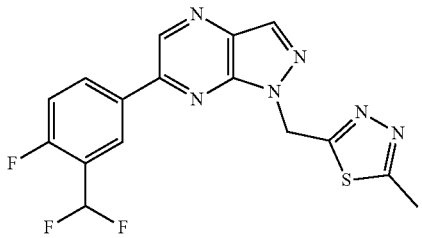 [SMILES: Cc1nnc(Cn2ncc3ncc(-c4ccc(F)c(C(F)F)c4)nc32)o1]

The title compound was prepared in a manner analogous to Example 1 using 2-(chloromethyl)-5-methyl-1,3,4-thiadiazole instead of 1-bromobutan-2-one. MS (ESI): mass calcd. for $C_{16}H_{11}F_3N_6S$, 376.1; m/z found, 377.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 39: 2-[[6-[3-(Difluoromethyl)-4-fluoro-phenyl]pyrazolo[3,4-b]pyrazin-1-yl]methyl]-5-methyl-1,3,4-oxadiazole

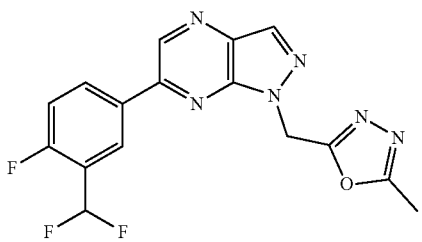

The title compound was prepared in a manner analogous to Example 1, using 2-(chloromethyl)-5-methyl-1,3,4-oxadiazole instead of 1-bromobutan-2-one. MS (ESI): mass calcd. for $C_{16}H_{11}F_3N_6O$, 360.1; m/z found, 361.2 [M+H]$^+$.

Example 40: 5-[[6-[3-(Difluoromethyl)-4-fluoro-phenyl]pyrazolo[3,4-b]pyrazin-1-yl]methyl]-3-methyl-isoxazole

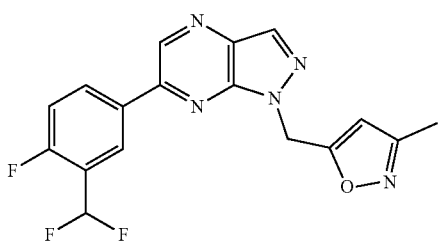 [SMILES: Cc1cc(Cn2ncc3ncc(-c4ccc(F)c(C(F)F)c4)nc32)on1]

The title compound was prepared in a manner analogous to Example 1, using 5-(chloromethyl)-3-methylisoxazole instead of 1-bromobutan-2-one. MS (ESI): mass calcd. for $C_{17}H_{12}F_3N_5O$, 359.1; m/z found, 360.1 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 41: 6-[3-(Difluoromethyl)-4-fluoro-phenyl]-1-[(5-fluoro-3-pyridyl)methyl]pyrazolo[3,4-b]pyrazine

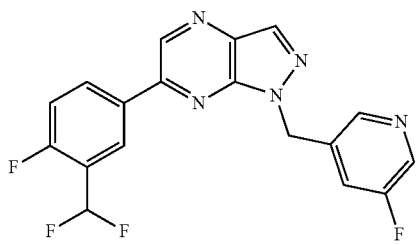 [SMILES: Fc1cncc(Cn2ncc3ncc(-c4ccc(F)c(C(F)F)c4)nc32)c1]

The title compound was prepared in a manner analogous to Example 3, using 6-chloro-1-((5-fluoropyridin-3-yl)methyl)-1H-pyrazolo[3,4-b]pyrazine (Intermediate 4) instead of 2-(6-chloro-1H-pyrazolo[3,4-b]pyrazin-1-yl)-N,N-dimethylacetamide (Intermediate 3) and 2-(3-(difluoromethyl)-4-fluorophenyl)-4,4,5,5-tetramethyl-1,3,2-dioxaborolane instead of (5-(trifluoromethyl)thiophen-2-yl) boronic acid. MS (ESI): mass calcd. for $C_{18}H_{11}F_4N_5$, 373.1; m/z found, 374.1 [M+H]$^+$. $^1$H NMR (300 MHz, DMSO-d$_6$) δ 9.39 (s, 1H), 8.57 (s, 1H), 8.56-8.46 (m, 4H), 7.76-7.67 (m, 1H), 7.69-7.58 (m, 1H), 7.33 (t, J=54.1 Hz, 1H), 5.88 (s, 2H).

Example 42: 1-[(5-Chloro-3-pyridyl)methyl]-6-[3-(difluoromethyl)-4-fluoro-phenyl]pyrazolo[3,4-b]pyrazine

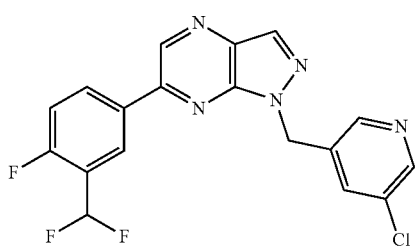 [SMILES: Fc1ccc(-c2cnc3cnn(Cc4cncc(Cl)c4)c3n2)cc1C(F)F]

The title compound was prepared in a manner analogous to Example 1, using 3-chloro-5-(chloromethyl)pyridine HCl instead of 1-bromobutan-2-one. MS (ESI): mass calcd. for $C_{18}H_{11}ClF_3N_5$, 389.1; m/z found, 390.1 [M+H]$^+$. $^1$H NMR (300 MHz, DMSO-d$_6$) δ 9.39 (s, 1H), 8.76-8.38 (m, 5H), 8.00-7.88 (m, 1H), 7.69-7.58 (m, 1H), 7.33 (t, J=54.0 Hz, 1H), 5.86 (s, 2H).

Example 43: 6-[3-(Difluoromethyl)-4-fluoro-phenyl]-1-[(5-methoxy-3-pyridyl)methyl]pyrazolo[3,4-b]pyrazine

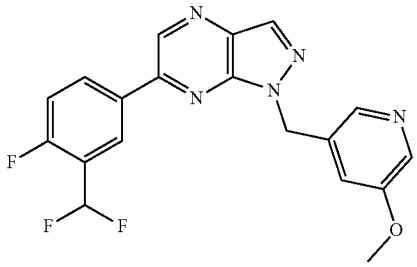 [SMILES: COc1cncc(Cn2ncc3ncc(-c4ccc(F)c(C(F)F)c4)nc32)c1]

The title compound was prepared in a manner analogous to Example 1, using 3-(chloromethyl)-5-methoxypyridine HCl instead of 1-bromobutan-2-one. MS (ESI): mass calcd. for $C_{19}H_{14}F_3N_5O$, 385.1; m/z found, 386.1 [M+H]$^+$. $^1$H NMR (300 MHz, DMSO-d$_6$) δ 9.38 (s, 1H), 8.63-8.49 (m, 2H), 8.55 (s, 1H), 8.26-8.21 (m, 1H), 8.22-8.17 (m, 1H), 7.67-7.57 (m, 1H), 7.42-7.36 (m, 1H), 7.33 (t, J=54.1 Hz, 1H), 5.81 (s, 2H), 3.78 (s, 3H).

Example 44: 5-[[6-[3-(Difluoromethyl)-4-fluoro-phenyl]pyrazolo[3,4-b]pyrazin-1-yl]methyl]pyridine-3-carbonitrile

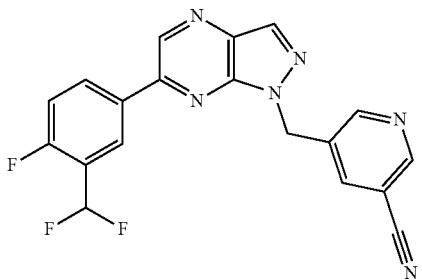 [SMILES: N#Cc1cncc(Cn2ncc3ncc(-c4ccc(F)c(C(F)F)c4)nc32)c1]

The title compound was prepared in a manner analogous to Example 1, using 5-(chloromethyl)nicotinonitrile instead of 1-bromobutan-2-one. MS (ESI): mass calcd. for $C_{19}H_{11}F_3N_6$, 380.1; m/z found, 381.1 [M+H]$^+$. $^1$H NMR (300 MHz, DMSO-d$_6$) δ 9.40 (s, 1H), 8.97 (d, J=2.0 Hz, 1H), 8.92 (d, J=2.2 Hz, 1H), 8.58 (s, 1H), 8.58-8.50 (m, 2H), 8.32-8.22 (m, 1H), 7.69-7.57 (m, 1H), 7.33 (t, J=54.1 Hz, 1H), 5.90 (s, 2H).

Example 45: 5-[[6-[3-(Difluoromethyl)-4-fluoro-phenyl]-3-fluoro-pyrazolo[3,4-b]pyrazin-1-yl]methyl]pyridine-3-carbonitrile

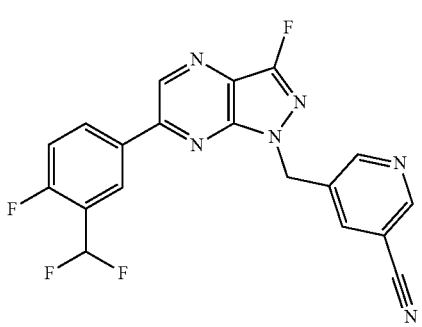 [SMILES: N#Cc1cncc(Cn2nc(F)c3ncc(-c4ccc(F)c(C(F)F)c4)nc32)c1]

The title compound was prepared in a manner analogous to Example 1 using 6-(3-(difluoromethyl)-4-fluorophenyl)-3-fluoro-1H-pyrazolo[3,4-b]pyrazine (Intermediate 7) instead of 6-(3-(difluoromethyl)-4-fluorophenyl)-1H-pyrazolo[3,4-b]pyrazine (Intermediate 2) and 5-(chloromethyl) nicotinonitrile instead of 1-bromobutan-2-one. MS (ESI): mass calcd. for $C_{19}H_{10}F_4N_6$, 398.1; m/z found, 399.1 [M+H]$^+$. $^1$H NMR (300 MHz, DMSO-d$_6$) δ 9.45 (s, 1H), 8.98 (d, J=2.0 Hz, 1H), 8.93 (d, J=2.2 Hz, 1H), 8.65-8.51 (m, 2H), 8.33-8.21 (m, 1H), 7.71-7.59 (m, 1H), 7.33 (t, J=54.0 Hz, 1H), 5.80 (s, 2H).

Example 46: 1-[(5-Chloro-3-pyridyl)methyl]-6-[3-(difluoromethoxy)-4-fluoro-phenyl]pyrazolo[3,4-b]pyrazine

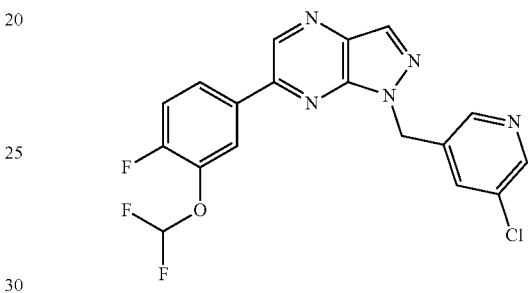

The title compound was prepared in a manner analogous to Example 1, using 6-(3-(difluoromethoxy)-4-fluorophenyl)-1H-pyrazolo[3,4-b]pyrazine (Intermediate 8) instead of 6-(3-(difluoromethyl)-4-fluorophenyl)-1H-pyrazolo[3,4-b] pyrazine (Intermediate 2) and 3-chloro-5-(chloromethyl) pyridine HCl instead of 1-bromobutan-2-one. MS (ESI): mass calcd. for $C_{18}H_{11}ClF_3N_5O$, 405.1; m/z found, 406.0 [M+H]$^+$. $^1$H NMR (500 MHz, CDCl$_3$) δ 9.04 (s, 1H), 8.36 (s, 1H), 7.93-7.90 (m, 1H), 7.90-7.85 (m, 1H), 7.42 (t, J=7.6 Hz, 1H), 7.35-7.28 (m, 1H), 5.43 (s, 2H), 3.19 (s, 3H), 3.01 (s, 3H), 2.48 (s, 3H).

Example 47: 2-(6-(4-Chloro-2-fluorophenyl)-1H-pyrazolo[3,4-b]pyrazin-1-yl)-N,N-dimethylacetamide

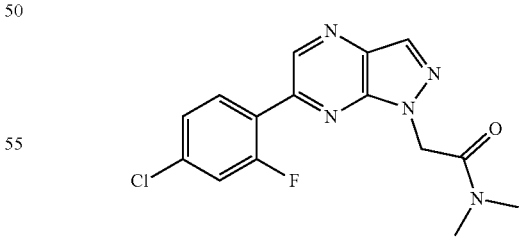

The title compound was prepared in a manner analogous to Example 3, using 4-chloro-2-fluorophenylbronic acid instead of (5-(trifluoromethyl)thiophen-2-yl)boronic acid. MS (ESI): mass calcd. for $C_{15}H_{13}ClFN_5O$, 333.08; m/z found, 334.1 [M+H]$^+$. $^1$H NMR (500 MHz, CDCl$_3$) δ 9.05 (d, J=2.7 Hz, 1H), 8.39 (s, 1H), 8.00 (t, J=8.3 Hz, 1H), 7.37-7.27 (m, 2H), 5.42 (s, 2H), 3.20 (s, 3H), 3.01 (s, 3H).

Example 48: N,N-Dimethyl-2-(6-(4-(trifluoromethoxy)phenyl)-1H-pyrazolo[3,4-b]pyrazin-1-yl)acetamide

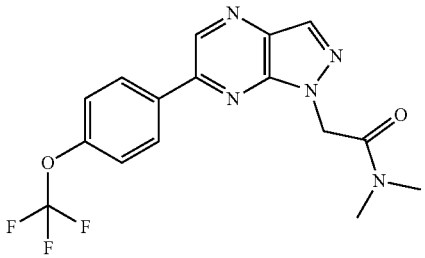 [SMILES: CN(C)C(=O)Cn1ncc2ncc(-c3ccc(OC(F)(F)F)cc3)nc21]

The title compound was prepared in a manner analogous to Example 3, using 4-(trifluoromethoxy)phenylbronic acid instead of (5-(trifluoromethyl)thiophen-2-yl)boronic acid. MS (ESI): mass calcd. for $C_{16}H_{14}F_3N_5O_2$, 365.11; m/z found, 366.1 [M+H]$^+$. $^1$H NMR (500 MHz, CDCl$_3$) δ 9.03 (s, 1H), 8.38 (s, 1H), 8.22-8.08 (m, 2H), 7.47-7.32 (m, 2H), 5.43 (s, 2H), 3.20 (s, 3H), 3.01 (s, 3H).

Example 49: 2-(6-(2,5-Difluorophenyl)-1H-pyrazolo[3,4-b]pyrazin-1-yl)-N,N-dimethylacetamide

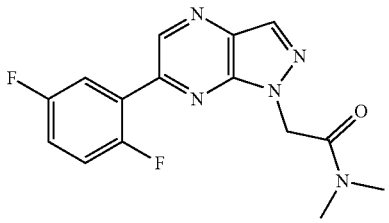 [SMILES: CN(C)C(=O)Cn1ncc2ncc(-c3cc(F)ccc3F)nc21]

The title compound was prepared in a manner analogous to Example 3, using 2,5-difluorophenylbronic acid instead of (5-(trifluoromethyl)thiophen-2-yl)boronic acid. MS (ESI): mass calcd. for $C_{15}H_{13}F_2N_5O$, 317.11; m/z found, 318.1 [M+H]$^+$. $^1$H NMR (500 MHz, CDCl$_3$) δ 9.11 (d, J=3.1 Hz, 1H), 8.40 (s, 1H), 7.90-7.71 (m, 1H), 7.25-7.07 (m, 2H), 5.43 (s, 2H), 3.21 (s, 3H), 3.01 (s, 3H).

Example 50: (R,S)-5-((6-(3-(Difluoromethoxy)-4-fluorophenyl)-1H-pyrazolo[3,4-b]pyrazin-1-yl)methyl)oxazolidin-2-one Hydrochloride

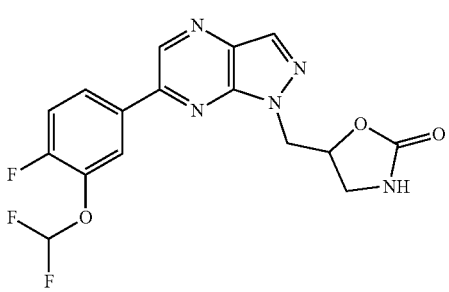 [SMILES: O=C1NCC(Cn2ncc3ncc(-c4ccc(F)c(OC(F)F)c4)nc32)O1]

Step A: tert-Butyl 5-((6-(3-(difluoromethoxy)-4-fluorophenyl)-1H-pyrazolo[3,4-b]pyrazin-1-yl)methyl)-2-oxooxazolidine-3-carboxylate The title compound was prepared in a manner analogous to Example 1 using 6-(3-(difluoromethoxy)-4-fluorophenyl)-1H-pyrazolo[3,4-b]pyrazine (Intermediate 8) instead of 6-(3-(difluoromethyl)-4-fluorophenyl)-1H-pyrazolo[3,4-b]pyrazine (Intermediate 2), and using tert-butyl 5-(chloromethyl)-2-oxooxazolidine-3-carboxylate. MS (ESI): mass calcd. for $C_{21}H_{20}F_3N_5O_5$, 479.14; m/z found, 380.1 [M+H-tertbutyl]$^+$. $^1$H NMR (500 MHz, CDCl$_3$) δ 9.04 (s, 1H), 8.34 (s, 1H), 8.10-8.02 (m, 1H), 8.02-7.91 (m, 1H), 7.42-7.30 (m, 1H), 6.73 (t, J=73.1 Hz, 1H), 5.15-5.03 (m, 1H), 5.02-4.88 (m, 1H), 4.87-4.71 (m, 1H), 4.14-4.06 (m, 1H), 4.06-3.97 (m, 1H), 1.51 (s, 9H).

Step B: (R,S)-5-((6-(3-(Difluoromethoxy)-4-fluorophenyl)-1H-pyrazolo[3,4-b]pyrazin-1-yl)methyl)oxazolidin-2-one Hydrochloride. A solution of tert-butyl 5-((6-(3-(difluoromethoxy)-4-fluorophenyl)-1H-pyrazolo[3,4-b]pyrazin-1-yl)methyl)-2-oxooxazolidine-3-carboxylate (6.5 mg, 0.014 mmol) in DCM (1 mL) was charged with 4M HCl in Dioxane (50 uL, 0.2 mmol). The resulting solution was stirred at r.t. overnight. The completed reaction was concentrated to give the title compound (4.6 mg, 82%). MS (ESI): mass calcd. for $C_{16}H_{12}F_3N_5O_3$, 379.09; m/z found, 380.0 [M+H]$^+$.

Example 51: 6-(3-(Difluoromethoxy)-4-fluorophenyl)-1-((5-methoxypyridin-3-yl)methyl)-1H-pyrazolo[3,4-b]pyrazine

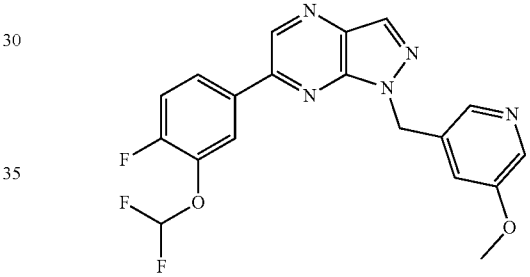

The title compound was prepared in a manner analogous to Example 1 using 6-(3-(difluoromethoxy)-4-fluorophenyl)-1H-pyrazolo[3,4-b]pyrazine (Intermediate 8) instead of 6-(3-(difluoromethyl)-4-fluorophenyl)-1H-pyrazolo[3,4-b]pyrazine (Intermediate 2), and using 3-methoxy-5-methylpyridine instead of 1-bromobutan-2-one. MS (ESI): mass calcd. for $C_{19}H_{14}F_3N_5O_2$, 401.11; m/z found, 402.1 [M+H]$^+$. $^1$H NMR (500 MHz, CDCl$_3$) δ 9.04 (s, 1H), 8.32 (t, J=2.6 Hz, 2H), 8.28 (s, 1H), 8.20-8.11 (m, 1H), 8.07-7.98 (m, 1H), 7.39-7.29 (m, 1H), 7.26-7.24 (m, 1H), 6.66 (t, J=73.1 Hz, 1H), 5.66 (s, 2H), 3.84 (s, 3H).

Example 52: 2-(6-(4-(1,1-Difluoroethyl)phenyl)-1H-pyrazolo[3,4-b]pyrazin-1-yl)-N,N-dimethylacetamide

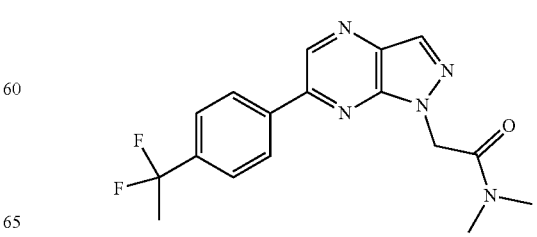

The title compound was prepared in a manner analogous to Example 3, using 1,3,2-dioxaborolane, 2-[4-(1,1-difluoroethyl)phenyl]-4,4,5,5-tetramethyl- instead of (5-(trifluoromethyl)thiophen-2-yl)boronic acid. MS (ESI): mass calcd. for $C_{17}H_{17}F_2N_5O$, 345.14; m/z found, 346.1 [M+H]$^+$. $^1$H NMR (500 MHz, CDCl$_3$) δ 9.06 (s, 1H), 8.39 (s, 1H), 8.21-8.07 (m, 2H), 7.75-7.61 (m, 2H), 5.44 (s, 2H), 3.21 (s, 3H), 3.01 (s, 3H), 1.98 (t, J=18.2 Hz, 3H).

Biological Assays

Effects of Test Articles on Cloned Human NR1/NR2B Ion Channels Expressed in Mammalian Cells NMDA receptors are ion channels that are highly permeable to $Ca^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular $Ca^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 137 mM NaCl, 4 mM KCl, 2 mM CaCl$_2$), 0.5 mM MgCl$_2$ (standard assay) or 1.5 mM MgCl$_2$ (HTS assay), 10 mM HEPES and 5 mM D-glucose; pH 7.4. After 1 h incubation at the room temperature, the dye is washed away with the assay buffer (137 mM NaCl (standard assay) or 150 mM (HTS assay), 4 mM KCl (standard assay) or 3 mM (HTS assay), 2 mM CaCl$_2$), 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to ~EC$_{40}$ (standard assay) or EC$_{40}$ (HTS assay) is used to maximize the assay's signal window and ability to detect NMDA receptor antagonists and negative allosteric modulators. A saturating concentration (10 μM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

TABLE 3

| Ex # | Compound name | NR2B IC$_{50}$ Standard assay (μM) |
|---|---|---|
| 1 | 1-[6-[3-(Difluoromethyl)-4-fluoro-phenyl]pyrazolo[3,4-b]pyrazin-1-yl]butan-2-one; | 0.022 |
| 2 | 2-[6-[4-Chloro-3-(difluoromethoxy)phenyl]pyrazolo[3,4-b]pyrazin-1-yl]-1-cyclopropyl-ethanone; | 0.081 |
| 3 | N,N-Dimethyl-2-[6-[5-(trifluoromethyl)-2-thienyl]pyrazolo[3,4-b]pyrazin-1-yl]acetamide; | 0.581 |
| 4 | N,N-Dimethyl-2-[6-(m-tolyl)pyrazolo[3,4-b]pyrazin-1-yl]acetamide; | 0.410 |
| 5 | 2-[6-(4-Chloro-3-fluoro-phenyl)pyrazolo[3,4-b]pyrazin-1-yl]-N,N-dimethyl-acetamide; | 0.827 |
| 6 | 2-[6-(3-Fluoro-4-methyl-phenyl)pyrazolo[3,4-b]pyrazin-1-yl]-N,N-dimethyl-acetamide; | 0.916 |
| 7 | 2-[6-(4-Fluoro-3-methyl-phenyl)pyrazolo[3,4-b]pyrazin-1-yl]-N,N-dimethyl-acetamide; | 0.117 |
| 8 | 2-[6-(4-Chloro-3-methyl-phenyl)pyrazolo[3,4-b]pyrazin-1-yl]-N,N-dimethyl-acetamide; | 0.134 |
| 9 | 2-[6-(3-Chloro-4-methoxy-phenyl)pyrazolo[3,4-b]pyrazin-1-yl]-N,N-dimethyl-acetamide; | 0.584 |
| 10 | 2-[6-[3-(Difluoromethyl)-4-fluoro-phenyl]pyrazolo[3,4-b]pyrazin-1-yl]-N,N-dimethyl-acetamide; | 0.042 |
| 11 | 2-[6-[3-(Difluoromethyl)-4-fluoro-phenyl]-3-fluoro-pyrazolo[3,4-b]pyrazin-1-yl]-N,N-dimethyl-acetamide; | 0.059 |
| 12 | 2-[6-[4-Chloro-3-(difluoromethyl)phenyl]pyrazolo[3,4-b]pyrazin-1-yl]-N,N-dimethyl-acetamide; | 0.036 |
| 13 | 2-[6-[3-(1,1-Difluoroethyl)-4-fluoro-phenyl]pyrazolo[3,4-b]pyrazin-1-yl]-N,N-dimethyl-acetamide; | 0.146 |
| 14 | 2-[6-[4-Chloro-3-(1,1-difluoroethyl)phenyl]pyrazolo[3,4-b]pyrazin-1-yl]-N,N-dimethyl-acetamide; | 0.149 |
| 15 | 2-[6-[4-Chloro-3-(trifluoromethyl)phenyl]pyrazolo[3,4-b]pyrazin-1-yl]-N,N-dimethyl-acetamide; | 0.272 |
| 16 | 2-[6-[3-(Difluoromethoxy)-4-fluoro-phenyl]pyrazolo[3,4-b]pyrazin-1-yl]-N,N-dimethyl-acetamide; | 0.072 |
| 17 | 2-[6-[4-(Difluoromethoxy)-3-fluoro-phenyl]pyrazolo[3,4-b]pyrazin-1-yl]-N,N-dimethyl-acetamide; | 0.859 |
| 18 | 2-[6-[4-Chloro-3-(difluoromethoxy)phenyl]pyrazolo[3,4-b]pyrazin-1-yl]-N,N-dimethyl-acetamide; | 0.064 |
| 19 | 2-[6-[3-Chloro-4-(trifluoromethoxy)phenyl]pyrazolo[3,4-b]pyrazin-1-yl]-N,N-dimethyl-acetamide; | 1.040 |
| 20 | 2-[6-(3,5-Difluoro-4-methyl-phenyl)pyrazolo[3,4-b]pyrazin-1-yl]-N,N-dimethyl-acetamide; | 0.907 |
| 21 | 2-[6-(2,4-Difluoro-3-methyl-phenyl)pyrazolo[3,4-b]pyrazin-1-yl]-N,N-dimethyl-acetamide; | 0.034 |
| 22 | N,N-Dimethyl-2-[6-(3,4,5-trifluorophenyl)pyrazolo[3,4-b]pyrazin-1-yl]acetamide; | 0.489 |

TABLE 3-continued

| Ex # | Compound name | NR2B IC$_{50}$ Standard assay (μM) |
|---|---|---|
| 23 | N,N-Dimethyl-2-[6-(2,3,4-trifluorophenyl)pyrazolo[3,4-b]pyrazin-1-yl]acetamide; | 0.962 |
| 24 | 1-(Azetidin-1-yl)-2-[6-[3-(difluoromethyl)-4-fluoro-phenyl]pyrazolo[3,4-b]pyrazin-1-yl]ethanone; | 0.037 |
| 25 | 1-(Azetidin-1-yl)-2-[6-[3-(difluoromethyl)-4-fluoro-phenyl]-3-fluoro-py razolo[3,4-b]pyrazin-1-yl] ethanone; | 0.065 |
| 26 | 1-(Azetidin-1-yl)-2-[6-[4-chloro-3-(1,1-difluoroethyl)phenyl]pyrazolo[3,4-b]pyrazin-1-yl]ethanone; | 0.140 |
| 27 | 1-(Azetidin-1-yl)-2-[6-[3-(1,1-difluoroethyl)-4-fluoro-phenyl]pyrazolo [3,4-b]pyrazin-1-yl]ethanone; | 0.126 |
| 28 | 1-(Azetidin-1-yl)-2-[6-[3-(difluoromethoxy)-4-fluoro-phenyl]pyrazolo [3,4-b] pyrazin-1-yl]ethanone; | 0.059 |
| 29 | 1-(Azetidin-1-yl)-2-[6-[4-chloro-3-(difluoromethoxy)phenyl]pyrazolo[3,4-b]pyrazin-1-yl]ethanone; | 0.069 |
| 30 | 2-[6-[3-(Difluoromethyl)-4-fluoro-phenyl]pyrazolo[3,4-b]pyrazin-1-yl]-1-(3-methylazetidin-1-yl)ethanone; | 0.122 |
| 31 | 2-[6-[3-(Difluoromethyl)-4-fluoro-phenyl]-3-fluoro-pyrazolo[3,4-b]pyrazin-1-yl]-1-(3-methylazetidin-1-yl)ethanone; | 0.196 |
| 32 | 2-[6-[3-(Difluoromethyl)-4-fluoro-phenyl]pyrazolo[3,4-b]pyrazin-1-yl]-1-(3-fluoroazetidin-1-yl)ethanone; | 0.037 |
| 33 | 2-[6-[3-(Difluoromethyl)-4-fluoro-phenyl]-3-fluoro-pyrazolo[3,4-b]pyrazin-1-yl]-1-(3-fluoroazetidin-1-yl)ethanone; | 0.077 |
| 34 | 2-[6-[4-Chloro-3-(1,1-difluoroethyl)phenyl]pyrazolo[3,4-b]pyrazin-1-yl]-1-(3-methylazetidin-1-yl)ethanone; | 0.408 |
| 35 | 2-[6-[4-Chloro-3-(1,1-difluoroethyl)phenyl]pyrazolo[3,4-b]pyrazin-1-yl]-1-(3-fluoroazetidin-1-yl)ethanone; | 0.212 |
| 36 | 2-[6-[3-(Difluoromethoxy)-4-fluoro-phenyl]pyrazolo[3,4-b]pyrazin-1-yl]-1-(3-methylazetidin-1-yl)ethanone; | 0.251 |
| 37 | 2-[6-[3-(Difluoromethoxy)-4-fluoro-phenyl]pyrazolo[3,4-b]pyrazin-1-yl]-1-(3-fluoroazetidin-1-yl)ethanone; | 0.092 |
| 38 | 2-[6-[4-Chloro-3-(1,1-difluoroethyl)phenyl]pyrazolo[3,4-b]pyrazin-1-yl]-1-morpholino-ethanone; | 1.060 |
| 39 | 2-[[6-[3-(Difluoromethyl)-4-fluoro-phenyl]pyrazolo[3,4-b]pyrazin-1-yl]methyl]-5-methyl-1,3,4-thiadiazole; | 0.162 |
| 40 | 2-[[6-[3-(Difluoromethyl)-4-fluoro-phenyl]pyrazolo[3,4-b]pyrazin-1-yl]methyl]-5-methyl-1,3,4-oxadiazole; | 0.158 |
| 41 | 5-[[6-[3-(Difluoromethyl)-4-fluoro-phenyl]pyrazolo[3,4-b]pyrazin-1-yl]methyl]-3-methyl-isoxazole; | 0.337 |
| 42 | 6-[3-(Difluoromethyl)-4-fluoro-phenyl]-1-[(5-fluoro-3-pyridyl)methyl]pyrazolo[3,4-b]pyrazine; | 0.079 |
| 43 | 1-[(5-Chloro-3-pyridyl)methyl]-6-[3-(difluoromethyl)-4-fluoro-phenyl]pyrazolo[3,4-b]pyrazine; | 0.250 |
| 44 | 6-[3-(Difluoromethyl)-4-fluoro-phenyl]-1-[(5-methoxy-3-pyridyl)methyl]pyrazolo[3,4-b]pyrazine; | 0.165 |
| 45 | 5-[[6-[3-(Difluoromethyl)-4-fluoro-phenyl]pyrazolo[3,4-b]pyrazin-1-yl]methyl]pyridine-3-carbonitrile; | 0.285 |
| 46 | 5-[[6-[3-(Difluoromethyl)-4-fluoro-phenyl]-3-fluoro-pyrazolo[3,4-b]pyrazin-1-yl]methyl]pyridine-3-carbonitrile; | 0.709 |
| 47 | 1-[(5-Chloro-3-pyridyl)methyl]-6-[3-(difluoromethoxy)-4-fluoro-phenyl]pyrazolo[3,4-b]pyrazine; | 0.284 |
| 48 | 2-(6-(4-Chloro-2-fluorophenyl)-1H-pyrazolo[3,4-b]pyrazin-1-yl)-N,N-dimethylacetamide; | 2.81 |
| 49 | N,N-Dimethyl-2-(6-(4-(trifluoromethoxy)phenyl)-1H-pyrazolo[3,4-b]pyrazin-1-yl)acetamide; | 2.74 |
| 50 | 2-(6-(2,5-Difluorophenyl)-1H-pyrazolo[3,4-b]pyrazin-1-yl)-N,N-dimethylacetamide; | >3 |
| 51 | 5-((6-(3-(Difluoromethoxy)-4-fluorophenyl)-1H-pyrazolo[3,4-b]pyrazin-1-yl)methyl)oxazolidin-2-one Hydrochloride salt; | >3 |
| 52 | 6-(3-(Difluoromethoxy)-4-fluorophenyl)-1-((5-methoxypyridin-3-yl)methyl)-1H-pyrazolo[3,4-b]pyrazine; and | 3.77 |
| 53 | 2-(6-(4-(1,1-Difluoroethyl)phenyl)-1H-pyrazolo[3,4-b]pyrazin-1-yl)-N,N-dimethylacetamide. | >3 |

Protocol for Liver Microsomal Stability (Extraction Ratio)

Liver Microsomal Stability. Microsomal stability studies (Chrovian et al, "1H-Pyrrolo[3,2-b]pyridine GluN2B-Selective Negative Allosteric Modulators". ACS Med Chem Lett. 2019 Jan. 10; 10(3):261-266) were conducted on a Biomek® FX Robotic Liquid Handling Workstation (Beckman Coulter, Brea, CA), which consists of a 96-channel pipette head, a 12-position workstation deck, and a plate incubator. Test compounds (1 μM) were spiked in a reaction mix consisting of 100 mM potassium phosphate buffer (pH 7.4), 3 mM MgCl$_2$, and 0.5 mg/mL liver microsomes from mouse, rat, and human (BD Gentest). The reaction was brought to 37° C. and initiated by adding NADPH to a final concentration of 1 mM. After mixing on the plate deck, 50

µL aliquots were excised from the reaction plate at 0, 5, 10, 20, 40, and 60 min and quenched with four volumes of acetonitrile spiked with 500 µg/nL of the internal standard phenytoin. Quenched plates were centrifuged at 5700 rpm for 10 min at 4° C., and supernatant was diluted 1:3 in water before LC/MS/MS analysis. The compound half-lives were derived from plots of the ln of percent remaining compound over time to determine the intrinsic clearance. The predicted hepatic clearance was derived from the intrinsic clearance value using equations from the well-stirred model (Current Drug Metabolism, 2008, 9, 940-951), where no correction was made plasma protein binding and the blood to plasma concentration ratio was assumed to be one. The extraction ratio (ER) was calculated by dividing the predicted hepatic clearance by species blood flow (Q), where Q is 90, 55, and 21.7 mL/min/kg for mouse, rat and human, respectively Results of the assay performed on the compounds of Examples are shown in Table 4.

TABLE 4

| Example # | Extraction Ratio @ 1 µM |
|---|---|
| 10 | 0.41 |
| 12 | 0.54 |
| 24 | <0.298 |
| 25 | 0.41 |
| 28 | 0.45 |
| 32 | <0.298 |
| 37 | 0.46 |

Specific Embodiments

The present disclosure is exemplified by specific embodiments 1 to 27 below.

1. A compound, having the structure of Formula (I):

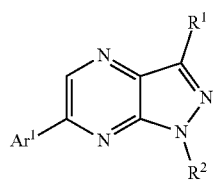

(I)

wherein
R$^1$ is H or halo;
Ar$^1$ is selected from the group consisting of:
(a) phenyl substituted with one, two or three members each independently selected from the group consisting of: halo, C$_{1-6}$alkyl, C$_{1-6}$perhaloalkyl, OC$_{1-6}$alkyl, and OC$_{1-6}$perhaloalkyl; and
(b) thienyl substituted with CF$_3$; and
R$^2$ is selected from the group consisting of:
(c)

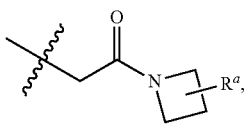

Wherein R$^a$ is selected from the group consisting of: H, halo, and C$_{1-6}$alkyl;

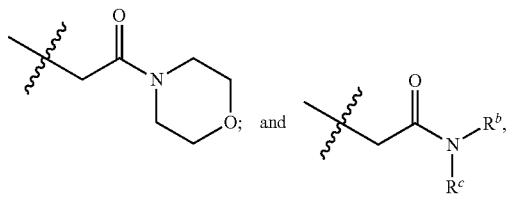

wherein R$^b$ is C$_{1-6}$alkyl, and R$^c$ is C$_{1-6}$alkyl;
(d)

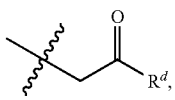

wherein R$^d$ is C$_{1-6}$alkyl, or C$_{3-6}$cycloalkyl; and
(e)

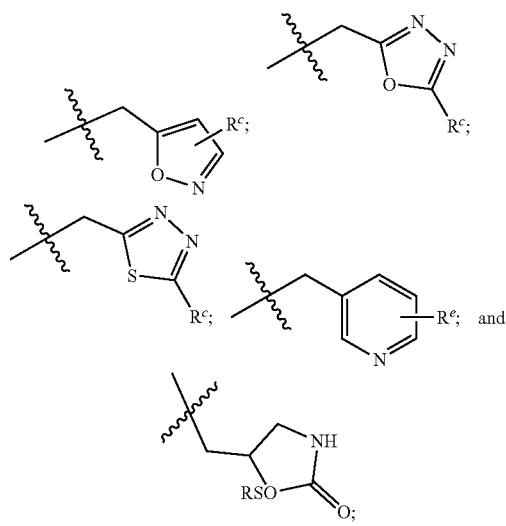

wherein R$^e$ is selected from the group consisting of: halo, OC$_{1-6}$alkyl, and CN; and pharmaceutically acceptable salts, solvates, stereoisomers, isotopic variants, or N-oxides thereof.

2. The compound of embodiment 1, wherein R$^1$ is H.
3. The compound of embodiment 1, wherein R$^1$ is F.
4. The compound of embodiment 1, wherein Ar$^1$ is phenyl substituted with one CH$_3$, OCF$_3$, or CF$_2$CH$_3$ member.
5. The compound of embodiment 1, wherein Ar$^1$ is phenyl substituted with two members each independently selected from the group consisting of: Cl, F, CH$_3$, CHF$_2$, CF$_3$, CHF$_2$CH$_3$, OCH$_3$, and OCHF$_2$.
6. The compound of embodiment 1, wherein Ar$^1$ is

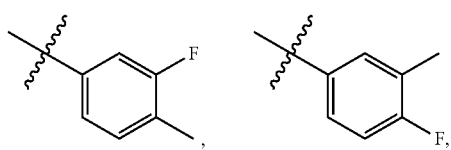

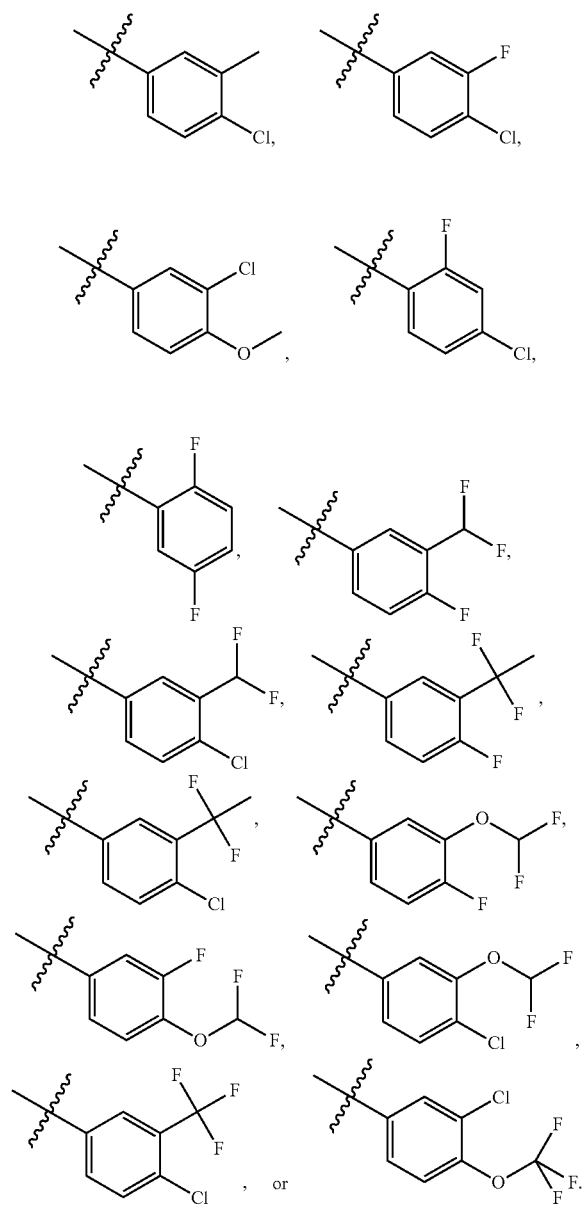

7. The compound of embodiment 1, wherein Ar¹ is phenyl substituted with three members each independently selected from the group consisting of: halo, and CH₃.

8. The compound of embodiment 1, wherein Ar¹ is

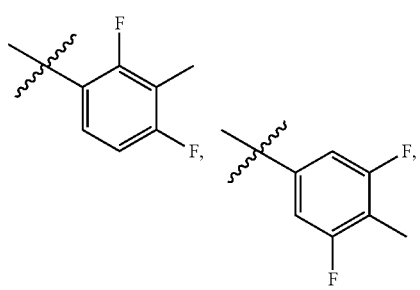

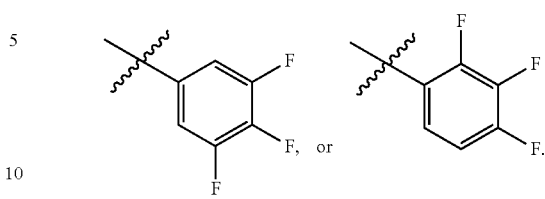

9. The compound of embodiment 1, wherein Ar¹ is

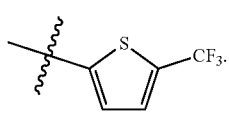 [SMILES: *c1ccc(C(F)(F)F)s1]

10. The compound of embodiment 1, wherein R² is

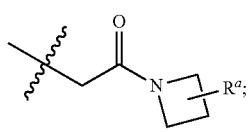

wherein $R^a$ is selected from the group consisting of: H, F, and CH₃.

11. The compound of embodiment 1, wherein R² is

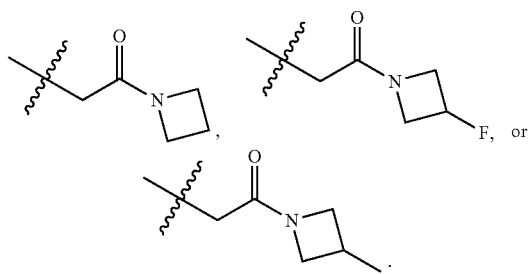

12. The compound of embodiment 1, wherein R² is

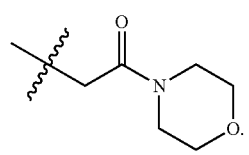 [SMILES: *CC(=O)N1CCOCC1]

13. The compound of embodiment 1, wherein R² is

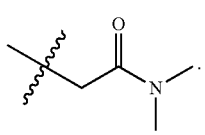 [SMILES: *CC(=O)N(C)C]

14. The compound of embodiment 1, wherein $R^2$ is

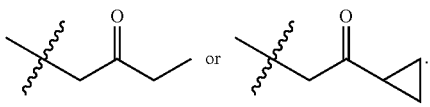

15. The compound of embodiment 1, wherein $R^2$ is

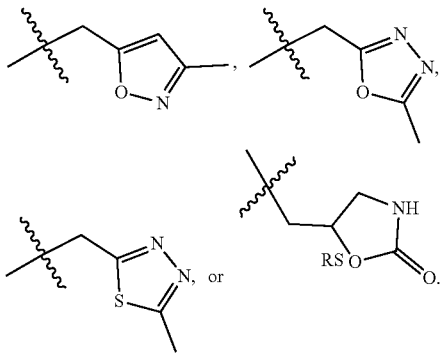

16. The compound of embodiment 1, wherein $R^2$ is

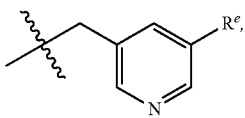

wherein $R^e$ is Cl, F, $OCH_3$, or CN.

17. The compound of embodiment 1, having the structure of Formula (IA):

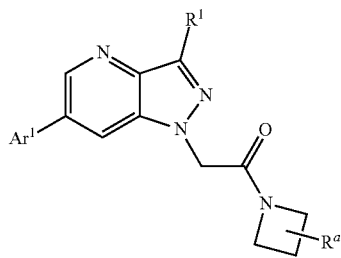

wherein $R^1$ is H, or F;

$Ar^1$ is phenyl substituted with two members each independently selected from the group consisting of: halo, $C_{1-6}$alkyl, $C_{1-6}$perhaloalkyl, and $OC_{1-6}$perhaloalkyl; and $R^a$ is H, halo, or $C_{1-6}$alkyl;

and pharmaceutically acceptable salts, solvates, stereoisomers, isotopic variants, or N-oxides thereof.

18. The compound of embodiment 17, wherein $R^1$ is H.

19. The compound of embodiment 1, having the structure of Formula (IB):

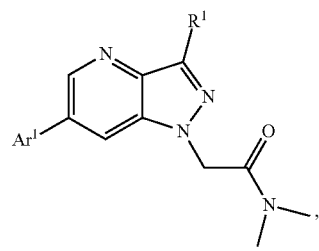

wherein $R^1$ is H, or F; and $Ar^1$ is (a) phenyl substituted with two members each independently selected from the group consisting of: halo, $C_{1-6}$alkyl, $C_{1-6}$perhaloalkyl, and $OC_{1-6}$perhaloalkyl; or (b) thienyl substituted with $CF_3$; and and pharmaceutically acceptable salts, solvates, stereoisomers, isotopic variants, or N-oxides thereof.

20. The compound of embodiment 19, wherein $R^1$ is H.

21. A compound selected from the group consisting of:

1-[6-[3-(Difluoromethyl)-4-fluoro-phenyl]pyrazolo[3,4-b]pyrazin-1-yl]butan-2-one;

2-[6-[4-Chloro-3-(difluoromethoxy)phenyl]pyrazolo[3,4-b]pyrazin-1-yl]-1-cyclopropyl-ethanone;

N,N-Dimethyl-2-[6-[5-(trifluoromethyl)-2-thienyl]pyrazolo[3,4-b]pyrazin-1-yl]acetamide;

N,N-Dimethyl-2-[6-(m-tolyl)pyrazolo[3,4-b]pyrazin-1-yl]acetamide;

2-[6-(4-Chloro-3-fluoro-phenyl)pyrazolo[3,4-b]pyrazin-1-yl]-N,N-dimethyl-acetamide;

2-[6-(3-Fluoro-4-methyl-phenyl)pyrazolo[3,4-b]pyrazin-1-yl]-N,N-dimethyl-acetamide;

2-[6-(4-Fluoro-3-methyl-phenyl)pyrazolo[3,4-b]pyrazin-1-yl]-N,N-dimethyl-acetamide;

2-[6-(4-Chloro-3-methyl-phenyl)pyrazolo[3,4-b]pyrazin-1-yl]-N,N-dimethyl-acetamide;

2-[6-(3-Chloro-4-methoxy-phenyl)pyrazolo[3,4-b]pyrazin-1-yl]-N,N-dimethyl-acetamide;

2-[6-[3-(Difluoromethyl)-4-fluoro-phenyl]pyrazolo[3,4-b]pyrazin-1-yl]-N,N-dimethyl-acetamide;

2-[6-[3-(Difluoromethyl)-4-fluoro-phenyl]-3-fluoro-pyrazolo[3,4-b]pyrazin-1-yl]-N,N-dimethyl-acetamide;

2-[6-[4-Chloro-3-(difluoromethyl)phenyl]pyrazolo[3,4-b]pyrazin-1-yl]-N,N-dimethyl-acetamide;

2-[6-[3-(1,1-Difluoroethyl)-4-fluoro-phenyl]pyrazolo[3,4-b]pyrazin-1-yl]-N,N-dimethyl-acetamide;

2-[6-[4-Chloro-3-(1,1-difluoroethyl)phenyl]pyrazolo[3,4-b]pyrazin-1-yl]-N,N-dimethyl-acetamide;

2-[6-[4-Chloro-3-(trifluoromethyl)phenyl]pyrazolo[3,4-b]pyrazin-1-yl]-N,N-dimethyl-acetamide;

2-[6-[3-(Difluoromethoxy)-4-fluoro-phenyl]pyrazolo[3,4-b]pyrazin-1-yl]-N,N-dimethyl-acetamide;

2-[6-[4-(Difluoromethoxy)-3-fluoro-phenyl]pyrazolo[3,4-b]pyrazin-1-yl]-N,N-dimethyl-acetamide;

2-[6-[4-Chloro-3-(difluoromethoxy)phenyl]pyrazolo[3,4-b]pyrazin-1-yl]-N,N-dimethyl-acetamide;

2-[6-[3-Chloro-4-(trifluoromethoxy)phenyl]pyrazolo[3,4-b]pyrazin-1-yl]-N,N-dimethyl-acetamide;

2-[6-(3,5-Difluoro-4-methyl-phenyl)pyrazolo[3,4-b]pyrazin-1-yl]-N,N-dimethyl-acetamide;

2-[6-(2,4-Difluoro-3-methyl-phenyl)pyrazolo[3,4-b]pyrazin-1-yl]-N,N-dimethyl-acetamide;
N,N-Dimethyl-2-[6-(3,4,5-trifluorophenyl)pyrazolo[3,4-b]pyrazin-1-yl]acetamide;
N,N-Dimethyl-2-[6-(2,3,4-trifluorophenyl)pyrazolo[3,4-b]pyrazin-1-yl]acetamide;
1-(Azetidin-1-yl)-2-[6-[3-(difluoromethyl)-4-fluoro-phenyl]pyrazolo[3,4-b]pyrazin-1-yl]ethanone;
1-(Azetidin-1-yl)-2-[6-[3-(difluoromethyl)-4-fluoro-phenyl]-3-fluoro-pyrazolo[3,4-b]pyrazin-1-yl]ethanone;
1-(Azetidin-1-yl)-2-[6-[4-chloro-3-(1,1-difluoroethyl)phenyl]pyrazolo[3,4-b]pyrazin-1-yl]ethanone;
1-(Azetidin-1-yl)-2-[6-[3-(1,1-difluoroethyl)-4-fluoro-phenyl]pyrazolo[3,4-b]pyrazin-1-yl]ethanone;
1-(Azetidin-1-yl)-2-[6-[3-(difluoromethoxy)-4-fluoro-phenyl]pyrazolo[3,4-b]pyrazin-1-yl]ethanone;
1-(Azetidin-1-yl)-2-[6-[4-chloro-3-(difluoromethoxy)phenyl]pyrazolo[3,4-b]pyrazin-1-yl]ethanone;
2-[6-[3-(Difluoromethyl)-4-fluoro-phenyl]pyrazolo[3,4-b]pyrazin-1-yl]-1-(3-methylazetidin-1-yl)ethanone;
2-[6-[3-(Difluoromethyl)-4-fluoro-phenyl]-3-fluoro-pyrazolo[3,4-b]pyrazin-1-yl]-1-(3-methylazetidin-1-yl)ethanone;
2-[6-[3-(Difluoromethyl)-4-fluoro-phenyl]pyrazolo[3,4-b]pyrazin-1-yl]-1-(3-fluoroazetidin-1-yl)ethanone;
2-[6-[3-(Difluoromethyl)-4-fluoro-phenyl]-3-fluoro-pyrazolo[3,4-b]pyrazin-1-yl]-1-(3-fluoroazetidin-1-yl)ethanone;
2-[6-[4-Chloro-3-(1,1-difluoroethyl)phenyl]pyrazolo[3,4-b]pyrazin-1-yl]-1-(3-methylazetidin-1-yl)ethanone;
2-[6-[4-Chloro-3-(1,1-difluoroethyl)phenyl]pyrazolo[3,4-b]pyrazin-1-yl]-1-(3-fluoroazetidin-1-yl)ethanone;
2-[6-[3-(Difluoromethoxy)-4-fluoro-phenyl]pyrazolo[3,4-b]pyrazin-1-yl]-1-(3-methylazetidin-1-yl)ethanone;
2-[6-[3-(Difluoromethoxy)-4-fluoro-phenyl]pyrazolo[3,4-b]pyrazin-1-yl]-1-(3-fluoroazetidin-1-yl)ethanone;
2-[6-[4-Chloro-3-(1,1-difluoroethyl)phenyl]pyrazolo[3,4-b]pyrazin-1-yl]-1-morpholino-ethanone;
2-[[6-[3-(Difluoromethyl)-4-fluoro-phenyl]pyrazolo[3,4-b]pyrazin-1-yl]methyl]-5-methyl-1,3,4-thiadiazole;
2-[[6-[3-(Difluoromethyl)-4-fluoro-phenyl]pyrazolo[3,4-b]pyrazin-1-yl]methyl]-5-methyl-1,3,4-oxadiazole;
5-[[6-[3-(Difluoromethyl)-4-fluoro-phenyl]pyrazolo[3,4-b]pyrazin-1-yl]methyl]-3-methyl-isoxazole;
6-[3-(Difluoromethyl)-4-fluoro-phenyl]-1-[(5-fluoro-3-pyridyl)methyl]pyrazolo[3,4-b]pyrazine;
1-[(5-Chloro-3-pyridyl)methyl]-6-[3-(difluoromethyl)-4-fluoro-phenyl]pyrazolo[3,4-b]pyrazine;
6-[3-(Difluoromethyl)-4-fluoro-phenyl]-1-[(5-methoxy-3-pyridyl)methyl]pyrazolo[3,4-b]pyrazine;
5-[[6-[3-(Difluoromethyl)-4-fluoro-phenyl]pyrazolo[3,4-b]pyrazin-1-yl]methyl]pyridine-3-carbonitrile;
5-[[6-[3-(Difluoromethyl)-4-fluoro-phenyl]-3-fluoro-pyrazolo[3,4-b]pyrazin-1-yl]methyl]pyridine-3-carbonitrile; and
1-[(5-Chloro-3-pyridyl)methyl]-6-[3-(difluoromethoxy)-4-fluoro-phenyl]pyrazolo[3,4-b]pyrazine;
2-(6-(4-Chloro-2-fluorophenyl)-1H-pyrazolo[3,4-b]pyrazin-1-yl)-N,N-dimethylacetamide;
N,N-Dimethyl-2-(6-(4-(trifluoromethoxy)phenyl)-1H-pyrazolo[3,4-b]pyrazin-1-yl)acetamide;
2-(6-(2,5-Difluorophenyl)-1H-pyrazolo[3,4-b]pyrazin-1-yl)-N,N-dimethylacetamide;
5-((6-(3-(Difluoromethoxy)-4-fluorophenyl)-1H-pyrazolo[3,4-b]pyrazin-1-yl)methyl)oxazolidin-2-one;
6-(3-(Difluoromethoxy)-4-fluorophenyl)-1-((5-methoxypyridin-3-yl)methyl)-1H-pyrazolo[3,4-b]pyrazine; and
2-(6-(4-(1,1-Difluoroethyl)phenyl)-1H-pyrazolo[3,4-b]pyrazin-1-yl)-N,N-dimethylacetamide;
and pharmaceutically acceptable salts, solvates, stereoisomers, isotopic variants, or N-oxides thereof.

22. A compound selected from the group consisting of:
2-[6-[3-(Difluoromethyl)-4-fluoro-phenyl]pyrazolo[3,4-b]pyrazin-1-yl]-N,N-dimethyl-acetamide;
1-(Azetidin-1-yl)-2-[6-[3-(difluoromethyl)-4-fluoro-phenyl]pyrazolo[3,4-b]pyrazin-1-yl]ethanone;
1-(Azetidin-1-yl)-2-[6-[3-(difluoromethoxy)-4-fluoro-phenyl]pyrazolo[3,4-b]pyrazin-1-yl]ethanone; and
2-[6-[3-(Difluoromethyl)-4-fluoro-phenyl]pyrazolo[3,4-b]pyrazin-1-yl]-1-(3-fluoroazetidin-1-yl)ethanone;
and pharmaceutically acceptable salts, solvates, stereoisomers, isotopic variants, or N-oxides thereof.

23. A pharmaceutical composition comprising: (A) an effective amount of at least one compound selected from compounds of Formula (I):

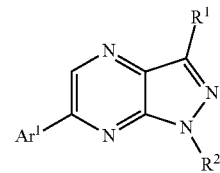

wherein
$R^1$ is H or halo;
$Ar^1$ is selected from the group consisting of:
(a) phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl; and
(b) thienyl substituted with $CF_3$; and
$R^2$ is selected from the group consisting of:
(c)

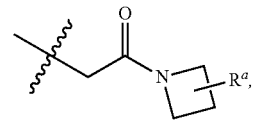

wherein $R^a$ is selected from the group consisting of: H, halo, and $C_{1-6}$alkyl;

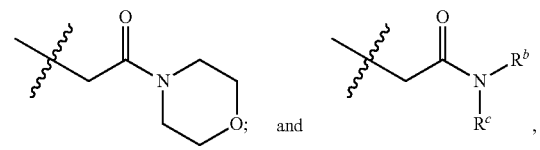

wherein $R^b$ is $C_{1-6}$alkyl, and $R^c$ is $C_{1-6}$alkyl;
(d)

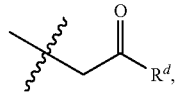

wherein $R^d$ is $C_{1-6}$alkyl, or $C_{3-6}$cycloalkyl; and (e)

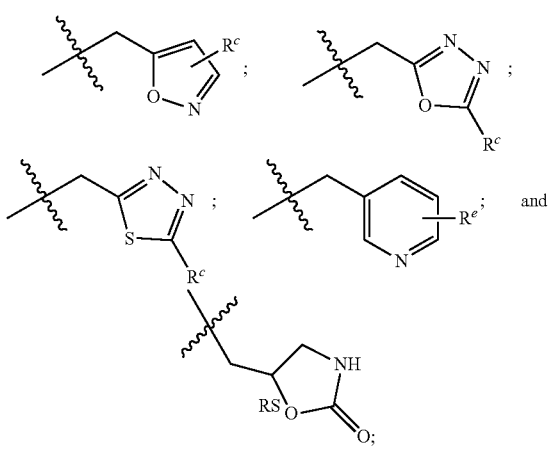

wherein $R^e$ is selected from the group consisting of: halo, $OC_{1-6}$alkyl, and CN;

and pharmaceutically acceptable salts, stereoisomers, isotopic variants, N-oxides, or solvates of compounds of Formula (I);

(B) at least one pharmaceutically acceptable excipient.

24. A pharmaceutical composition comprising an effective amount of at least one compound of embodiment 21 and at least one pharmaceutically acceptable excipient.

25. A method of treating a subject suffering from or diagnosed with a disease, disorder, or medical condition mediated by GluN2B receptor activity, comprising administering to a subject in need of such treatment an effective amount of at least one compound selected from compounds of Formula (I):

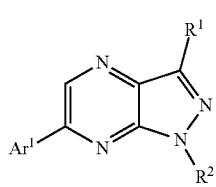

(I)

wherein
$R^1$ is H or halo;
$Ar^1$ is selected from the group consisting of:
(a) phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl; and
(b) thienyl substituted with $CF_3$; and
$R^2$ is selected from the group consisting of:
(c)

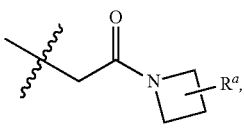

wherein $R^a$ is selected from the group consisting of: H, halo, and $C_{1-6}$alkyl;

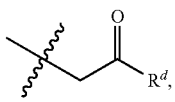

wherein $R^b$ is $C_{1-6}$alkyl, and $R^c$ is $C_{1-6}$alkyl;

(d)

wherein $R^d$ is $C_{1-6}$alkyl, or $C_{3-6}$cycloalkyl; and (e)

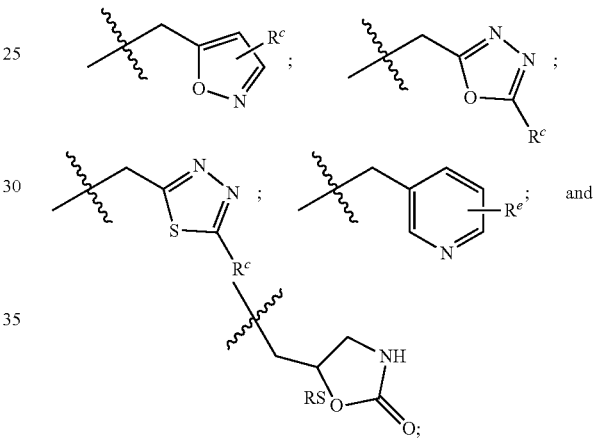

wherein R is selected from the group consisting of: halo, $OC_{1-6}$alkyl, and CN;

and pharmaceutically acceptable salts, stereoisomers, isotopic variants, N-oxides, or solvates of compounds of Formula (I).

26. The method of embodiment 25 wherein the disorder, disease or condition mediated by the GluN2B receptor is selected from the group consisting of: bipolar disorder, major depressive disorder, treatment-resistant depression, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with bacterial or chronic infections, pain, diabetic neuropathy, migraine, cerebral ischemia, schizophrenia, encephalitis, autism and autism spectrum disorders, memory and learning disorders, obsessive compulsive disorder, attention deficit hyperactivity disorder (ADHD) and addictive illnesses.

27. The method of embodiment 25 wherein the disorder, disease or condition is selected from the group consisting of treatment-resistant depression, major depressive disorder and bipolar disorder.

The present disclosure is further exemplified by specific embodiments 1 to 45 below.

1. A compound, having the structure of Formula (I):

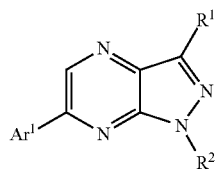
(I)

or a pharmaceutically acceptable salt, solvate, stereoisomer, isotopic variant, or N-oxide thereof,
wherein
$R^1$ is H or halo;
$Ar^1$ is selected from the group consisting of:
  (a) phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl; and
  (b) thienyl substituted with $CF_3$; and
$R^2$ is selected from the group consisting of:
  (c)

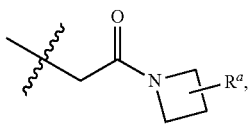

wherein $R^a$ is selected from the group consisting of: H, halo, and $C_{1-6}$alkyl;

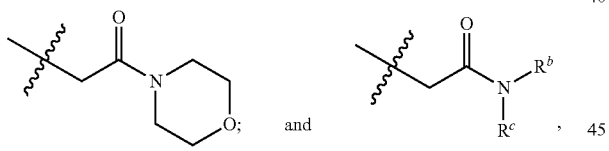

wherein $R^b$ is $C_{1-6}$alkyl, and $R^c$ is $C_{1-6}$alkyl;
  (d)

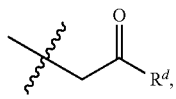

wherein $R^d$ is $C_{1-6}$alkyl, or $C_{3-6}$cycloalkyl; and
  (e)

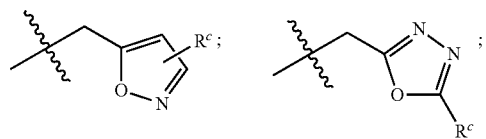

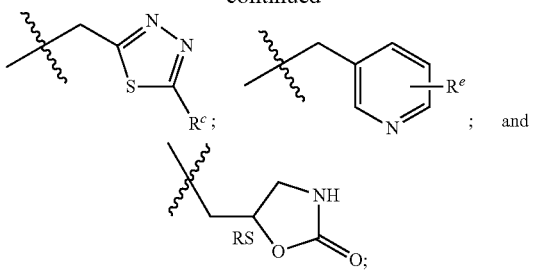

wherein $R^e$ is selected from the group consisting of: halo, $OC_{1-6}$alkyl, and CN.

2. The compound of embodiment 1 or a pharmaceutically acceptable salt, solvate, stereoisomer, isotopic variant, or N-oxide thereof, wherein $R^1$ is H.

3. The compound of embodiment 1 or a pharmaceutically acceptable salt, solvate, stereoisomer, isotopic variant, or N-oxide thereof, wherein $R^1$ is F.

4. The compound of any one of embodiments 1 to 3, or a pharmaceutically acceptable salt, solvate, stereoisomer, isotopic variant, or N-oxide thereof, wherein $Ar^1$ is phenyl substituted with one $CH_3$, $OCF_3$, or $CF_2CH_3$ member.

5. The compound of any one of embodiments 1 to 3, or a pharmaceutically acceptable salt, solvate, stereoisomer, isotopic variant, or N-oxide thereof, wherein $Ar^1$ is phenyl substituted with two members each independently selected from the group consisting of: Cl, F, $CH_3$, $CHF_2$, $CF_3$, $CHF_2CH_3$, $OCH_3$, and $OCHF_2$.

6. The compound of any one of embodiments 1 to 3, or a pharmaceutically acceptable salt, solvate, stereoisomer, isotopic variant, or N-oxide thereof, wherein $Ar^1$ is

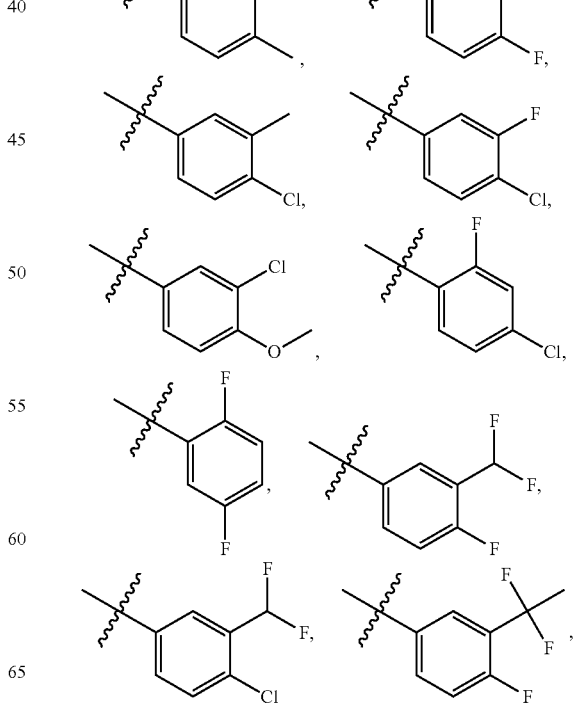

-continued

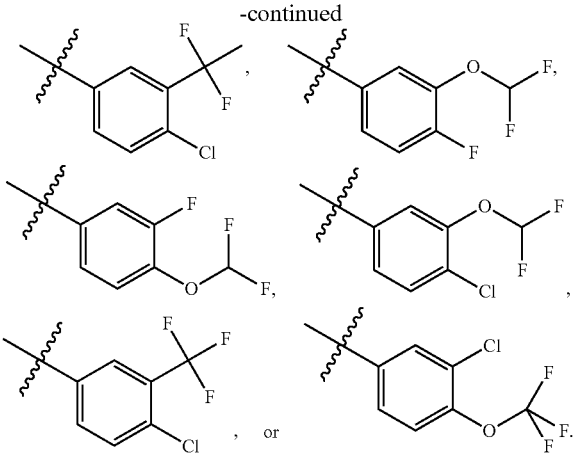

7. The compound of any one of embodiments 1 to 3, or a pharmaceutically acceptable salt, solvate, stereoisomer, isotopic variant, or N-oxide thereof, wherein $Ar^1$ is phenyl substituted with three members each independently selected from the group consisting of: halo, and $CH_3$.

8. The compound of any one of embodiments 1 to 3, or a pharmaceutically acceptable salt, solvate, stereoisomer, isotopic variant, or N-oxide thereof, wherein $Ar^1$ is

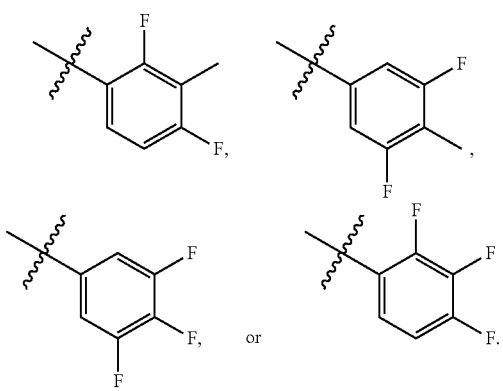

9. The compound of any one of embodiments 1 to 3, or a pharmaceutically acceptable salt, solvate, stereoisomer, isotopic variant, or N-oxide thereof, wherein $Ar^1$ is

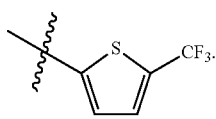 [SMILES: *c1ccc(C(F)(F)F)s1]

10. The compound of any one of embodiments 1 to 9, or a pharmaceutically acceptable salt, solvate, stereoisomer, isotopic variant, or N-oxide thereof, wherein $R^2$ is

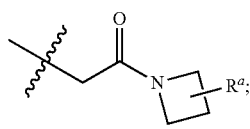

wherein $R^a$ is selected from the group consisting of: H, F, and $CH_3$.

11. The compound of any one of embodiments 1 to 9, or a pharmaceutically acceptable salt, solvate, stereoisomer, isotopic variant, or N-oxide thereof, wherein $R^2$ is

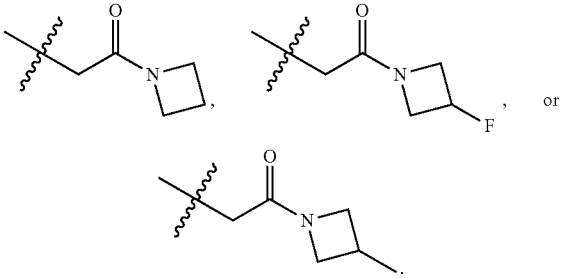

12. The compound of any one of embodiments 1 to 9, or a pharmaceutically acceptable salt, solvate, stereoisomer, isotopic variant, or N-oxide thereof, wherein $R^2$ is

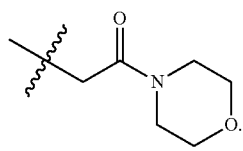 [SMILES: *CC(=O)N1CCOCC1]

13. The compound of any one of embodiments 1 to 9, or a pharmaceutically acceptable salt, solvate, stereoisomer, isotopic variant, or N-oxide thereof, wherein $R^2$ is

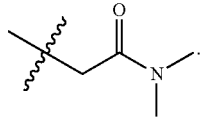 [SMILES: *CC(=O)N(C)C]

14. The compound of any one of embodiments 1 to 9, or a pharmaceutically acceptable salt, solvate, stereoisomer, isotopic variant, or N-oxide thereof, wherein $R^2$ is or

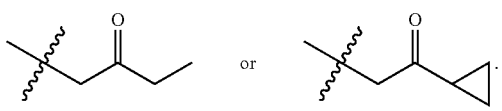

15. The compound of any one of embodiments 1 to 9, or a pharmaceutically acceptable salt, solvate, stereoisomer, isotopic variant, or N-oxide thereof, wherein $R^2$ is

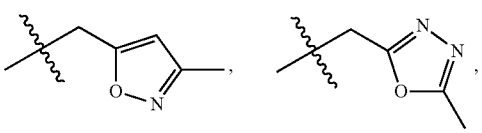

-continued

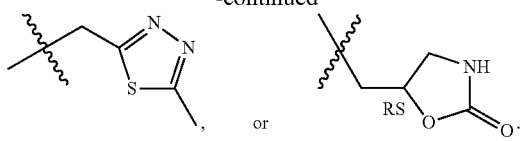

16. The compound of any one of embodiments 1 to 9, or a pharmaceutically acceptable salt, solvate, stereoisomer, isotopic variant, or N-oxide thereof, wherein $R^2$ is

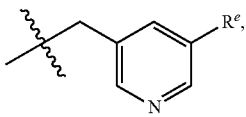

wherein $R^e$ is Cl, F, $OCH_3$, or CN.

17. The compound of embodiment 1 or a pharmaceutically acceptable salt, solvate, stereoisomer, isotopic variant, or N-oxide thereof, having the structure of Formula (IA):

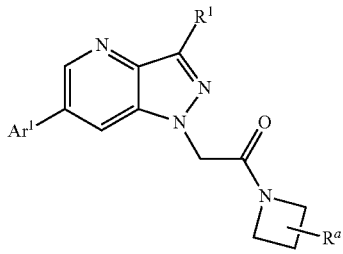

wherein
$R^1$ is H, or F;
$Ar^1$ is phenyl substituted with two members each independently selected from the group consisting of: halo, $C_{1-6}$alkyl, $C_{1-6}$perhaloalkyl, and $OC_{1-6}$perhaloalkyl; and
$R^a$ is H, halo, or $C_{1-6}$alkyl.

18. The compound of embodiment 17 or a pharmaceutically acceptable salt, solvate, stereoisomer, isotopic variant, or N-oxide thereof, wherein $R^1$ is H.

19. The compound of embodiment 1 or a pharmaceutically acceptable salt, solvate, stereoisomer, isotopic variant, or N-oxide thereof, having the structure of Formula (IB):

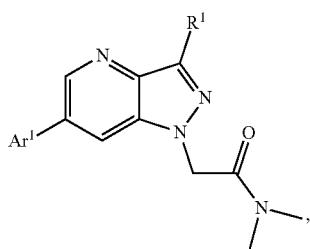

wherein
$R^1$ is H, or F; and
$Ar^1$ is
(a) phenyl substituted with two members each independently selected from the group consisting of: halo, $C_{1-6}$alkyl, $C_{1-6}$perhaloalkyl, and $OC_{1-6}$perhaloalkyl; or
(b) thienyl substituted with $CF_3$.

20. The compound of embodiment 19 or a pharmaceutically acceptable salt, solvate, stereoisomer, isotopic variant, or N-oxide thereof, wherein $R^1$ is H.

21. A compound selected from the compounds in Table 1 and pharmaceutically acceptable salts, solvates, stereoisomers, isotopic variants, and N-oxides thereof.

22. The compound of any one of embodiments 1 to 21, or a pharmaceutically acceptable salt or solvate thereof.

23. The compound of any one of embodiments 1 to 21, or a pharmaceutically acceptable salt or N-oxide thereof.

24. The compound of any one of embodiments 1 to 21, or a pharmaceutically acceptable salt thereof.

25. The compound of any one of embodiments 1 to 21.

26. A pharmaceutically acceptable salt of the compound of any one of embodiments 1 to 21.

27. A pharmaceutical composition comprising the compound of any one of embodiments 1 to 21, or a pharmaceutically acceptable salt, solvate, isotopic variant, or N-oxide thereof, and a pharmaceutically acceptable excipient.

28. A pharmaceutical composition comprising the compound of any one of embodiments 1 to 21, or a pharmaceutically acceptable salt or solvate thereof, and a pharmaceutically acceptable excipient.

29. A pharmaceutical composition comprising the compound of any one of embodiments 1 to 21, or a pharmaceutically acceptable salt or N-oxide thereof, and a pharmaceutically acceptable excipient.

30. A pharmaceutical composition comprising the compound of any one of embodiments 1 to 21, or a pharmaceutically acceptable salt thereof, and a pharmaceutically acceptable excipient.

31. A pharmaceutical composition comprising the compound of any one of embodiments 1 to 21 and a pharmaceutically acceptable excipient.

32. A pharmaceutical composition comprising a pharmaceutically acceptable salt of the compound of any one of embodiments 1 to 21, and a pharmaceutically acceptable excipient.

33. A unit dosage form comprising a therapeutically effective amount of the pharmaceutical composition of any one of embodiments 27 to 32.

34. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt, solvate, isotopic variant, or N-oxide thereof.

35. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt, or solvate thereof.

36. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt or N-oxide thereof.

37. A method of treating a subject suffering from or diagnosed with a disease, disorder, or medical condition mediated by GluN2B receptor activity, comprising administering to the subject a therapeutically effective amount of the compound of any one of embodiments 1 to 21, or a pharmaceutically acceptable salt thereof.

38. A method of treating a subject suffering from or diagnosed with a disease, disorder, or medical condition mediated by GluN2B receptor activity, comprising administering to the subject a therapeutically effective amount of the pharmaceutical composition of any one of embodiments 27 to 32 or the unit dosage form of embodiment 33.

39. The method of any one of embodiments 34 to 38, wherein the disease, disorder or medical condition mediated by GluN2B receptor activity comprises bipolar disorder, major depressive disorder, treatment-resistant depression, a mood disorder, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with a bacterial or chronic infection, pain, diabetic neuropathy, migraine, cerebral ischemia, schizophrenia, encephalitis, autism or an autism spectrum disorder, a memory disorder, a learning disorder, obsessive compulsive disorder, attention deficit hyperactivity disorder (ADHD) or an addictive illness.

40. The method of embodiment 39, wherein the disease, disorder or medical condition mediated by GluN2B receptor activity comprises bipolar disorder, a mood disorder, treatment resistant depression, major depressive disorder, or epilepsy.

41. The method of embodiment 39, wherein the disease, disorder or medical condition mediated by GluN2B receptor activity comprises bipolar disorder.

42. The method of embodiment 39, wherein the disease, disorder or medical condition mediated by GluN2B receptor activity comprises a mood disorder.

43. The method of embodiment 39, wherein the disease, disorder or medical condition mediated by GluN2B receptor activity comprises treatment resistant depression.

44. The method of embodiment 39, wherein the disease, disorder or medical condition mediated by GluN2B receptor activity comprises major depressive disorder.

45. The method of embodiment 39, wherein the disease, disorder or medical condition mediated by GluN2B receptor activity comprises epilepsy.

What is claimed:

1. A compound having the structure of Formula (I):

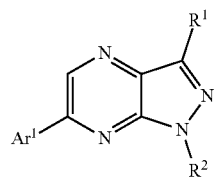

(I)

or a pharmaceutically acceptable salt, solvate, stereoisomer, isotopic variant, or N-oxide thereof,
wherein
$R^1$ is H;
$Ar^1$ is phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl;
$R^2$ is selected from the group consisting of:

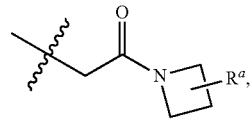

wherein $R^a$ is selected from the group consisting of: H, halo, and $C_{1-6}$alkyl;

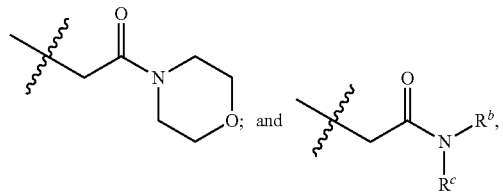

wherein $R^b$ is $C_{1-6}$alkyl and $R^c$ is $C_{1-6}$alkyl.

2. The compound of claim 1 or a pharmaceutically acceptable salt, solvate, stereoisomer, isotopic variant, or N-oxide thereof, wherein $Ar^1$ is phenyl substituted with two members each independently selected from the group consisting of: Cl, F, $CH_3$, $CHF_2$, $CF_3$, $CHF_2CH_3$, $OCH_3$, and $OCHF_2$.

3. The compound of claim 1 or a pharmaceutically acceptable salt, solvate, stereoisomer, isotopic variant, or N-oxide thereof, wherein $Ar^1$ is

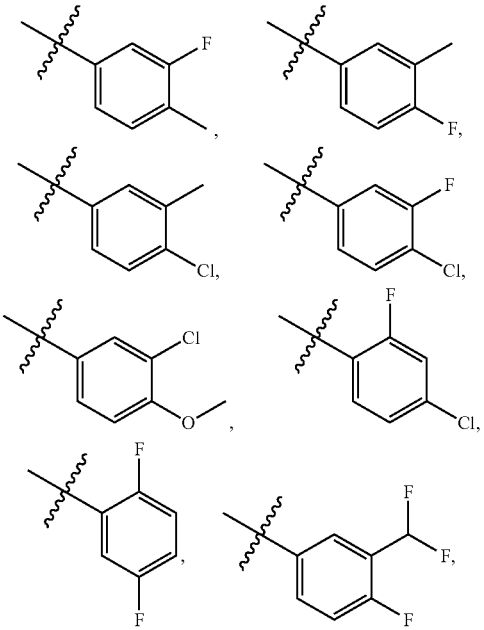

-continued

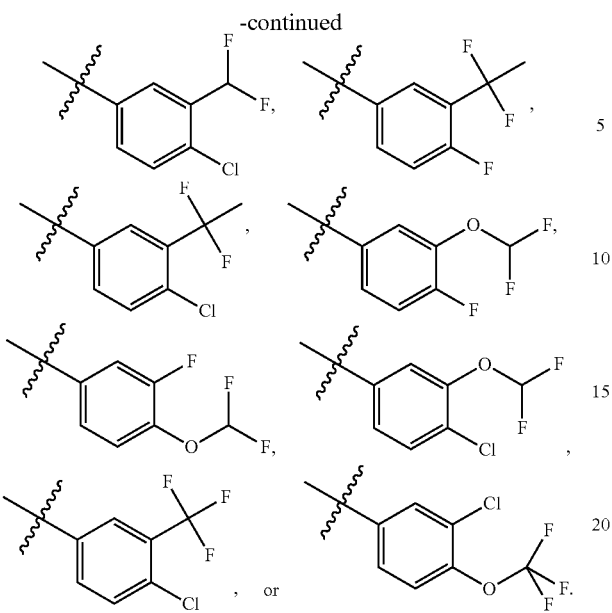

4. The compound of claim 1 or a pharmaceutically acceptable salt, solvate, stereoisomer, isotopic variant, or N-oxide thereof, wherein $R^2$ is

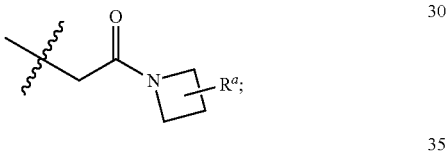

wherein $R^a$ is selected from the group consisting of: H, F, and $CH_3$.

5. The compound of claim 1 or a pharmaceutically acceptable salt, solvate, stereoisomer, isotopic variant, or N-oxide thereof, wherein $R^2$ is

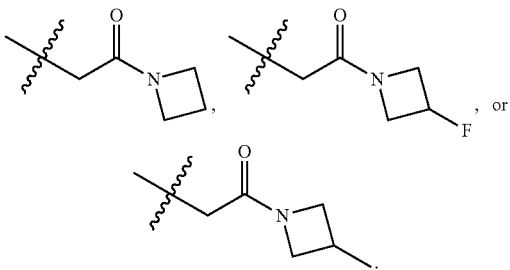

6. The compound of claim 1 or a pharmaceutically acceptable salt, solvate, stereoisomer, isotopic variant, or N-oxide thereof, wherein $R^2$ is

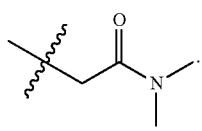 [SMILES: *CC(=O)N(C)C]

7. The compound of claim 1 having the structure of Formula (IA):

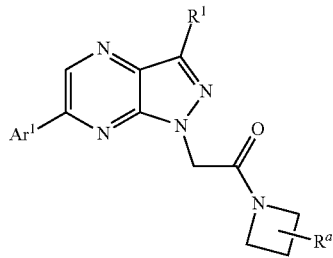

(IA)

or a pharmaceutically acceptable salt, solvate, stereoisomer, isotopic variant, or N-oxide thereof,
wherein
$R^1$ is H;
$Ar^1$ is phenyl substituted with two members each independently selected from the group consisting of: halo, $C_{1-6}$alkyl, $C_{1-6}$perhaloalkyl, and $OC_{1-6}$perhaloalkyl; and
$R^a$ is H, halo, or $C_{1-6}$alkyl.

8. The compound of claim 1 having the structure of Formula (IB):

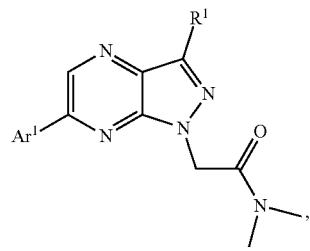

(IB)

or a pharmaceutically acceptable salt, solvate, stereoisomer, isotopic variant, or N-oxide thereof,
wherein
$R^1$ is H; and
$Ar^1$ is phenyl substituted with two members each independently selected from the group consisting of: halo, $C_{1-6}$alkyl, $C_{1-6}$perhaloalkyl, and $OC_{1-6}$perhaloalkyl.

9. A pharmaceutical composition comprising (A) a compound selected from the group consisting of:
1-[6-[3-(Difluoromethyl)-4-fluoro-phenyl]pyrazolo[3,4-b]pyrazin-1-yl]butan-2-one;
2-[6-[4-Chloro-3-(difluoromethoxy)phenyl]pyrazolo[3,4-b]pyrazin-1-yl]-1-cyclopropyl-ethanone;
N, N-Dimethyl-2-[6-[5-(trifluoromethyl)-2-thienyl]pyrazolo[3,4-b]pyrazin-1-yl]acetamide;
N,N-Dimethyl-2-[6-(m-tolyl)pyrazolo[3,4-b]pyrazin-1-yl]acetamide;
2-[6-(4-Chloro-3-fluoro-phenyl)pyrazolo[3,4-b]pyrazin-1-yl]-N, N-dimethyl-acetamide;
2-[6-(3-Fluoro-4-methyl-phenyl)pyrazolo[3,4-b]pyrazin-1-yl]-N, N-dimethyl-acetamide;
2-[6-(4-Fluoro-3-methyl-phenyl)pyrazolo[3,4-b]pyrazin-1-yl]-N, N-dimethyl-acetamide;
2-[6-(4-Chloro-3-methyl-phenyl)pyrazolo[3,4-b]pyrazin-1-yl]-N, N-dimethyl-acetamide;
2-[6-(3-Chloro-4-methoxy-phenyl)pyrazolo[3,4-b] pyrazin-1-yl]-N, N-dimethyl-acetamide;

2-[6-[3-(Difluoromethyl)-4-fluoro-phenyl]pyrazolo[3,4-b]pyrazin-1-yl]-N, N-dimethyl-acetamide;
2-[6-[3-(Difluoromethyl)-4-fluoro-phenyl]-3-fluoro-pyrazolo[3,4-b]pyrazin-1-yl]-N, N-dimethyl-acetamide;
2-[6-[4-Chloro-3-(difluoromethyl)phenyl]pyrazolo[3,4-b]pyrazin-1-yl]-N, N-dimethyl-acetamide;
2-[6-[3-(1, 1-Difluoroethyl)-4-fluoro-phenyl]pyrazolo[3,4-b]pyrazin-1-yl]-N, N-dimethyl-acetamide;
2-[6-[4-Chloro-3-(1, 1-difluoroethyl)phenyl]pyrazolo[3,4-b]pyrazin-1-yl]-N, N-dimethyl-acetamide;
2-[6-[4-Chloro-3-(trifluoromethyl)phenyl]pyrazolo[3,4-b]pyrazin-1-yl]-N, N-dimethyl-acetamide;
2-[6-[3-(Difluoromethoxy)-4-fluoro-phenyl]pyrazolo[3,4-b]pyrazin-1-yl]-N, N-dimethyl-acetamide;
2-[6-[4-(Difluoromethoxy)-3-fluoro-phenyl]pyrazolo[3,4-b]pyrazin-1-yl]-N, N-dimethyl-acetamide;
2-[6-[4-Chloro-3-(difluoromethoxy)phenyl]pyrazolo[3,4-b]pyrazin-1-yl]-N, N-dimethyl-acetamide;
2-[6-[3-Chloro-4-(trifluoromethoxy)phenyl]pyrazolo[3,4-b]pyrazin-1-yl]-N, N-dimethyl-acetamide;
2-[6-(3,5-Difluoro-4-methyl-phenyl)pyrazolo[3,4-b]pyrazin-1-yl]-N, N-dimethyl-acetamide;
2-[6-(2,4-Difluoro-3-methyl-phenyl)pyrazolo[3,4-b]pyrazin-1-yl]-N, N-dimethyl-acetamide;
N, N-Dimethyl-2-[6-(3,4,5-trifluorophenyl)pyrazolo[3,4-b]pyrazin-1-yl]acetamide;
N, N-Dimethyl-2-[6-(2,3,4-trifluorophenyl)pyrazolo[3,4-b]pyrazin-1-yl]acetamide;
1-(Azetidin-1-yl)-2-[6-[3-(difluoromethyl)-4-fluoro-phenyl]pyrazolo[3,4-b]pyrazin-1-yl]ethanone;
1-(Azetidin-1-yl)-2-[6-[3-(difluoromethyl)-4-fluoro-phenyl]-3-fluoro-pyrazolo[3,4-b]pyrazin-1-yl]ethanone;
1-(Azetidin-1-yl)-2-[6-[4-chloro-3-(1, 1-difluoroethyl)phenyl]pyrazolo[3,4-b]pyrazin-1-yl]ethanone;
1-(Azetidin-1-yl)-2-[6-[3-(1, 1-difluoroethyl)-4-fluoro-phenyl]pyrazolo[3,4-b]pyrazin-1-yl]ethanone;
1-(Azetidin-1-yl)-2-[6-[3-(difluoromethoxy)-4-fluoro-phenyl]pyrazolo[3,4-b]pyrazin-1-yl]ethanone;
1-(Azetidin-1-yl)-2-[6-[4-chloro-3-(difluoromethoxy)phenyl]pyrazolo[3,4-b]pyrazin-1-yl]ethanone;
2-[6-[3-(Difluoromethyl)-4-fluoro-phenyl]pyrazolo[3,4-b]pyrazin-1-yl]-1-(3-methylazetidin-1-yl)ethanone;
2-[6-[3-(Difluoromethyl)-4-fluoro-phenyl]-3-fluoro-pyrazolo[3,4-b]pyrazin-1-yl]-1-(3-methylazetidin-1-yl)ethanone;
2-[6-[3-(Difluoromethyl)-4-fluoro-phenyl]pyrazolo[3,4-b]pyrazin-1-yl]-1-(3-fluoroazetidin-1-yl)ethanone;
2-[6-[3-(Difluoromethyl)-4-fluoro-phenyl]-3-fluoro-pyrazolo[3,4-b]pyrazin-1-yl]-1-(3-fluoroazetidin-1-yl)ethanone;
2-[6-[4-Chloro-3-(1, 1-difluoroethyl)phenyl]pyrazolo[3,4-b]pyrazin-1-yl]-1-(3-methylazetidin-1-yl)ethanone;
2-[6-[4-Chloro-3-(1, 1-difluoroethyl)phenyl]pyrazolo[3,4-b]pyrazin-1-yl]-1-(3-fluoroazetidin-1-yl)ethanone;
2-[6-[3-(Difluoromethoxy)-4-fluoro-phenyl]pyrazolo[3,4-b]pyrazin-1-yl]-1-(3-methylazetidin-1-yl)ethanone;
2-[6-[3-(Difluoromethoxy)-4-fluoro-phenyl]pyrazolo[3,4-b]pyrazin-1-yl]-1-(3-fluoroazetidin-1-yl)ethanone;
2-[6-[4-Chloro-3-(1, 1-difluoroethyl)phenyl]pyrazolo[3,4-b]pyrazin-1-yl]-1-morpholino-ethanone;
2-[6-[3-(Difluoromethyl)-4-fluoro-phenyl]pyrazolo[3,4-b]pyrazin-1-yl]methyl]-5-methyl-1,3,4-thiadiazole;
2-[[6-[3-(Difluoromethyl)-4-fluoro-phenyl]pyrazolo[3,4-b]pyrazin-1-yl]methyl]-5-methyl-1,3,4-oxadiazole;
5-[6-[3-(Difluoromethyl)-4-fluoro-phenyl]pyrazolo[3,4-b]pyrazin-1-yl]methyl]-3-methyl-isoxazole;
6-[3-(Difluoromethyl)-4-fluoro-phenyl]-1-[(5-fluoro-3-pyridyl)methyl]pyrazolo[3,4-b]pyrazine;
1-[(5-Chloro-3-pyridyl)methyl]-6-[3-(difluoromethyl)-4-fluoro-phenyl]pyrazolo[3,4-b]pyrazine;
6-[3-(Difluoromethyl)-4-fluoro-phenyl]-1-[(5-methoxy-3-pyridyl)methyl]pyrazolo[3,4-b]pyrazine;
5-[[6-[3-(Difluoromethyl)-4-fluoro-phenyl]pyrazolo[3,4-b]pyrazin-1-yl]methyl]pyridine-3-carbonitrile;
5-[6-[3-(Difluoromethyl)-4-fluoro-phenyl]-3-fluoro-pyrazolo[3,4-b]pyrazin-1-yl]methyl]pyridine-3-carbonitrile; and
1-[(5-Chloro-3-pyridyl)methyl]-6-[3-(difluoromethoxy)-4-fluoro-phenyl]pyrazolo[3,4-b]pyrazine;
2-(6-(4-Chloro-2-fluorophenyl)-1H-pyrazolo[3,4-b]pyrazin-1-yl)-N, N-dimethylacetamide;
N, N-Dimethyl-2-(6-(4-(trifluoromethoxy)phenyl)-1H-pyrazolo[3,4-b]pyrazin-1-yl)acetamide;
2-(6-(2,5-Difluorophenyl)-1H-pyrazolo[3,4-b]pyrazin-1-yl)-N, N-dimethylacetamide;
5-((6-(3-(Difluoromethoxy)-4-fluorophenyl)-1H-pyrazolo[3,4-b]pyrazin-1-yl)methyl)oxazolidin-2-one;
6-(3-(Difluoromethoxy)-4-fluorophenyl)-1-((5-methoxypyridin-3-yl)methyl)-1H-pyrazolo[3,4-b]pyrazine;
2-(6-(4-(1, 1-Difluoroethyl)phenyl)-1H-pyrazolo[3,4-b]pyrazin-1-yl)-N, N-dimethylacetamide;
and pharmaceutically acceptable salts thereof;
and (B) at least one pharmaceutically acceptable excipient.

10. A pharmaceutical composition comprising (A) a compound selected from the group consisting of:
2-[6-[3-(Difluoromethyl)-4-fluoro-phenyl]pyrazolo[3,4-b]pyrazin-1-yl]-N, N-dimethyl-acetamide;
1-(Azetidin-1-yl)-2-[6-[3-(difluoromethyl)-4-fluoro-phenyl]pyrazolo[3,4-b]pyrazin-1-yl]ethanone;
1-(Azetidin-1-yl)-2-[6-[3-(difluoromethoxy)-4-fluoro-phenyl]pyrazolo[3,4-b]pyrazin-1-yl]ethanone;
2-[6-[3-(Difluoromethyl)-4-fluoro-phenyl]pyrazolo[3,4-b]pyrazin-1-yl]-1-(3-fluoroazetidin-1-yl)ethanone;
and pharmaceutically acceptable salts thereof;
and (B) at least one pharmaceutically acceptable excipient.

11. A pharmaceutical composition comprising: (A) at least one compound selected from compounds of Formula (I):

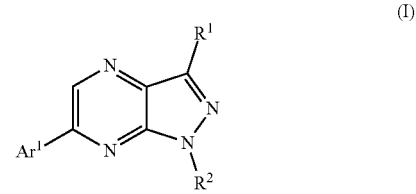

(I)

and pharmaceutically acceptable salts, solvates, stereoisomers, isotopic variants, and N-oxides thereof,
wherein
$R^1$ is H;
$Ar^1$ is phenyl substituted with one, two or three members each independently selected from the group consisting of: halo, $C_{1-6}$alkyl, $C_{1-6}$perhaloalkyl, $OC_{1-6}$alkyl, and $OC_{1-6}$perhaloalkyl; and R² is selected from the group consisting of:

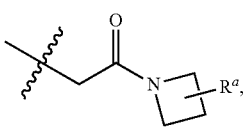

wherein R<sup>a</sup> is selected from the group consisting of: H, halo, and C₁₋₆alkyl;

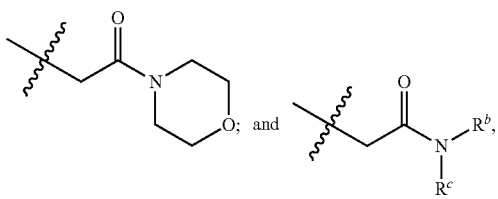

wherein R<sup>b</sup> is C₁₋₆alkyl and R<sup>c</sup> is C₁₋₆alkyl; and
(B) at least one pharmaceutically acceptable excipient.

12. A method of treating a subject suffering from or diagnosed with a disease, disorder, or medical condition mediated by GluN2B receptor activity, comprising administering to a subject in need of such treatment an effective amount of at least one compound selected from compounds of Formula (I):

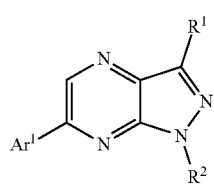

and pharmaceutically acceptable salts, solvates, stereoisomers, isotopic variants, and N-oxides thereof,
wherein
R¹ is H;
Ar¹ is phenyl substituted with one, two or three members each independently selected from the group consisting of: halo, C₁₋₆alkyl, C₁₋₆perhaloalkyl, OC₁₋₆alkyl, and OC₁₋₆perhaloalkyl; and
R² is selected from the group consisting of:

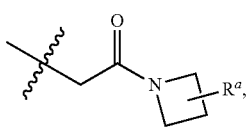

wherein R<sup>a</sup> is selected from the group consisting of: H, halo, and C₁₋₆alkyl;

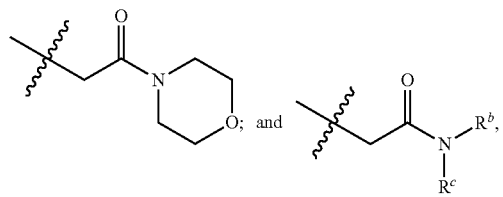

wherein R<sup>b</sup> is C₁₋₆alkyl and R<sup>c</sup> is C₁₋₆alkyl;
wherein the disorder, disease or medical condition mediated by GluN2B receptor activity is selected from the group consisting of: bipolar disorder, major depressive disorder, treatment-resistant depression, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with bacterial or chronic infections, pain, diabetic neuropathy, migraine, cerebral ischemia, schizophrenia, encephalitis, autism and autism spectrum disorders, memory and learning disorders, obsessive compulsive disorder, attention deficit hyperactivity disorder (ADHD) and an addictive illness.

13. The method of claim 12, wherein the disorder, disease or medical condition is selected from the group consisting of treatment-resistant depression, major depressive disorder and bipolar disorder.

14. A method of treating a subject suffering from or diagnosed with treatment-resistant depression, comprising administering to the subject an effective amount of the compound of claim 1 or a pharmaceutically acceptable salt or stereoisomer thereof.

15. A method of treating a subject suffering from or diagnosed with major depressive disorder, comprising administering to the subject an effective amount of the compound of claim 1 or a pharmaceutically acceptable salt or stereoisomer thereof.

16. A method of treating a subject suffering from or diagnosed with treatment-resistant depression, comprising administering to the subject an effective amount of the pharmaceutical composition of claim 9.

17. A method of treating a subject suffering from or diagnosed with major depressive disorder, comprising administering to the subject an effective amount of the pharmaceutical composition of claim 9.

18. A method of treating a subject suffering from or diagnosed with treatment-resistant depression, comprising administering to the subject an effective amount of the pharmaceutical composition of claim 10.

19. A method of treating a subject suffering from or diagnosed with major depressive disorder, comprising administering to the subject an effective amount of the pharmaceutical composition of claim 10.

* * * * *